(12) United States Patent
Oberbörsch et al.

(10) Patent No.: US 7,662,828 B2
(45) Date of Patent: Feb. 16, 2010

(54) SUBSTITUTED 5,6,7,8-TETRAHYDROPYRIDO[4,3-D] PYRIMIDINE-2-YL COMPOUNDS AND 5,6,7,8-TETRAHYDROQUINAZOLINE-2-YL COMPOUNDS

(75) Inventors: Stefan Oberbörsch, Aachen (DE); Bernd Sundermann, Aachen (DE); Corinna Sundermann, Aachen (DE); Michael Haurand, Aachen (DE); Hagen-Heinrich Hennies, Simmerath (DE); Edward Bijsterveld, Nijmegen (NL)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 11/588,238

(22) Filed: Oct. 27, 2006

(65) Prior Publication Data

US 2007/0249631 A1 Oct. 25, 2007

Related U.S. Application Data

(63) Continuation of application No. PCT/EP2005/004489, filed on Apr. 27, 2005.

(30) Foreign Application Priority Data

Apr. 28, 2004 (DE) .................. 10 2004 020 908

(51) Int. Cl.
*C07D 471/04* (2006.01)
*A61K 31/519* (2006.01)
*C07D 239/04* (2006.01)
*A61K 31/517* (2006.01)
*A61K 31/536* (2006.01)
*C07D 265/36* (2006.01)
*C07D 498/04* (2006.01)
*C07D 211/94* (2006.01)
*C07D 317/72* (2006.01)
*A61P 23/00* (2006.01)
*A61P 25/04* (2006.01)

(52) U.S. Cl. .................. 514/264.11; 544/279; 544/292; 544/105; 544/284; 514/230.5; 546/242; 549/341

(58) Field of Classification Search .................. 544/279; 514/264.1, 264.11
See application file for complete search history.

(56) References Cited

U.S. PATENT DOCUMENTS

2007/0135459 A1* 6/2007 Dewdney et al. ........ 514/264.11

FOREIGN PATENT DOCUMENTS

| EP | 0 436 157 A1 | 7/1991 |
|---|---|---|
| WO | WO 99/21857 | 5/1999 |
| WO | WO 01/32659 A1 | 5/2001 |
| WO | WO 01/44246 A1 | 6/2001 |
| WO | WO 02/096422 A2 | 12/2002 |
| WO | WO 03/068771 A1 | 8/2003 |
| WO | WO 2004/016596 A1 | 2/2004 |
| WO | WO 2004/022542 A2 | 3/2004 |

OTHER PUBLICATIONS

Pau, et al., Postgrad. Med. J. 2000; 76:299-306.*
Urban, et al., Neuropharmacology, vol. 44, # 8, Jun. 2003, pp. 983-993.*
Jaeschke, et al., Expert Opin. Ther. Patents (2009) 18(2), 123-142.*
Pridmore, et al., Austral. & New Zeal. J. of Psych., 2004; 38:219-225.*
Goethels, et al., Am. J. Psych. 2004;161:1916-1918.*
Balschun, et al., Neuroscience, vol. 142, # 3, Oct. 27, 2006, 691-702.*
Chen, Doctoral Dissertation, Vanderbilt Univ., Dec. 2007, 154 pages.*
Wu, et al., Neuroscience Ltrs., vol. 307, # 3, Jul. 20, 2001, pp. 183-186.*
Liebich, et al., J. Chromatog. A, vol. 843, Issues 1-2, May 28, 1999, pp. 237-245.*
Sakai, et al., Applied & Environmental Microbiol., Jul. 1996, p. 2669-2672.*
Broos, et al., J. Chem. Soc. Perkin Trans., 1995, 2899-2905.*
Gennaro, Alfonso (Ed.), *Reminaton's Pharmaceutical Sciences*, 1985, Mack Publishing Company, Easton, PA, USA, Part 8 (King, Robert E., Ph.D.) pp. 1409-1680, Table of Contents Only.
Gray, E.G., et al., The Isolation of Nerve Endings From Brain: An Electron-Microscopic Study of Cell Fragments Derived by Homogenization and Centrifugation, Agricultural Research Council Institute of Animal Physiology, Journal of Anatomy, vol. 96, Part 1, pp. 79-96, Babraham, Cambridge.
Lowry, Oliver H., et al., "Protein Measurement With the Folin Phenol Reagent," Department of Pharmacology, Washington University School of Medicine, St. , pp. 265-275, Louis, Missouri, May 28, 1951.
Frink, Martin Ch., et al., "Influence of Tramadol on Neurotransmitter Systems of the Rat Brain," Arzneim.-Forsch./Drug Res. 46 (II), Nr. 11 (1996), pp. 1029-1036.
German Search Report dated Feb. 14, 2005 w/English translation (Eight (8) pages).
International Search Report dated 07/11/2005 (Three (3) pages).

(Continued)

*Primary Examiner*—Mark L Berch
*Assistant Examiner*—Cecilia M Jaisle
(74) *Attorney, Agent, or Firm*—Crowell & Moring LLP

(57) ABSTRACT

Substituted 5,6,7,8-tetrahydro-pyrido[4,3-d]pyrimidin-2-yl and 5,6,7,8-tetrahydro-quinazolin-2-yl compounds, corresponding to formula I

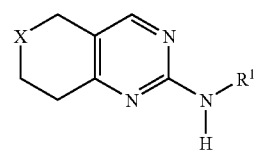

processes for the production thereof, pharmaceutical preparations containing these compounds the use thereof for the production of pharmaceutical preparations and related method of treating or inhibiting certain disorders or conditions, including pain.

26 Claims, No Drawings

OTHER PUBLICATIONS

Z. Magalas et al., "The serotonin/noradrenaline reuptake inhibitor venlifaxine attenuates acquisition, but not maintenance of intravenous self-administration of heroin in rats," *Europ. J. of Pharmacology* 528:103-09 (2005).

D. Mochizucki, "Serotonin and Noradrenaline Reuptake Inhibitors in Animal Models of Pain," *Human Psychopharmacology: Clinical and Experimental* 19:s15-s19 (2004).

K.-T Lu et al., "Endogenous Serotonin Inhibits Epileptiform Activity in Rat Hippocampal CA1 Neurons Via 5-Hydroxytryptamine 1A Receptor Activation", *Neuroscience* 3 (8): 729-37 (1998).

A. Erdinc et al., "The Efficacy of Venlafaxine in the Treatment of Women with Stress Urinary Incontinence," *Arch. Gynecol. Obstet.* DOI 10.1007/s00404-008-0729-x (published online) Springer Verlag (2008).

* cited by examiner

SUBSTITUTED 5,6,7,8-TETRAHYDROPYRIDO[4,3-D] PYRIMIDINE-2-YL COMPOUNDS AND 5,6,7,8-TETRAHYDROQUINAZOLINE-2-YL COMPOUNDS

CROSS-REFERENCE TO RELATED APPLICATIONS

This application is a continuation of International patent application Serial No. PCT/EP2005/004489 filed Apr. 27, 2005 which claims benefit to German patent application Serial No. 10 2004 020 908.1 filed Apr. 28, 2004, the entire disclosures of which are hereby incorporated in their entirety.

FIELD OF THE INVENTION

The present invention relates to substituted 5,6,7,8-tetrahydro-pyrido[4,3-d]-pyrimidin-2-yl and 5,6,7,8-tetrahydro-quinazolin-2-yl compounds, processes for the production thereof, pharmaceutical formulation containing these compounds, methods of producing such pharmaceutical formulation, and related methods of treating or inhibiting certain conditions or disorders, including pain.

BACKGROUND OF THE INVENTION

Pain is one of the basic clinical symptoms. There is a worldwide need for effective pain treatments. The urgency of the requirement for therapeutic methods for providing tailored and targeted treatment of chronic and non-chronic pain, this being taken to mean pain treatment which is effective and satisfactory from the patient's standpoint, is also evident from the large number of scientific papers relating to applied analgesia and to basic nociception research which have appeared in recent times.

Conventional opioids, such as for example morphine, are effective in the treatment of severe to very severe pain, but they often lead to unwanted accompanying symptoms, such as for example respiratory depression, vomiting, sedation, constipation or the development of tolerance. Moreover, they are frequently insufficiently effective in the case of neuropathic pain, suffered in particular by tumour patients.

SUMMARY OF THE INVENTION

One object of the present invention was accordingly to provide novel compounds which are suitable in particular as pharmaceutical active ingredients in pharmaceutical preparations, preferably in pharmaceutical preparations for the prevention and/or treatment of pain, in particular acute pain, chronic pain, neuropathic or visceral pain.

It has now surprisingly been found that the substituted 5,6,7,8-tetrahydro-pyrido-[4,3-d]pyrimidin-2-yl and 5,6,7,8-tetrahydro-quinazolin-2-yl compounds of the general formula I stated hereinafter are suitable for noradrenalin receptor regulation, in particular for inhibiting noradrenalin reuptake (noradrenalin uptake), for 5-HT receptor regulation, in particular for inhibiting 5-hydroxy tryptophan reuptake (5-HT uptake), for mGluR5 receptor regulation and/or for batrachotoxin (BTX) receptor regulation and may therefore be used in particular as pharmaceutical active ingredients in pharmaceutical preparations for preventing and/or treating disorders or diseases associated with these receptors or processes.

The present invention accordingly provides substituted 5,6,7,8-tetrahydro-pyrido-[4,3-d]pyrimidin-2-yl and 5,6,7,8-tetrahydro-quinazolin-2-yl compounds of the general formula I,

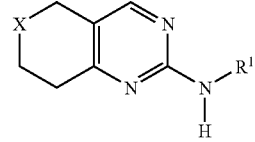

in which

X denotes a C(H)(NHR$^2$) group or an NR$^{2a}$ group,

R$^1$ denotes a —C(=O)—R$^3$ group or a —C(=O)—O—R$^4$ group,

R$^2$, R$^{2a}$, mutually independently, in each case denote a —C(=O)—R$^5$ group or an —S(=O)$_2$—R$^6$ group, R$^3$ denotes a linear or branched, unsubstituted or at least monosubstituted, saturated or unsaturated aliphatic residue, optionally comprising at least one heteroatom as a chain link, an unsubstituted or at least monosubstituted, saturated or unsaturated cycloaliphatic residue, optionally comprising at least one heteroatom as a ring member, which residue may be attached via a linear or branched, unsubstituted or at least monosubstituted alkylene group, optionally comprising at least one heteroatom as a chain link, or an unsubstituted or at least monosubstituted aryl or heteroaryl residue, which may be attached via a linear or branched, unsubstituted or at least monosubstituted alkylene group, R$^4$ denotes an unsubstituted or at least monosubstituted aryl or heteroaryl residue, which may be attached via a linear or branched, unsubstituted or at least monosubstituted alkylene group, R$^5$ denotes a linear or branched, unsubstituted or at least monosubstituted, saturated or unsaturated aliphatic residue, optionally comprising at least one heteroatom as a chain link, an unsubstituted or at least monosubstituted, saturated or unsaturated cycloaliphatic residue, optionally comprising at least one heteroatom as a ring member, which residue may be attached via a linear or branched, unsubstituted or at least monosubstituted alkylene group, optionally comprising at least one heteroatom as a chain link, and/or be fused with an unsubstituted or at least monosubstituted, mono- or polycyclic ring system, an unsubstituted or at least monosubstituted aryl or heteroaryl residue, which may be attached via a linear or branched, unsubstituted or at least monosubstituted alkylene, alkenylene or alkynylene group, optionally comprising at least one heteroatom as a chain link and/or be fused with an unsubstituted or at least monosubstituted, mono- or polycyclic ring system, a —C(=O)—R$^7$ residue, which may be attached via a linear or branched, unsubstituted or at least monosubstituted alkylene group, a —C(=O)—R$^8$ residue, which may be attached via a linear or branched, unsubstituted or at least monosubstituted alkylene group, or an —N(H)—C(=O)—O—R$^9$ residue, which may be attached via a linear or branched, unsubstituted or at least monosubstituted alkylene group, optionally comprising at least one —N(H)—C(=O) or at least one —C(=O)—N(H) grouping as a chain link, R$^6$ denotes a group —NR$^{10}$R$^{11}$, a linear or branched, unsubstituted or at least monosubstituted, saturated or unsaturated aliphatic residue, optionally comprising at least one heteroatom as a chain link, an unsubstituted or at least monosubstituted, saturated or unsaturated cycloaliphatic residue, optionally comprising at least one heteroatom as a ring member, optionally fused with an unsubstituted or at least monosubstituted mono- or polycyclic ring system, which residue may be attached via a linear or branched, unsubstituted or at least monosubstituted alkylene group, optionally comprising at least one heteroatom as a chain link and/or be bridged with a linear or branched alkylene group, or an unsubstituted or at least monosubstituted aryl or heteroaryl residue, which may be attached via a linear or branched, unsubstituted or at least monosubstituted alkylene group and/or be fused with an unsubstituted or at least monosubstituted mono- or polycyclic ring system, $R^7$ denotes a linear or branched, unsubstituted or at least monosubstituted alkyl residue, an unsubstituted or at least monosubstituted aryl or heteroaryl residue, an unsubstituted or at least monosubstituted, saturated or unsaturated cycloaliphatic residue, optionally comprising at least one heteroatom as a ring member, which residue may be fused with an unsubstituted or at least monosubstituted mono- or polycyclic ring system, or an —$NR^{7a}R^{7b}$ residue, in which the residues $R^{7a}$ and $R^{7b}$, identical or different, in each case denote a linear or branched alkyl residue, $R^8$ denotes a linear or branched, unsubstituted or at least monosubstituted alkyl residue or an unsubstituted or at least monosubstituted aryl or heteroaryl residue, optionally attached via a linear or branched alkylene group, $R^9$ denotes a linear or branched, unsubstituted or at least monosubstituted alkyl residue, an unsubstituted or at least monosubstituted aryl or heteroaryl residue, optionally attached via a linear or branched alkylene group, or an unsubstituted or at least monosubstituted, saturated or unsaturated cycloaliphatic residue, which may be fused with at least one unsubstituted or at least monosubstituted mono- or polycyclic ring system, and $R^{10}$, $R^{11}$, identical or different, in each case denote a linear or branched alkyl residue, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

If one or more of the substituents $R^3$ and $R^5$-$R^9$ denote a saturated or unsaturated aliphatic residue, i.e. an alkyl, alkenyl or alkynyl residue, which is mono- or polysubstituted, for example 1, 2, 3, 4, 5, 6, 7, 8 or 9 times, the substituents thereof may, in each case mutually independently, preferably be selected from the group consisting of F, Cl, Br, —OH, —SH and —$NH_2$. Alkenyl residues comprise at least one C—C double bond and alkynyl residues at least one C—C triple bond.

Examples of suitable alkyl, alkenyl and alkynyl residues, which may be mono- or polysubstituted, are methyl, ethyl, n-propyl, iso-propyl, n-butyl, iso-butyl, sec-butyl, tert-butyl, n-pentyl, iso-pentyl, neopentyl, n-hexyl, 2-hexyl, n-heptyl, n-octyl, n-nonyl, n-decyl, —$C(H)(C_2H_5)_2$, —$C(H)(n-C_3H_7)_2$, —$CH_2$—$CH_2$—$C(H)(CH_3)$—$(CH_2)_3$—$CH_3$, vinyl, ethynyl, propenyl, allyl, propynyl, butenyl, butynyl, pentenyl, pentynyl, hexenyl, hexynyl, —CH=CH—CH=CH—$CH_3$ and —$CH_2$—$CH_2$—CH=$CH_2$.

If one or more of the substituents $R^3$, $R^5$ and $R^6$ denote a saturated or unsaturated aliphatic residue, i.e. an alkyl, alkenyl or alkynyl residue, which comprises one or more, for example 1, 2, 3, 4 or 5, heteroatoms as chain link(s), these heteroatoms, in each case mutually independently, may preferably be selected from the group consisting of oxygen, sulfur and nitrogen (NH). Preferably, these heteroatoms are located in a non-terminal position of the respective residue. Residues such as —$CH_2$—$CH_2$—S—$CH_3$, —$CH_2$—O—$CH_2$—$CH_2$—O—$CH_3$, —$CH_2$—O—$CH_3$ or —$CH_2$—$CH_2$—O—$CH_3$ may be mentioned by way of example.

If one or more of the substituents $R^3$, $R^5$-$R^7$ and $R^9$ denote a cycloaliphatic residue or comprises a cycloaliphatic residue, which is mono- or polysubstituted, for example 1, 2, 3, 4 or 5 times, the substituents thereof may, in each case mutually independently, preferably be selected from the group consisting of —$C_{1-5}$ alkyl, —C(=O)—O—$C_{1-5}$-alkyl, —C(=O)—$CF_3$, —S(=O)$_2$—$C_{1-5}$-alkyl, —S(=O)$_2$-phenyl, oxo (=O) and phenyl, wherein the $C_{1-5}$ alkyl residue may in each case be linear or branched and the phenyl residue may in each case be mono- or polysubstituted, for example 1, 2, 3, 4 or 5 times, identically or differently, with a substituent selected from the group consisting of F, Cl, Br and I. Particularly preferably, the substituents, in each case mutually independently, may be selected from the group consisting of —C(=O)—O-tert-butyl, —C(=O)—$CF_3$, —S(=O)$_2$-methyl, —S(=O)$_2$-phenyl, oxo, and phenyl, wherein the phenyl residue may in each case be mono- or polysubstituted, for example 1, 2, 3, 4 or 5 times, identically or differently, with a substituent selected from the group consisting of F, Cl and Br.

If the cycloaliphatic residues comprise one or more, for example 1, 2 or 3, heteroatoms as ring members, these, in each case mutually independently, may preferably be selected from the group consisting of nitrogen, oxygen and sulfur.

Examples of suitable cycloaliphatic residues, which may be mono- or polysubstituted, are cyclopropyl, cyclobutyl, cyclopentyl, cyclohexyl, cycloheptyl, cyclooctyl, cyclopentenyl, cyclohexenyl, cycloheptenyl, cyclooctenyl, imidazolidinyl, tetrahydrofuranyl(tetrahydrofuryl), piperidinyl, piperazinyl, morpholinyl and dithiolanyl.

If one or more of the substituents $R^3$-$R^9$ denote an aryl or heteroaryl residue or comprise an aryl or heteroaryl residue, which is mono- or polysubstituted, for example 1, 2, 3, 4 or 5 times, the substituents thereof may, in each case mutually independently, preferably be selected from the group consisting of halogen, —CN, —$NO_2$, —OH, —SH, $C_{1-5}$ alkyl, $C_{1-5}$ alkoxy, —S—$C_{1-5}$-alkyl, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —S(=O)$_2$-phenyl, —S(=O)$_2$—$C_{1-5}$ alkyl, N($C_{1-5}$alkyl)($C_{1-5}$-alkyl), —C(=O)—O—$C_{1-5}$-alkyl, —$CH_2$—O—C(=O)-phenyl, —O—C(=O)-phenyl, —NH—C(=O)—$C_{1-5}$-alkyl, —C≡C-phenyl, —C≡C-naphthyl, —C≡C-pyrrolyl, —C≡C-indolyl, —C≡C-furyl(—C≡C-furanyl), —C≡C-benzo[b]furanyl, —C≡C-thienyl(-C≡C-thiophenyl), —C≡C-benzo[b]thienyl, —C≡C-pyrazolyl, —C≡C-imidazolyl, —C≡C-thiazolyl, —C≡C-thiadiazolyl, —C≡C-triazolyl, —C≡C-oxazolyl, —C≡C-isoxazolyl, —C≡C-pyridinyl, —C≡C-pyridazinyl, —C≡C-pyrimidinyl, —C≡C-pyrazinyl, —C≡C-pyranyl, —C≡C-indazolyl, —C≡C-purinyl, —C≡C-indolizinyl, —C≡C-quinolinyl, —C≡C-isoquinolinyl, —C≡C-quinazolinyl, pyrazolyl, phenyl, furyl(furanyl), thiadiazolyl, thiophenyl(thienyl), phenoxy and benzyl, wherein the cyclic substituents may themselves in each case be mono- or polysubstituted, for example 1, 2, 3, 4 or 5 times, identically or differently, with a substituent selected from the group consisting of F, Cl, Br, I.

Particularly preferably, the substituents, in each case mutually independently, may be selected from the group consisting of F, Cl, Br, I, —CN, —$NO_2$, —OH, —SH, methyl, ethyl, n-propyl, iso-propyl, n-butyl, iso-butyl, sec-butyl, tert-butyl, n-pentyl, neopentyl, methoxy, ethoxy, n-propoxy, iso-propoxy, n-butyloxy, iso-butyloxy, sec-butyloxy, tert-butyloxy, —S-methyl, —S-ethyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, pyrazolyl, phenyl, —N(CH$_3$)$_2$, —N(C$_2$H$_5$)$_2$, —CH$_2$—O—C (=O)-phenyl, —C(=O)—O—CH$_3$, —C(=O)—O—C$_2$H$_5$, —NH—C(=O)—CH$_3$, —O—C(=O)-phenyl, —C≡C-phenyl, —C≡C-furyl (—C≡C-furanyl), —C≡C-thiadiazolyl, —C≡C-thiophenyl (—C≡C-thienyl), phenyl, furyl (furanyl), thiadiazolyl, thiophenyl(thienyl), phenoxy and benzyl, wherein the cyclic substituents may themselves in each case be mono- or polysubstituted, for example 1, 2, 3, 4 or 5 times, identically or differently, with a substituent selected from the group consisting of F, Cl, Br, I.

Examples of suitable aryl residues which may be mentioned are phenyl, 1-naphthyl and 2-naphthyl.

If one or more of the substituents $R^3$-$R^9$ denote a heteroaryl residue or comprise a heteroaryl residue, the heteroatom(s) thereof may, in each case mutually independently, preferably be selected from the group consisting of oxygen, sulfur and nitrogen. For example, the heteroaryl residues may comprise 1, 2, 3, 4 or 5 heteroatoms.

Suitable heteroaryl residues which may be mentioned are, for example, pyrrolyl, indolyl, furyl(furanyl), benzo[b]furanyl, thienyl(thiophenyl), benzo[b]thienyl, pyrazolyl, imidazolyl, thiazolyl, thiadiazolyl, triazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl and quinazolinyl.

For the purposes of the present invention, a mono- or polycyclic ring system should be understood to mean mono- or polycyclic hydrocarbon residues which may be saturated, unsaturated or aromatic and optionally comprise one or more, for example 1, 2, 3, 4 or 5, heteroatoms as ring members. Such a mono- or polycyclic ring system may, for example, be fused (anellated) with a cycloaliphatic residue, an aryl residue or a heteroaryl residue.

If a polycyclic ring system is present, the different rings may, in each case mutually independently, exhibit a different degree of saturation, i.e. be saturated, unsaturated or aromatic. The heteroatoms of each ring may, in each case identically or differently, preferably be selected from the group consisting of oxygen, nitrogen and sulfur. Preferably, the respective rings of the mono- or polycyclic ring system are 5- or 6-membered. Preferably, polycyclic ring systems should be understood to mean bicyclic ring systems.

If one or more of the substituents $R^5$, $R^6$, $R^7$ and $R^9$ comprise a monocyclic or polycyclic ring system which is mono- or polysubstituted, for example 1, 2, 3, 4 or 5 times, the substituents thereof may, in each case mutually independently, preferably be selected from the group consisting of halogen, —CN, —NO$_2$, —OH, —SH, $C_{1-5}$ alkyl, $C_{1-5}$ alkoxy, —S—$C_{1-5}$-alkyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, —S(=O)$_2$—$C_{1-5}$-alkyl, N($C_{1-5}$alkyl)($C_{1-5}$ alkyl), —C(=O)—O-$C_{1-5}$-alkyl, —CH$_2$—O—C(=O)-phenyl, —O—C(=O)-phenyl, —NH—C(=O)—$C_{1-5}$-alkyl, —C≡C-phenyl, —C≡C-naphthyl, —C≡C-pyrrolyl, —C≡C-indolyl, —C≡C-furyl (—C≡C-furanyl), —C≡C-benzo[b]furanyl, —C≡C-thienyl (—C≡C-thiophenyl), —C≡C-benzo[b]thienyl, —C≡C-pyrazolyl, —C≡C-imidazolyl, —C≡C-thiazolyl, —C≡C-thiadiazolyl, —C≡C-triazolyl, —C≡C-oxazolyl, —C≡C-isoxazolyl, —C≡C-pyridinyl, —C≡C-pyridazinyl, —C≡C-pyrimidinyl, —C≡C-pyrazinyl, —C≡C-pyranyl, —C≡C-indazolyl, —C≡C-purinyl, —C≡C-indolizinyl, —C≡C-quinolinyl, —C≡C-isoquinolinyl, —C≡C-quinazolinyl, pyrazolyl, phenyl, furyl(furanyl), thiadiazolyl, thiophenyl(thienyl), phenoxy and benzyl, wherein the cyclic substituents may themselves in each case be mono- or polysubstituted, for example 1, 2, 3, 4 or 5 times, identically or differently, with a substituent selected from the group consisting of F, Cl, Br, I. Particularly preferably, the substituents, in each case mutually independently, may be selected from the group consisting of F, Cl, Br, I, —CN, —NO$_2$, —OH, —SH, methyl, ethyl, n-propyl, iso-propyl, n-butyl, iso-butyl, sec-butyl, tert-butyl, n-pentyl, neopentyl, methoxy, ethoxy, n-propoxy, iso-propoxy, n-butyloxy, iso-butyloxy, sec-butyloxy, tert-butyloxy, —S-methyl, —S-ethyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, pyrazolyl, phenyl, —N(CH$_3$)$_2$, —N(C$_2$H$_5$)$_2$, —CH$_2$—O—C(=O)-phenyl, —C(=O)—O—CH$_3$, —C(=O)—O—C$_2$H$_5$, —NH—C(=O)—CH$_3$, —O—C(=O)-phenyl, furyl(furanyl), thiadiazolyl, thiophenyl(thienyl), phenoxy and benzyl, wherein the cyclic substituents may themselves in each case be mono- or polysubstituted, for example 1, 2, 3, 4 or 5 times, identically or differently, with a substituent selected from the group consisting of F, Cl, Br, I.

If one of the above-stated substituents $R^3$-$R^6$ comprises a linear or branched alkylene, alkenylene or alkynylene group, which is mono- or polysubstituted, for example 1, 2, 3, 4 or 5 times, the substituents thereof may, in each case mutually independently, preferably be selected from the group consisting of F, Cl, Br, hydroxy and unsubstituted phenyl.

If the alkylene, alkenylene or alkynylene group comprises one or more, for example 1, 2, 3, 4 or 5, heteroatoms as chain link(s), these may preferably be selected from the group consisting of oxygen, sulfur and nitrogen (NH).

Examples which may be stated are alkylene, alkenylene or alkynylene groups such as —(CH$_2$)—, —(CH$_2$)$_2$—, —(CH$_2$)$_3$—, —(CH$_2$)$_4$—, —(CH$_2$)$_5$—, —C(H)(CH$_2$phenyl), —C(H)(phenyl), —C(H)(C)(H)(CH$_3$)$_2$), —C(C$_2$H$_5$)(H)—, —(CH$_2$)—O—, —(CH$_2$)$_2$—O—, —(CH$_2$)$_3$—O—, —(CH$_2$)$_4$—O—, —O—(CH$_2$)—, —O—(CH$_2$)$_2$—, —O—(CH$_2$)$_3$—, —O—(CH$_2$)$_4$—, —C(C$_2$H$_5$)(H)—O—, —O—C(C$_2$H$_5$)(H)—, —CH$_2$—O—CH$_2$—, —CH$_2$—S—CH$_2$—, —C(CH$_3$)$_2$—, —C(H)(CH$_3$)—, —CH=CH— and —C≡C—.

Preferred substituted 5,6,7,8-tetrahydro-pyrido[4,3-d]pyrimidin-2-yl and 5,6,7,8-tetrahydro-quinazolin-2-yl compounds of the above-stated general formula I are those
in which
X denotes a C(H)(NHR$^2$) group or an NR$^{2a}$ group,
$R^1$ denotes a —C(=O)—$R^3$ group or a —C(=O)—O—$R^4$ group,
$R^2$, $R^{2a}$, mutually independently, in each case denote a —C(=O)—$R^5$ group or an —S(=O)$_2$—$R^6$ group,
$R^3$ denotes a linear or branched, unsubstituted or at least monosubstituted, saturated or unsaturated aliphatic $C_{1-8}$ residue, optionally comprising at least one heteroatom as a chain link, an unsubstituted or at least monosubstituted, saturated or unsaturated 3- to 8-membered cycloaliphatic residue, optionally comprising at least one heteroatom as a ring member, which residue may be attached via a linear or branched, unsubstituted or at least monosubstituted $C_{1-3}$ alkylene group, optionally comprising at least one heteroatom as a chain link, or an unsubstituted or at least monosubstituted 5- to 14-membered aryl or heteroaryl residue, which may be attached via a linear or branched, unsubstituted or at least monosubstituted $C_{1-3}$ alkylene group, $R^4$ denotes an unsubstituted or at least monosubstituted 5- to 14-membered aryl or heteroaryl residue, which may be attached via a linear or branched, unsubstituted or at least monosubstituted $C_{1-3}$ alkylene group, $R^5$ denotes a linear or branched, unsubstituted or at least monosubstituted, saturated or unsaturated aliphatic $C_{1-10}$ residue, optionally comprising at least one heteroatom as a chain link, an unsubstituted or at least monosubstituted, saturated or unsaturated 3- to 8-membered cycloaliphatic residue, optionally comprising at least one heteroatom as a ring member, which residue may be attached via a linear or branched, unsubstituted or at least monosubstituted $C_{1-6}$ alkylene group, optionally comprising at least one heteroatom as a chain link and/or be fused with an unsubstituted or at least monosubstituted, mono- or polycyclic ring system, an unsubstituted or at least monosubstituted 5- to 14-membered aryl or heteroaryl residue, which may be attached via a linear or branched, unsubstituted or at least monosubstituted $C_{1-6}$ alkylene, $C_{2-6}$ alkenylene or $C_{2-6}$ alkynylene group, optionally comprising at least one heteroatom as a chain link and/or be fused with an unsubstituted or at least monosubstituted, mono- or polycyclic ring system, a —C(=O)—$R^7$ residue, which may be attached via a linear or branched, unsubstituted or at least monosubstituted $C_{1-3}$ alkylene group, a —C(=O)—$R^8$ residue, which may be attached via a linear or branched, unsubstituted or at least monosubstituted $C_{1-3}$ alkylene group, or an —N(H)—C(=O)—O—$R^9$ residue, which may be attached via a linear or branched, unsubstituted or at least monosubstituted $C_{1-8}$ alkylene group, optionally comprising at least one —N(H)—C(=O) or at least one —C(=O)—N(H) grouping as a chain link, $R^6$ denotes a group —$NR^{10}R^{11}$, a linear or branched, unsubstituted or at least monosubstituted, saturated or unsaturated aliphatic $C_{1-10}$ residue, optionally comprising at least one heteroatom as a chain link, an unsubstituted or at least monosubstituted, saturated or unsaturated cycloaliphatic residue, optionally comprising at least one heteroatom as a ring member, optionally fused with an unsubstituted or at least monosubstituted mono- or polycyclic ring system, which residue may be attached via a linear or branched, unsubstituted or at least monosubstituted $C_{1-6}$ alkylene group, optionally comprising at least one heteroatom as a chain link and/or be bridged with a linear or branched $C_{1-6}$ alkylene group, or an unsubstituted or at least monosubstituted 5- to 14-membered aryl or heteroaryl residue, which may be attached via a linear or branched, unsubstituted or at least monosubstituted $C_{1-6}$ alkylene group and/or be fused with an unsubstituted or at least monosubstituted mono- or polycyclic ring system, $R^7$ denotes a linear or branched, unsubstituted or at least monosubstituted $C_{1-3}$ alkyl residue, an unsubstituted or at least monosubstituted 5- to 14-membered aryl or heteroaryl residue, an unsubstituted or at least monosubstituted, saturated or unsaturated 5-, 6- or 7-membered cycloaliphatic residue, optionally comprising at least one heteroatom as a ring member, which residue may be fused with an unsubstituted or at least monosubstituted mono- or polycyclic ring system, or denotes an —$NR^{7a}R^{7b}$ residue, in which the residues $R^{7a}$ and $R^{7b}$, identical or different, in each case denote a linear or branched $C_{1-5}$ alkyl residue, $R^8$ denotes a linear or branched, unsubstituted or at least monosubstituted $C_{1-3}$ alkyl residue or an unsubstituted or at least monosubstituted 5- or 6-membered aryl or heteroaryl residue, optionally attached via a linear or branched $C_{1-3}$ alkylene group, $R^9$ denotes a linear or branched, unsubstituted or at least monosubstituted $C_{1-3}$ alkyl residue, an unsubstituted or at least monosubstituted 5- or 6-membered aryl or heteroaryl residue, optionally attached via a linear or branched $C_{1-3}$ alkylene group, or an unsubstituted or at least monosubstituted, saturated or unsaturated 5- or 6-membered cycloaliphatic residue, which may be fused with at least one unsubstituted or at least monosubstituted mono- or polycyclic ring system, and, $R^{10}$, $R^{11}$, identical or different, in each case denote a linear or branched $C_{1-5}$ alkyl residue, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are substituted 5,6,7,8-tetrahydro-pyrido[4,3-(d)]pyrimidin-2-yl and 5,6,7,8-tetrahydro-quinazolin-2-yl compounds of the above-stated general formula I, in which $R^3$ denotes a linear or branched, unsubstituted or at least monosubstituted $C_{1-8}$ alkyl residue, optionally comprising one or more oxygen atoms and/or one or more NH groups as chain link(s), an unsubstituted or at least monosubstituted, saturated or unsaturated 5-, 6- or 7-membered cycloaliphatic residue, optionally comprising at least one heteroatom as a ring member, which residue may be attached via a linear or branched, unsubstituted or at least monosubstituted $C_{1-3}$ alkylene group, optionally comprising at least one heteroatom as a chain link, or an unsubstituted or at least monosubstituted phenyl residue, thiophenyl residue (thienyl residue), furanyl residue (furyl residue), pyridinyl residue or naphthyl residue, which may be attached via a linear or branched, unsubstituted or at least monosubstituted $C_{1-3}$ alkylene group, preferably a methyl, ethyl, n-propyl, iso-propyl, n-butyl, iso-butyl, sec-butyl or tert-butyl residue, an unsubstituted, saturated or unsaturated 5-, 6- or 7-membered cycloaliphatic residue, optionally comprising one or more oxygen atoms and/or one or more nitrogen atoms as ring member(s), which residue may be attached via a —$(CH_2)$—, —$(CH_2)_2$ or —$(CH_2)_3$ group, or a phenyl residue, thiophenyl residue (thienyl residue), furanyl residue (furyl residue), pyridinyl residue or naphthyl residue, which may be attached via a —$(CH_2)$—, —$(CH_2)_2$ or —$(CH_2)_3$ group and/or be mono- or polysubstituted, identically or differently, with a substituent selected from the group consisting of methyl, ethyl, n-propyl, iso-propyl, n-butyl, iso-butyl, sec-butyl, tert-butyl, methoxy, ethoxy, n-propoxy, iso-propoxy, n-butoxy, iso-butoxy, sec-butoxy, tert-butoxy, F, Cl, Br, I, —CN and —$CF_3$, and the respective remaining residues X, $R^1$, $R^2$, $R^{2a}$ and $R^4$ to $R^{11}$ have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Also preferred are substituted 5,6,7,8-tetrahydro-pyrido[4,3-d]pyrimidin-2-yl and 5,6,7,8-tetrahydro-quinazolin-2-yl compounds of the above-stated general formula I, in which the residue $R^4$ denotes a phenyl residue optionally attached via a —$(CH_2)$, —$(CH_2)_2$ or —$(CH_2)_3$ bridge, wherein the phenyl ring, unsubstituted or at least monosubstituted, identical or different, may be substituted with a substituent selected from among the group consisting of methyl, ethyl, n-propyl, iso-propyl, n-butyl, iso-butyl, sec-butyl, tert-butyl, methoxy, ethoxy, n-propoxy, iso-propoxy, n-butoxy, iso-butoxy, sec-butoxy, tert-butoxy, F, Cl, Br, I, —CN and —CF$_3$, preferably an unsubstituted benzyl residue, and the respective remaining residues X, $R^1$, $R^2$, $R^{2a}$, $R^3$ and $R^5$ to $R^{11}$ have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Likewise preferred are substituted 5,6,7,8-tetrahydro-pyrido[4,3-d]pyrimidin-2-yl and 5,6,7,8-tetrahydro-quinazolin-2-yl compounds of the above-stated general formula I, in which $R^5$ denotes a linear or branched $C_{1-10}$ alkyl residue, optionally comprising one or more oxygen atoms and/or optionally one or more sulfur atoms and/or optionally one or more —N(H) groups as chain link(s), a linear or branched $C_{2-10}$ alkenyl residue, optionally comprising one or more oxygen atoms and/or optionally one or more sulfur atoms and/or optionally one or more —N(H) groups as chain link(s), a linear or branched $C_{2-10}$ alkynyl residue, optionally comprising one or more oxygen atoms and/or optionally one or more sulfur atoms and/or optionally one or more —N(H) groups as chain link(s), an unsubstituted or at least monosubstituted, saturated or unsaturated 3- to 8-membered cycloaliphatic residue, optionally comprising one or more heteroatoms, mutually independently, selected from the group consisting of oxygen, sulfur and nitrogen as ring member(s), which residue may be attached via a —(CH$_2$)—, —(CH$_2$)$_2$—, —(CH$_2$)$_3$—, —(CH$_2$)$_4$—, —C(C$_2$H$_5$)(H)—, —(CH$_2$)—O—, —(CH$_2$)$_2$—O—, —(CH$_2$)$_3$—O—, —(CH$_2$)$_4$—O—, —O—(CH$_2$)—, —O—(CH$_2$)$_2$—, —O—(CH$_2$)$_3$—, —O—(CH$_2$)$_4$—, —C(C$_2$H$_5$)(H)—O—, —O—C(C$_2$H$_5$)(H)—, —CH$_2$—O—CH$_2$—, —CH$_2$—S—CH$_2$—, —C(CH$_3$)$_2$ or —C(H)(CH$_3$) group and/or be fused with an unsubstituted or at least monosubstituted, 5- or 6-membered monocyclic ring system, an unsubstituted or at least monosubstituted, 5- or 6-membered aryl or heteroaryl residue, which may be attached via a —(CH$_2$)—, —(CH$_2$)$_2$—, —(CH$_2$)$_3$—, —(CH$_2$)$_4$—, —C(C$_2$H$_5$)(H)—, —(CH$_2$)—O—, —(CH$_2$)$_2$—O—, —(CH$_2$)$_3$—O—, —(CH$_2$)$_4$—O—, —O—(CH$_2$)—, —O—(CH$_2$)$_2$—, —O—(CH$_2$)$_3$—, —O—(CH$_2$)$_4$—, —C(C$_2$H$_5$)(H)—O—, —O—C(C$_2$H$_5$)(H)—, —CH$_2$—O—CH$_2$—, —CH$_2$—S—CH$_2$—, —C(CH$_3$)$_2$—, —C(H)(CH$_3$)— or —CH═CH— group and/or be fused with an unsubstituted or at least monosubstituted 5- or 6-membered, monocyclic ring system, a —C(═O)—$R^7$ residue, which may be attached via a —(CH$_2$)—, —(CH$_2$)$_2$ or —(CH$_2$)$_3$ group, a —C(═O)—$R^8$ residue, which may be attached via a linear or branched $C_{1-3}$ alkylene group which is unsubstituted or mono- or polysubstituted with a phenyl residue, or an —N(H)—C(═O)—O—$R^9$ residue, which may be attached via a linear or branched $C_{1-8}$ alkylene group which is unsubstituted or mono- or polysubstituted with a phenyl residue and optionally comprises at least one —N(H)—C(═O) or at least one —C(═O)—N(H) grouping as a chain link, preferably a residue selected from the group consisting of methyl, ethyl, n-propyl, iso-propyl, n-butyl, sec-butyl, tert-butyl, n-pentyl, neopentyl, iso-pentyl, —C(H)(C$_2$H$_5$)$_2$, —C(H)(n-C$_3$H$_7$)$_2$—, —CH═CH—CH═CH—CH$_3$, —CH$_2$—CH$_2$—CH═CH$_2$, —CH$_2$—CH$_2$—C(H) (CH$_3$)—(CH$_2$)$_3$—CH$_3$, —CH$_2$—O—CH$_3$ and —CH$_2$—O—CH$_2$—CH$_2$—O—CH$_3$, a residue selected from the group consisting of cyclopropyl, cyclobutyl, cyclopentyl, cyclohexyl, cycloheptyl, cyclooctyl, piperidinyl, piperazinyl, morpholinyl, tetrahydrofuranyl(tetrahydrofuryl), dithiolanyl, 1,2,3,4-tetrahydroindolyl, 1,2,3,4-tetrahydronaphthyl, 1,3-dihydroisoindolyl, benzooxazolyl and imidazolidinyl, wherein the cyclic residue in each case may be attached via a —(CH$_2$)—, —(CH$_2$)$_2$—, —(CH$_2$)$_3$—, —(CH$_2$)$_4$—, —C(C$_2$H$_5$)(H)—, —(CH$_2$)—O—, —(CH$_2$)$_2$—O—, —(CH$_2$)$_3$—O—, —(CH$_2$)$_4$—O—, —O—(CH$_2$)—, —O—(CH$_2$)$_4$—, —C(C$_2$H$_5$)(H)—O—, —O—C(C$_2$H$_5$)(H)—, —CH$_2$—O—CH$_2$—, —CH$_2$—S—CH$_2$—, —C(CH$_3$)$_2$—, or —C(H)(CH$_3$) group and/or be mono- or polysubstituted, identically or differently, with a substituent selected from the group consisting of phenyl, —C(═O)—O-tert-butyl, oxo (═O), —S(═O)$_2$-methyl and —S(═O)$_2$-phenyl, wherein the above-stated phenyl residue may in each case be mono- or polysubstituted, identically or differently, with a substituent selected from the group consisting of F, Cl, Br and I, a residue selected from the group consisting of phenyl, naphthyl, furanyl(furyl), thiophenyl(thienyl), pyridinyl, isoxazolyl, triazolyl, pyrazolyl, thiazolyl, benzo[1,2,5]-oxadiazolyl, 2,3-dihydrobenzofuranyl, quinolinyl, chromanyl, chromenyl, benzo[b]furanyl, benzo[b]thiophenyl, benzo[1,3]-dioxinyl, indolyl, 2,3-dihydro-indolyl, 3,4-dihydro-benzo[1,4]oxazinyl and 1,2,3,4-tetrahydroisoquinolinyl, wherein the cyclic residue may in each case be attached via a —(CH$_2$)—, —(CH$_2$)$_2$—, —(CH$_2$)$_3$—, —(CH$_2$)$_4$—, —C(C$_2$H$_5$)(H)—, —(CH$_2$)—O—, —(CH$_2$)$_2$—O—, —(CH$_2$)$_3$—O—, —(CH$_2$)$_4$—O—, —O—(CH$_2$)—, —O—(CH$_2$)$_2$—, —O—(CH$_2$)$_3$—, —O—(CH$_2$)$_4$—, —C(C$_2$H$_5$)(H)—O—, —O—C(C$_2$H$_5$)(H)—, —CH$_2$—O—CH$_2$—, —CH$_2$—S—CH$_2$—, —C(CH$_3$)$_2$—, —C(H)(CH$_3$) or —CH═CH— group and/or be mono- or polysubstituted, identically or differently, with a substituent selected from the group consisting of F, Cl, Br, I, —CN, —NO$_2$, —OH, —SH, methyl, ethyl, n-propyl, iso-propyl, n-butyl, iso-butyl, sec-butyl, tert-butyl, n-pentyl, iso-pentyl, neopentyl, methoxy, ethoxy, n-propoxy, iso-propoxy, n-butyloxy, iso-butyloxy, sec-butyloxy, tert-butyloxy, —S-methyl, —S-ethyl, —CF$_3$, —CHF$_2$, —CH$_2$F, —O—CF$_3$, —O—CHF$_2$, —O—CH$_2$F, —S—CF$_3$, —S—CHF$_2$, —S—CH$_2$F, —S(═O)$_2$-phenyl, pyrazolyl, phenyl, —N(CH$_3$)$_2$, —N(C$_2$H$_5$)$_2$, —CH$_2$—O—C(═O)-phenyl, —O—C(═O)-phenyl, furyl(furanyl), thiadiazolyl, thiophenyl(thienyl), phenoxy and benzyl, and wherein the cyclic substituents may themselves in each case be mono- or polysubstituted, identically or differently, with a substituent selected from the group consisting of F, Cl, Br, I, a —C(═O)—$R^7$ residue, which may be attached via a —(CH$_2$)—, —(CH$_2$)$_2$ or —(CH$_2$)$_3$ group, a —C(═O)—O—$R^8$ residue, which may be attached via a —(CH$_2$)—, —(CH$_2$)$_2$—, —(CH$_2$)$_3$ or —C(H)(phenyl) group, or an —N(H)—C(═O)—O—$R^9$ residue, which may be attached via a —(CH$_2$)—, —(CH$_2$)$_2$—, —(CH$_2$)$_3$—, —(CH$_2$)$_4$—, —(CH$_2$)$_5$—, —C(H)(CH$_2$phenyl), —C(H)(phenyl), —C(H)(C(H)(CH$_3$)$_2$) or —C(H)(CH$_2$—CH(CH$_3$)$_2$)—NH—C(═O)—CH$_2$ group, and the respective remaining residues X, $R^1$, $R^2$, $R^{2a}$, $R^3$, $R^4$ and $R^6$ to $R^{11}$ have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Also preferred are substituted 5,6,7,8-tetrahydro-pyrido[4,3-d]pyrimidin-2-yl and 5,6,7,8-tetrahydro-quinazolin-2-yl compounds of the above-stated general formula I, in which $R^6$ a group —$NR^{10}R^{11}$, a linear or branched, unsubstituted $C_{1-10}$ alkyl residue, a linear or branched, unsubstituted $C_{2-10}$ alkenyl residue, a linear or branched, unsubstituted, $C_{2-10}$ alkynyl residue, an unsubstituted or at least monosubstituted, saturated or unsaturated 3-, 4-, 5-, 6-, 7- or 8-membered cycloaliphatic residue, which may be attached via a linear or branched $C_{1-3}$ alkylene group and/or be bridged with a linear or branched $C_{1-3}$ alkylene group, an unsubstituted or at least monosubstituted 5- to 6-membered aryl or heteroaryl residue, which may be attached via a linear or branched $C_{1-6}$ alkylene group and/or be fused with an unsubstituted or at least monosubstituted 5- or 6-membered monocyclic ring system, preferably a group —$NR^{10}R^{11}$, a linear or branched, unsubstituted $C_{1-5}$ alkyl residue, a linear or branched, unsubstituted $C_{2-5}$ alkenyl residue, a linear or branched, unsubstituted, $C_{2-5}$ alkynyl residue, an unsubstituted or at least monosubstituted, saturated or unsaturated, 5-, 6- or 7-membered cycloaliphatic residue, which may be attached via a —(CH$_2$)—, —(CH$_2$)$_2$, or —(CH$_2$)$_3$ group and/or be bridged with a —(C)(CH$_3$)$_2$) group, or an unsubstituted or at least monosubstituted, 5- or 6-membered aryl or heteroaryl residue, which may be attached via a —(CH$_2$)—, —(CH$_2$)$_2$—, or —(CH$_2$)$_3$ group and/or be fused with an unsubstituted or at least monosubstituted, 5- or 6-membered monocyclic ring system, optionally containing one or more oxygen atoms as ring member(s) and/or one or more nitrogen atoms as ring member(s), particularly preferably a group —$NR^{10}R^{11}$, a methyl, ethyl, n-propyl, iso-propyl, n-butyl, iso-butyl, sec-butyl or tert-butyl residue, a 7,7-dimethyl-2-oxo-bicyclo[2.2.1]heptyl residue optionally attached via a —(CH$_2$)—, —(CH$_2$)$_2$ or —(CH$_2$)$_3$ group, or a phenyl, naphthyl, thiophenyl(thienyl), furanyl, (furyl), thiazolyl, pyrazolyl, 2,3-dihydro-benzo[1,4]-dioxinyl, 1,2,3,4-tetrahydroiso-quinolinyl or 3,4-dihydrobenzo[1,4]oxazinyl residue, which may be attached via a —(CH$_2$), —(CH$_2$)$_2$, or —(CH$_2$)$_3$ group and/or be mono- or polysubstituted, identically or differently, with a substituent selected from the group consisting of F, Cl, Br, I, methyl, ethyl, n-propyl, iso-propyl, n-butyl, iso-butyl, sec-butyl, tert-butyl, n-pentyl, iso-pentyl, neopentyl, methoxy, ethoxy, —CN, —CF$_3$, —CF$_2$H, —CFH$_2$, —NO$_2$, —C(=O)—CF$_3$, —O—CF$_3$, —C(=O)—O—CH$_3$, —C(=O)—O—C$_2$H$_5$, —NH—C(=O)—CH$_3$, —S(=O)$_2$—CH$_3$ and phenyl, and the respective remaining residues X, $R^1$, $R^2$, $R^{2a}$, $R^3$, $R^5$ and $R^7$ to $R^{11}$ have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Moreover, those substituted 5,6,7,8-tetrahydro-pyrido[4,3-d]pyrimidin-2-yl and 5,6,7,8-tetrahydro-quinazolin-2-yl compounds of the above-stated general formula I are preferred, in which the residue $R^7$ denotes a linear or branched, unsubstituted $C_{1-3}$ alkyl residue, an unsubstituted, 5- or 6-membered aryl or heteroaryl residue, an unsubstituted, saturated or unsaturated 5-, 6- or 7-membered cycloaliphatic residue, optionally comprising a nitrogen atom as a ring member, which residue may be fused with an unsubstituted, 6-membered monocyclic ring system, or an —$NR^{7a}R^{7b}$ residue, in which the residues $R^{7a}$ and $R^{7b}$, identical or different, in each case denote a linear or branched $C_{1-3}$ alkyl residue, preferably a methyl, ethyl, n-propyl, phenyl, indolyl, 2,3-dihydroindolyl, dimethylamino or diethylamino residue, and the respective remaining residues X, $R^1$, $R^2$, $R^{2a}$, $R^3$ to $R^6$ and $R^8$ to $R^{11}$ have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Likewise preferred are substituted 5,6,7,8-tetrahydro-pyrido[4,3-d]pyrimidin-2-yl and 5,6,7,8-tetrahydro-quinazolin-2-yl compounds of the above-stated general formula I, in which $R^8$ denotes a linear or branched, unsubstituted $C_{1-3}$ alkyl residue or a phenyl residue optionally attached via a linear or branched $C_{1-3}$ alkylene group, particularly preferably a methyl, ethyl, phenyl or benzyl residue, and the respective remaining residues X, $R^1$, $R^2$, $R^{2a}$, $R^3$ to $R^7$ and $R^9$ to $R^{11}$ have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Also preferred are substituted 5,6,7,8-tetrahydro-pyrido[4,3-d]pyrimidin-2-yl and 5,6,7,8-tetrahydro-quinazolin-2-yl compounds of the above-stated general formula I, in which $R^9$ denotes a linear or branched, unsubstituted $C_{1-3}$ alkyl residue, an unsubstituted 5- or 6-membered aryl or heteroaryl residue, optionally attached via a linear or branched $C_{1-3}$ alkylene group, or an unsubstituted or at least monosubstituted, saturated or unsaturated, 5- or 6-membered cycloaliphatic residue, which may be fused with at least one unsubstituted, 6-membered monocyclic ring system, preferably a methyl, ethyl, n-propyl, iso-propyl, n-butyl, iso-butyl, sec-butyl, tert-butyl, or a phenyl or fluorenyl residue optionally attached via a —(CH$_2$) group, and the respective remaining residues X, $R^1$, $R^2$, $R^{2a}$, $R^3$ to $R^8$ and $R^{10}$ and $R^{11}$ have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Likewise preferred are substituted 5,6,7,8-tetrahydro-pyrido[4,3-d]pyrimidin-2-yl and 5,6,7,8-tetrahydro-quinazolin-2-yl compounds of the above-stated general formula I, in which the residues $R^{10}$ and $R^{11}$, identical or different, in each case denote a methyl, ethyl, n-propyl or iso-propyl residue, and the respective remaining residues X, $R^1$, $R^2$, $R^{2a}$ and $R^3$ to $R^9$ have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Particularly preferred are substituted 5,6,7,8-tetrahydropyrido[4,3-d]pyrimidin-2-yl and 5,6,7,8-tetrahydro-quinazolin-2-yl compounds of the general formula I,

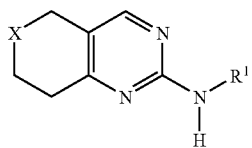

I in which

X denotes a C(H)(NHR²) group or an $NR^{2a}$ group, $R^1$ denotes a —C(=O)—$R^3$ group or a —C(=O)—O—$R^4$ group, $R^2$, $R^{2a}$, mutually independently, in each case denote a —C(=O)—$R^5$ group or an —S(=O)$_2$—$R^6$ group, $R^3$ denotes a methyl, ethyl, n-propyl, iso-propyl, n-butyl, iso-butyl, sec-butyl or tert-butyl residue, an unsubstituted, saturated or unsaturated 5-, 6- or 7-membered cycloaliphatic residue, optionally comprising one or more oxygen atoms and/or one or more nitrogen atoms as ring member(s), which residue may be attached via a —(CH$_2$)—, —(CH$_2$)$_2$ or —(CH$_2$)$_3$ group, or a phenyl residue, thiophenyl residue (thienyl residue), furanyl residue (furyl residue), pyridinyl residue or naphthyl residue, which may be attached via a —(CH$_2$)—, —(CH$_2$)$_2$ or —(CH$_2$)$_3$ group and/or be mono- or polysubstituted, identically or differently, with a substituent selected from the group consisting of methyl, ethyl, n-propyl, iso-propyl, n-butyl, iso-butyl, sec-butyl, tert-butyl, methoxy, ethoxy, n-propoxy, iso-propoxy, n-butoxy, iso-butoxy, sec-butoxy, tert-butoxy, F, Cl, Br, I, —CN and —CF$_3$, $R^4$ denotes an unsubstituted benzyl residue, $R^5$ denotes a residue selected from the group consisting of methyl, ethyl, n-propyl, iso-propyl, n-butyl, sec-butyl, tert-butyl, n-pentyl, iso-pentyl, neopentyl, —C(H)(C$_2$H$_5$)$_2$, —C(H)(n-C$_3$H$_7$)$_2$, —CH=CH—CH=CH—CH$_3$, —CH$_2$—CH$_2$—CH=CH$_2$, —CH$_2$—CH$_2$—C(H)(CH$_3$)—(CH$_2$)$_3$—CH$_3$, —CH$_2$—O—CH$_3$ and —CH$_2$—O—CH$_2$—CH$_2$—O—CH$_3$, a residue selected from the group consisting of cyclopropyl, cyclobutyl, cyclopentyl, cyclohexyl, cycloheptyl, cyclooctyl, piperidinyl, piperazinyl, morpholinyl, tetrahydrofuranyl(tetrahydrofuryl), dithiolanyl, 1,2,3,4-tetrahydroindolyl, 1,2,3,4-tetrahydronaphthyl, 1,3-dihydroisoindolyl, benzooxazolyl and imidazolidinyl, wherein the cyclic residue may in each case be attached via a —(CH$_2$), —(CH$_2$)$_2$, —(CH$_2$)$_3$, —(CH$_2$)$_4$, —C(C$_2$H$_5$)(H), —(CH$_2$)—O, —(CH$_2$)$_2$—O, —(CH$_2$)$_3$—O, —(CH$_2$)$_4$—O, —O—(CH$_2$), —O—(CH$_2$)$_2$, —O—(CH$_2$)$_3$, —O—(CH$_2$)$_4$, —C(C$_2$H$_5$)(H)—O, —O—C(C$_2$H$_5$)(H), —CH$_2$—O—CH$_2$, —CH$_2$—S—CH$_2$, —C(CH$_3$)$_2$, or —C(H)(CH$_3$) group and/or mono- or polysubstituted, identically or differently, with a substituent selected from the group consisting of phenyl, —C(=O)—O-tert-butyl, oxo (=O), —S(=O)$_2$-methyl and —S(=O)$_2$-phenyl, and wherein the above-stated phenyl residues may in each case be mono- or polysubstituted, identically or differently, with a substituent selected from the group consisting of F, Cl, Br and I, a residue selected from the group consisting of phenyl, naphthyl, furanyl(furyl), thiophenyl(thienyl), pyridinyl, isoxazolyl, triazolyl, pyrazolyl, thiazolyl, benzo[1,2,5]-oxadiazolyl, 2,3-dihydrobenzofuranyl, quinolinyl, chromanyl, chromenyl, benzo[b]furanyl, benzo[b]thiophenyl, benzo[1,3]-dioxinyl, indolyl, 2,3-dihydro-indolyl, 3,4-dihydro-benzo[1,4]oxazinyl and 1,2,3,4-tetrahydroisoquinolinyl, wherein the cyclic residue may in each case be attached via a —(CH$_2$), —(CH$_2$)$_2$, —(CH$_2$)$_3$, —(CH$_2$)$_4$, —C(C$_2$H$_5$)(H), —(CH$_2$)—O, —(CH$_2$)$_2$—O, —(CH$_2$)$_3$—O, —(CH$_2$)$_4$—O, —O—(CH$_2$)—, —O—(CH$_2$)$_2$—, —O—(CH$_2$)$_3$, —O—(CH$_2$)$_4$, —C(C$_2$H$_5$)(H)—O, —O—C(C$_2$H$_5$)(H), —CH$_2$—O—CH$_2$, —CH$_2$—S—CH$_2$, —C(CH$_3$)$_2$, —C(H)(CH$_3$) or —CH=CH— group and/or be mono- or polysubstituted, identically or differently, with a substituent selected from the group consisting of F, Cl, Br, I, —CN, —NO$_2$, —OH, —SH, methyl, ethyl, n-propyl, iso-propyl, n-butyl, iso-butyl, sec-butyl, tert-butyl, n-pentyl, neopentyl, methoxy, ethoxy, n-propoxy, iso-propoxy, n-butyloxy, iso-butyloxy, sec-butyloxy, tert-butyloxy, —S-methyl, —S-ethyl, —CF$_3$, —CHF$_2$, —CH$_2$F, —O—CF$_3$, —O—CHF$_2$, —O—CH$_2$F, —S—CF$_3$, —S—CHF$_2$, —S—CH$_2$F, —S(=O)$_2$-phenyl, pyrazolyl, phenyl, —N(CH$_3$)$_2$, —N(C$_2$H$_5$)$_2$, —CH$_2$—O—C(=O)-phenyl, —O—C(=O)-phenyl, furyl(furanyl), thiadiazolyl, thiophenyl(thienyl), phenoxy and benzyl, and wherein the cyclic substituents may themselves in each case be mono- or polysubstituted, identically or differently, with a substituent selected from the group consisting of F, Cl, Br, I, denotes a —C(=O)—$R^7$ residue, which may be attached via a —(CH$_2$)—, —(CH$_2$)$_2$ or —(CH$_2$)$_3$ group, a —C(=O)—O—$R^8$ residue, which may be attached via a —(CH$_2$), —(CH$_2$)$_2$, —(CH$_2$)$_3$ or —C(H)(phenyl) group, or an —N(H)—C(=O)—O—$R^9$ residue, which may be attached via a —(CH$_2$), —(CH$_2$)$_2$, —(CH$_2$)$_3$, —(CH$_2$)$_4$, —(CH$_2$)$_5$, —C(H)(CH$_2$-phenyl), —C(H)(phenyl), —C(H)(C(H)(CH$_3$)$_2$) or —C(H)(CH$_2$—CH(CH$_3$)$_2$)—NH—C(=O)—CH$_2$ group, $R^6$ denotes a group —NR$^{10}$R$^{11}$, a methyl, ethyl, n-propyl, iso-propyl, n-butyl, iso-butyl, sec-butyl or tert-butyl residue, a 7,7-dimethyl-2-oxo-bicyclo[2.2.1]heptyl residue optionally attached via a —(CH$_2$)—, —(CH$_2$)$_2$ or —(CH$_2$)$_3$ group, or a phenyl, naphthyl, thiophenyl(thienyl), furanyl, (furyl), thiazolyl, pyrazolyl, 2,3-dihydro-benzo[1,4]-dioxinyl, 1,2,3,4-tetrahydroiso-quinolinyl or 3,4-dihydrobenzo[1,4]oxazinyl residue, which may be attached via a —(CH$_2$), —(CH$_2$)$_2$, or —(CH$_2$)$_3$ group and/or be mono- or polysubstituted, identically or differently, with a substituent selected from the group consisting of F, Cl, Br, I, methyl, ethyl, n-propyl, iso-propyl, n-butyl, iso-butyl, sec-butyl, tert-butyl, n-pentyl, iso-pentyl, neopentyl, methoxy, ethoxy, —CN, —CF$_3$, —CF$_2$H, —CFH$_2$, —NO$_2$, —C(=O)—CF$_3$, —O—CF$_3$, —C(=O)—O—CH$_3$, —C(=O)—O—C$_2$H$_5$, —NH—C(=O)—CH$_3$, —S(=O)$_2$—CH$_3$ and phenyl, $R^7$ denotes a methyl, ethyl, n-propyl, phenyl, indolyl, 2,3-dihydroindolyl, dimethylamino or diethylamino residue $R^8$ denotes a methyl, ethyl, phenyl or benzyl residue, $R^9$ denotes a methyl, ethyl, n-propyl, iso-propyl, n-butyl, iso-butyl, sec-butyl, tert-butyl, or a phenyl or fluorenyl residue optionally attached via a —(CH$_2$) group, $R^{10}$, $R^{11}$, identical or different, in each case denote a methyl, ethyl, n-propyl or iso-propyl residue, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Very particularly preferred are substituted 5,6,7,8-tetrahydro-pyrido[4,3-d]pyrimidin2-yl and 5,6,7,8-tetrahydro-quinazolin-2-yl compounds of the general formula I selected from the group consisting of

[1] 3-fluoro-N-[6-(4-fluoro-benzoyl)-5,6,7,8-tetrahydro-pyrido[4,3-d]pyrimidin-2-yl]-benzamide,

[2] 3,5-dichloro-N-[6-(3-fluoro-4-methoxy-benzoyl)-5,6,7,8-tetrahydro-pyrido-[4,3-d]pyrimidin-2-yl]-benzamide,

[3] 4-tert-butyl-N-(6-hexanoyl-5,6,7,8-tetrahydro-pyrido[4,3-d]pyrimidin-2-yl)-benzamide,

[4] N-(6-acetyl-5,6,7,8-tetrahydro-pyrido[4,3-d]pyrimidin-2-yl)-3,4-dichloro-benzamide,

[5] 3,5-dichloro-N-[6-(3-trifluoromethyl-benzoyl)-5,6,7,8-tetrahydro-pyrido-[4,3-d]pyrimidin-2-yl]-benzamide,

[6] 3-chloro-N-[6-(4-methoxy-2,3,6-trimethyl-benzenesulfonyl)-5,6,7,8-tetrahydro-pyrido[4,3-d]pyrimidin-2-yl]-benzamide,

[7] N-[6-(2-ethoxy-benzoyl)-5,6,7,8-tetrahydro-pyrido[4,3-d]pyrimidin-2-yl]-3-fluoro-benzamide,

[8] 3-chloro-N-[6-(3-phenyl-propionyl)-5,6,7,8-tetrahydro-pyrido[4,3-d]-pyrimidin-2-yl]-benzamide,

[9] 4-tert-butyl-N-[6-(isoxazole-5-carbonyl)-5,6,7,8-tetrahydro-pyrido[4,3-d]-pyrimidin-2-yl]-benzamide,

[10] N-[6-(2-benzylsulfanyl-acetyl)-5,6,7,8-tetrahydro-pyrido[4,3-d]pyrimidin-2-yl]-2-methoxy-benzamide,

[11] thiophene-2-carboxylic acid {6-[2-(4-chloro-phenyl)-2-methyl-propionyl]-5,6,7,8-tetrahydro-pyrido[4,3-d]pyrimidin-2-yl}-amide,

[12] N-(6-benzoyl-5,6,7,8-tetrahydro-pyrido[4,3-d]pyrimidin-2-yl)-3-methyl-benzamide,

[13] N-[6-(2,3-dihydro-benzofuran-5-carbonyl)-5,6,7,8-tetrahydro-pyrido[4,3-d]-pyrimidin-2-yl]-2-fluoro-benzamide,

[14] thiophene-2-carboxylic acid [6-(3,4,5-trimethoxy-benzoylamino)-5,6,7,8-tetrahydro-quinazolin-2-yl]-amide,

[15] naphthalene-1-carboxylic acid [6-(3-methyl-5-phenyl-isoxazole-4-carbonyl)-5,6,7,8-tetrahydro-pyrido[4,3-d]pyrimidin-2-yl]-amide,

[16] 3-chloro-N-{6-[2-(5-methyl-2-phenyl-thiazol-4-yl)-acetyl]-5,6,7,8-tetrahydro-pyrido[4,3-d]pyrimidin-2-yl}-benzamide,

[17] N-[6-(4-chloro-2,5-dimethyl-benzenesulfonyl)-5,6,7,8-tetrahydro-pyrido[4,3-d]pyrimidin-2-yl]-2-trifluoromethyl-benzamide,

[18] N-[6-(1-benzenesulfonyl-1H-indole-2-carbonyl)-5,6,7,8-tetrahydro-pyrido[4,3-d]pyrimidin-2-yl]-3-methoxy-benzamide,

[20] N-[6-(5-methyl-1-phenyl-1H-pyrazole-4-sulfonyl)-5,6,7,8-tetrahydro-pyrido[4,3-d]pyrimidin-2-yl]-2-trifluoromethyl-benzamide,

[21] N-[6-(3-chloro-2-methyl-benzenesulfonyl)-5,6,7,8-tetrahydro-pyrido[4,3-(d)]pyrimidin-2-yl]-3-fluoro-benzamide,

[22] 3,5-dichloro-N-[6-(3,5-dimethyl-isoxazole-4-carbonyl)-5,6,7,8-tetrahydro-pyrido[4,3-d]pyrimidin-2-yl]-benzamide,

[23] thiophene-2-carboxylic acid [6-(4-trifluoromethoxy-benzenesulfonylamino)-5,6,7,8-tetrahydro-quinazolin-2-yl]-amide,

[25] N-[6-(furan-2-carbonyl)-5,6,7,8-tetrahydro-pyrido[4,3-d]pyrimidin-2-yl]-3-methoxy-benzamide,

[26] N-{6-[4-(2,3-dihydro-indol-1-yl)-4-oxo-butyryl]-5,6,7,8-tetrahydro-pyrido[4,3-d]pyrimidin-2-yl}-3-methyl-benzamide,

[27] N-{6-[2-(4-methyl-cyclohexyl)-acetyl]-5,6,7,8-tetrahydro-pyrido[4,3-d]pyrimidin-2-yl}-2-trifluoromethyl-benzamide,

[28] 3,4-difluoro-N-[6-(6-phenoxy-pyridine-3-carbonyl)-5,6,7,8-tetrahydro-pyrido[4,3-d]pyrimidin-2-yl]-benzamide,

[29] 4-tert-butyl-N-[6-(2-phenyl-thiazole-4-carbonyl)-5,6,7,8-tetrahydro-pyrido[4,3-d]pyrimidin-2-yl]-benzamide,

[30] 3,5-dichloro-N-[6-(2-trifluoromethyl-benzenesulfonyl)-5,6,7,8-tetrahydro-pyrido[4,3-d]pyrimidin-2-yl]-benzamide,

[31] thiophene-2-carboxylic acid [6-(3-bromo-benzenesulfonylamino)-5,6,7,8-tetrahydro-quinazolin-2-yl]-amide,

[32] N-[6-(2-chloro-pyridine-4-carbonyl)-5,6,7,8-tetrahydro-pyrido[4,3-d]pyrimidin-2-yl]-3-methoxy-benzamide,

[33] 4-fluoro-N-[6-(2-methanesulfonyl-benzenesulfonylamino)-5,6,7,8-tetrahydro-quinazolin-2-yl]-benzamide,

[35] N-(6-dimethylsulfamoyl-5,6,7,8-tetrahydro-pyrido[4,3-(d)]pyrimidin-2-yl)-3-fluoro-benzamide,

[36] 3-fluoro-N-{6-[2-(4-trifluoromethyl-phenyl)-acetyl]-5,6,7,8-tetrahydro-pyrido[4,3-(d)]pyrimidin-2-yl}-benzamide,

[37] N-{6-[2-(1,3-dioxo-1,3-dihydro-isoindol-2-yl)-acetyl]-5,6,7,8-tetrahydro-pyrido[4,3-(d)]pyrimidin-2-yl}-2-trifluoromethyl-benzamide,

[38] thiophene-2-carboxylic acid {6-[4-(4-chloro-2-methyl-phenoxy)-butyrylamino]-5,6,7,8-tetrahydro-quinazolin-2-yl}-amide,

[39] N-[6-(butane-1-sulfonyl)-5,6,7,8-tetrahydro-pyrido[4,3-(d)]pyrimidin-2-yl]-3-fluoro-benzamide,

[40] 2-methoxy-N-[6-(2-propyl-pentanoyl)-5,6,7,8-tetrahydro-pyrido[4,3-d]pyrimidin-2-yl]-benzamide,

[41] N-[6-(4,5-dichloro-thiophene-2-sulfonylamino)-5,6,7,8-tetrahydro-quinazolin-2-yl]-4-fluoro-benzamide,

[42] 4-chloro-N-[6-(2-trifluoromethyl-benzenesulfonyl)-5,6,7,8-tetrahydro-pyrido[4,3-d]pyrimidin-2-yl]-benzamide,

[43] thiophene-2-carboxylic acid [6-(4-methoxy-benzenesulfonylamino)-5,6,7,8-tetrahydro-quinazolin-2-yl]-amide,

[44] 5-[2-(3,4-difluoro-benzoylamino)-7,8-dihydro-5H-pyrido[4,3-(d)]pyrimidin-6-yl]-5-oxo-valeric acid methyl ester,

[45] N-[6-(benzo[b]thiophene-3-carbonyl)-5,6,7,8-tetrahydro-pyrido[4,3-d]pyrimidin-2-yl]-4-chloro-benzamide,

[46] N-[6-(5-bromo-2-methoxy-benzenesulfonylamino)-5,6,7,8-tetrahydro-quinazolin-2-yl]-4-fluoro-benzamide,

[47] 4-fluoro-N-[6-(4-fluoro-benzenesulfonylamino)-5,6,7,8-tetrahydro-quinazolin-2-yl]-benzamide,

[48] N-{6-[2-(1H-indol-3-yl)-2-oxo-acetyl]-5,6,7,8-tetrahydro-pyrido[4,3-d]pyrimidin-2-yl}-2-trifluoromethyl-benzamide,
[49] 5-tert-butyl-2-methyl-furan-3-carboxylic acid {2-[(thiophene-2-carbonyl)-amino]-5,6,7,8-tetrahydro-quinazolin-6-yl}-amide,
[50] N-[6-(2,5-dimethoxy-benzenesulfonyl)-5,6,7,8-tetrahydro-pyrido[4,3-d]pyrimidin-2-yl]-3-methoxy-benzamide,
[51] benzoic acid 2-{2-[(thiophene-2-carbonyl)-amino]-5,6,7,8-tetrahydro-quinazolin-6-ylcarbamoyl}-benzyl ester,
[52] 3,4-difluoro-N-(6-hexanoyl-5,6,7,8-tetrahydro-pyrido[4,3-(d)]pyrimidin-2-yl)-benzamide,
[53] 4-ethyl-N-[6-(tetrahydro-furan-2-carbonyl)-5,6,7,8-tetrahydro-pyrido[4,3-d]pyrimidin-2-yl]-benzamide,
[54] N-[6-(2-chloro-benzenesulfonyl)-5,6,7,8-tetrahydro-pyrido[4,3-d]pyrimidin-2-yl]-3-fluoro-benzamide,
[55] 4-tert-butyl-N-[6-(5-tert-butyl-2-methyl-2H-pyrazole-3-carbonyl)-5,6,7,8-tetrahydro-pyrido[4,3-d]pyrimidin-2-yl]-benzamide,
[56] 3-methoxy-N-[6-(4-methoxy-benzenesulfonyl) -5,6,7,8-tetrahydro-pyrido[4,3-d]pyrimidin-2-yl]-benzamide,
[57] {2-[2-(3,4-difluoro-benzoylamino)-7,8-dihydro-5H-pyrido[4,3-d]pyrimidin-6-yl]-2-oxo-1-phenyl-ethyl}-carbamic acid benzyl ester,
[58] 5-phenyl-oxazole-4-carboxylic acid {2-[(thiophene-2-carbonyl)-amino]-5,6,7,8-tetrahydro-quinazolin-6-yl}-amide,
[59] 4-chloro-N-(6-dimethylsulfamoyl-5,6,7,8-tetrahydro-pyrido[4,3-d]pyrimidin-2-yl)-benzamide,
[60] 4-tert-butyl-N-[6-(2-fluoro-benzenesulfonyl)-5,6,7,8-tetrahydro-pyrido[4,3-d]pyrimidin-2-yl]-benzamide,
[61] 4-chloro-N-[6-(3-cyclopentyl-propionyl)-5,6,7,8-tetrahydro-pyrido[4,3-d]pyrimidin-2-yl]-benzamide,
[62] 4-chloro-N-[6-(4-phenyl-butyryl)-5,6,7,8-tetrahydro-pyrido[4,3-d]pyrimidin-2-yl]-benzamide,
[63] 4-tert-butyl-N-[6-(5-methyl-2-phenyl-2H-[1,2,3]triazole-4-carbonyl)-5,6,7,8-tetrahydro-pyrido[4,3-d]pyrimidin-2-yl]-benzamide,
[64] 2-chloro-N-{2-[(thiophene-2-carbonyl)-amino]-5,6,7,8-tetrahydro-quinazolin-6-yl}-isonicotinamide,
[66] N-[6-(5-chloro-thiophene-2-sulfonyl)-5,6,7,8-tetrahydro-pyrido[4,3-d]pyrimidin-2-yl]-3-fluoro-benzamide,
[67] N-[6-(4-diethylamino-benzoyl)-5,6,7,8-tetrahydro-pyrido[4,3-d]pyrimidin-2-yl]-3-methoxy-benzamide,
[68] N-[6-(2,4-dimethyl-thiazole-5-sulfonyl)-5,6,7,8-tetrahydro-pyrido[4,3-d]pyrimidin-2-yl]-3-methyl-benzamide,
[69] 4-chloro-N-[6-naphthalene-2-carbonyl)-5,6,7,8-tetrahydro-pyrido[4,3-d]pyrimidin-2-yl]-benzamide,
[70] N-[6-(2,4-difluoro-benzenesulfonyl)-5,6,7,8-tetrahydro-pyrido[4,3-d]pyrimidin-2-yl]-2-methoxy-benzamide,
[71] 3,4-dichloro-N-[6-(4-chloro-benzenesulfonyl)-5,6,7,8-tetrahydro-pyrido[4,3-d]pyrimidin-2-yl]-benzamide,
[72] 3,4-difluoro-N-[6-(thiophene-2-sulfonyl)-5,6,7,8-tetrahydro-pyrido[4,3-d]pyrimidin-2-yl]-benzamide,
[74] 4-ethyl-N-[6-(4-pyrazol-1-yl-benzoyl)-5,6,7,8-tetrahydro-pyrido[4,3-d]pyrimidin-2-yl]-benzamide,
[75] N-[6-(7,7-dimethyl-2-oxo-bicyclo[2.2.1]hept-1-ylmethanesulfonylamino)-5,6,7,8-tetrahydro-quinazolin-2-yl]-butyramide,
[76] 5-oxo-5-phenyl-valeric acid (2-butyrylamino-5,6,7,8-tetrahydro-quinazolin-6-yl)-amide,
[77] 3-[2-(4-chloro-benzoylamino)-7,8-dihydro-5H-pyrido[4,3-d]pyrimidin-6-yl]-3-oxo-propionic acid methyl ester,
[78] N-{6-[5-(4-chloro-phenyl)-2-methyl-furan-3-carbonyl]-5,6,7,8-tetrahydro-pyrido[4,3-d]pyrimidin-2-yl}-2-methoxy-benzamide,
[79] 4-chloro-N-[6-(2,4-dimethyl-thiazole-5-sulfonyl)-5,6,7,8-tetrahydro-pyrido[4,3-d]pyrimidin-2-yl]-benzamide,
[80] N-[6-(2,3-difluoro-benzoyl)-5,6,7,8-tetrahydro-pyrido[4,3-d]pyrimidin-2-yl]-3-methoxy-benzamide,
[81] 4-chloro-N-{6-[2-(2-methoxy-ethoxy)-acetyl]-5,6,7,8-tetrahydro-pyrido[4,3-d]pyrimidin-2-yl}-benzamide,
[82] 2-[2-(2-ethoxy-benzoylamino)-7,8-dihydro-5H-pyrido[4,3-d]pyrimidine-6-sulfonyl]-benzoic acid methyl ester,
[83] 4-tert-butyl-N-[6-(4-nitro-benzenesulfonyl)-5,6,7,8-tetrahydro-pyrido[4,3-d]pyrimidin-2-yl]-benzamide,
[86] N-[6-(5-chloro-thiophene-2-sulfonyl)-5,6,7,8-tetrahydro-pyrido[4,3-d]pyrimidin-2-yl]-2-methoxy-benzamide,
[87] 4-fluoro-N-[6-(furan-2-carbonyl)-5,6,7,8-tetrahydro-pyrido[4,3-d]pyrimidin-2-yl]-benzamide,
[88] 4-{2-[(thiophene-2-carbonyl)-amino]-5,6,7,8-tetrahydro-quinazolin-6-ylcarbamoyl}-piperidine-1-carboxylic acid tert-butyl ester,
[89] 1-(4-chloro-phenyl)-cyclopropanecarboxylic acid (2-butyrylamino-5,6,7,8-tetrahydro-quinazolin-6-yl)-amide,
[90] N-(6-ethanesulfonyl-5,6,7,8-tetrahydro-pyrido[4,3-d]pyrimidin-2-yl)-3-methoxy-benzamide,
[91] 5-methyl-thiophene-2-carboxylic acid (2-butyrylamino-5,6,7,8-tetrahydro-quinazolin-6-yl)-amide,
[92] 4-tert-butyl-N-[6-(4-methyl-3-nitro-benzoyl)-5,6,7,8-tetrahydro-pyrido[4,3-d]pyrimidin-2-yl]-benzamide,
[94] 4-fluoro-N-[6-(3-phenyl-propionylamino)-5,6,7,8-tetrahydro-quinazolin-2-yl]-benzamide,
[95] 3,4-dichloro-N-[6-(2,4,6-trimethyl-benzenesulfonyl)-5,6,7,8-tetrahydro-pyrido[4,3-d]pyrimidin-2-yl]-benzamide,
[96] N-[6-(4-methyl-3,4-dihydro-2H-benzo[1,4]oxazine-7-sulfonyl)-5,6,7,8-tetrahydro-pyrido[4,3-d]pyrimidin-2-yl]-nicotinamide,
[97] thiophene-2-carboxylic acid [6-(3,5-difluoro-benzoylamino)-5,6,7,8-tetrahydro-quinazolin-2-yl]-amide,
[98] N-[6-(2,4-difluoro-benzenesulfonylamino)-5,6,7,8-tetrahydro-quinazolin-2-yl]-butyramide,
[99] thiophene-2-carboxylic acid [6-(2,3,5,6-tetramethyl-benzenesulfonyl)-5,6,7,8-tetrahydro-pyrido[4,3-d]pyrimidin-2-yl]-amide,
[101] N-[6-(3,4-dichloro-benzoyl)-5,6,7,8-tetrahydro-pyrido[4,3-d]pyrimidin-2-yl]-4-ethyl-benzamide,
[102] N-[6-(7,7-dimethyl-2-oxo-bicyclo[2.2.1]hept-1-ylmethanesulfonyl)-5,6,7,8-tetrahydro-pyrido[4,3-d]pyrimidin-2-yl]-3-fluoro-benzamide,
[103] N-[6-(6-fluoro-4H-benzo[1,3]dioxin-8-carbonyl)-5,6,7,8-tetrahydro-pyrido[4,3-d]pyrimidin-2-yl]-2-trifluoromethyl-benzamide,
[104] [5-(2-butyrylamino-5,6,7,8-tetrahydro-quinazolin-6-ylcarbamoyl)-pentyl]-carbamic acid benzyl ester,
[105] 2-ethoxy-N-[6-(4-oxo-pentanoyl)-5,6,7,8-tetrahydro-pyrido[4,3-d]pyrimidin-2-yl]-benzamide,
[106] naphthalene-1-carboxylic acid [6-(propane-1-sulfonyl)-5,6,7,8-tetrahydro-pyrido[4,3-d]pyrimidin-2-yl]-amide,

[107] N-[6-(5-fluoro-2-methyl-benzenesulfonyl)-5,6,7,8-tetrahydro-pyrido[4,3-d]pyrimidin-2-yl]-4-methyl-benzamide,

[109] 3-chloro-N-[6-(2-methyl-benzoyl)-5,6,7,8-tetrahydro-pyrido[4,3-d]pyrimidin-2-yl]-benzamide,

[110] thiophene-2-carboxylic acid [6-(3-chloro-benzo[b]thiophene-2-carbonyl)-5,6,7,8-tetrahydro-pyrido[4,3-d]pyrimidin-2-yl]-amide,

[112] thiophene-2-carboxylic acid [6-(2-cyclopentyl-acetylamino)-5,6,7,8-tetrahydro-quinazolin-2-yl]-amide,

[113] N-[6-(3,4-dichloro-benzoyl)-5,6,7,8-tetrahydro-pyrido[4,3-d]pyrimidin-2-yl]-2-fluoro-benzamide,

[114] N-[6-(2-chloro-benzenesulfonyl)-5,6,7,8-tetrahydro-pyrido[4,3-d]pyrimidin-2-yl]-4-ethyl-benzamide,

[115] thiophene-2-carboxylic acid [6-(4-bromo-3-methyl-benzoylamino)-5,6,7,8-tetrahydro-quinazolin-2-yl]-amide,

[116] 3-methyl-N-[6-(toluene-3-sulfonyl)-5,6,7,8-tetrahydro-pyrido[4,3-d]pyrimidin-2-yl]-benzamide,

[117] naphthalene-1-carboxylic acid [6-(5-chloro-thiophene-2-sulfonyl)-5,6,7,8-tetrahydro-pyrido[4,3-d]pyrimidin-2-yl]-amide,

[118] N-(2-butyrylamino-5,6,7,8-tetrahydro-quinazolin-6-yl)-2,6-difluoro-benzamide,

[119] 3-chloro-N-[6-(3,4-dimethoxy-benzoyl)-5,6,7,8-tetrahydro-pyrido[4,3-d]pyrimidin-2-yl]-benzamide,

[120] N-[6-(3-chloro-benzo[b]thiophene-2-carbonyl)-5,6,7,8-tetrahydro-pyrido[4,3-d]pyrimidin-2-yl]-benzamide,

[121] 4-ethyl-N-[6-(thiophene-3-sulfonyl)-5,6,7,8-tetrahydro-pyrido[4,3-d]pyrimidin-2-yl]-benzamide,

[123] 2-ethoxy-N-[6-(2-ethylsulfanyl-pyridine-3-carbonyl)-5,6,7,8-tetrahydro-pyrido[4,3-d]pyrimidin-2-yl]-benzamide,

[124] 3-[2-(3-chloro-benzoylamino)-7,8-dihydro-5H-pyrido[4,3-d]pyrimidin-6-yl]-3-oxo-propionic acid ethyl ester,

[125] N-[6-(3-bromo-benzenesulfonyl)-5,6,7,8-tetrahydro-pyrido[4,3-d]pyrimidin-2-yl]-3-chloro-benzamide,

[126] 3,4-dichloro-N-{6-[2-(4-chloro-phenyl)-acetyl]-5,6,7,8-tetrahydro-pyrido[4,3-d]pyrimidin-2-yl}-benzamide,

[127] 3-chloro-N-[6-(2-chloro-6-fluoro-benzoyl)-5,6,7,8-tetrahydro-pyrido[4,3-d]pyrimidin-2-yl]-benzamide,

[128] 4-fluoro-N-(6-hexanoylamino-5,6,7,8-tetrahydro-quinazolin-2-yl)-benzamide,

[129] N-[6-(5-bromo-2-methoxy-benzenesulfonyl)-5,6,7,8-tetrahydro-pyrido[4,3-d]pyrimidin-2-yl]-3-methoxy-benzamide,

[132] N-[6-(3-cyclopentyl-propionyl)-5,6,7,8-tetrahydro-pyrido[4,3-d]pyrimidin-2-yl]-isonicotinamide,

[133] 5-benzyl-furan-2-carboxylic acid (2-butyrylamino-5,6,7,8-tetrahydro-quinazolin-6-yl)-amide

[134] 3,4-dichloro-N-[6-(4-trifluoromethoxy-benzenesulfonyl)-5,6,7,8-tetrahydro-pyrido[4,3-d]pyrimidin-2-yl]-benzamide,

[135] [(2-butyrylamino-5,6,7,8-tetrahydro-quinazolin-6-ylcarbamoyl)-phenyl-methyl]-carbamic acid benzyl ester,

[136] N-[6-(3,4-dimethoxy-benzenesulfonyl)-5,6,7,8-tetrahydro-pyrido[4,3-d]pyrimidin-2-yl]-4-fluoro-benzamide,

[137] 2-fluoro-N-[6-(2-methyl-5-phenyl-furan-3-carbonyl)-5,6,7,8-tetrahydro-pyrido[4,3-d]pyrimidin-2-yl]-benzamide,

[138] thiophene-2-carboxylic acid (6-pent-4-enoylamino-5,6,7,8-tetrahydro-quinazolin-2-yl)-amide,

[139] (2-methyl-1-{2-[(thiophene-2-carbonyl)-amino]-5,6,7,8-tetrahydro-quinazolin-6-ylcarbamoyl}-propyl)-carbamic acid 9H-fluoren-9-ylmethyl ester,

[140] (5-{2-[(thiophene-2-carbonyl)-amino]-5,6,7,8-tetrahydro-quinazolin-6-ylcarbamoyl}-pentyl)-carbamic acid tert-butyl ester,

[141] 3-fluoro-N-[6-(1,2,3,4-tetrahydro-naphthalene-2-carbonyl)-5,6,7,8-tetrahydro-pyrido[4,3-d]pyrimidin-2-yl]-benzamide,

[142] 4-chloro-N-{6-[2-(2,5-dioxo-imidazolidin-4-yl)-acetyl]-5,6,7,8-tetrahydro-pyrido[4,3-d]pyrimidin-2-yl}-benzamide,

[143] 3-fluoro-N-[6-(toluene-4-sulfonyl)-5,6,7,8-tetrahydro-pyrido[4,3-d]pyrimidin-2-yl]-benzamide,

[144] 3,5-dichloro-N-[6-(4-thiophen-2-yl-benzoyl)-5,6,7,8-tetrahydro-pyrido[4,3-d]pyrimidin-2-yl]-benzamide,

[145] N-[6-(3-chloro-thiophene-2-carbonyl)-5,6,7,8-tetrahydro-pyrido[4,3-d]pyrimidin-2-yl]-2-ethoxy-benzamide,

[146] N-[6-(toluene-3-sulfonylamino)-5,6,7,8-tetrahydro-quinazolin-2-yl]-butyramide,

[147] thiophene-2-carboxylic acid {6-[2-(2,2,2-trifluoro-acetyl)-1,2,3,4-tetrahydro-isoquinoline-7-sulfonylamino]-5,6,7,8-tetrahydro-quinazolin-2-yl}-amide,

[148] 4-methyl-N-[6-(4-trifluoromethylsulfanyl-benzoyl)-5,6,7,8-tetrahydro-pyrido[4,3-d]pyrimidin-2-yl]-benzamide,

[149] (2-{2-[(thiophene-2-carbonyl)-amino]-5,6,7,8-tetrahydro-quinazolin-6-ylcarbamoyl}-ethyl)-carbamic acid tert-butyl ester,

[150] 2-fluoro-N-[6-(2-methyl-5-nitro-benzenesulfonyl)-5,6,7,8-tetrahydro-pyrido[4,3-d]pyrimidin-2-yl]-benzamide,

[151] N-[6-(4-methoxy-benzenesulfonylamino)-5,6,7,8-tetrahydro-quinazolin-2-yl]-butyramide,

[152] 4-chloro-N-[6-(2,4-difluoro-benzoyl)-5,6,7,8-tetrahydro-pyrido[4,3-d]pyrimidin-2-yl]-benzamide

[153] 4-methyl-N-(6-pent-4-enoyl-5,6,7,8-tetrahydro-pyrido[4,3-d]pyrimidin-2-yl)-benzamide,

[154] naphthalene-1-carboxylic acid [6-(3-fluoro-4-methyl-benzoyl)-5,6,7,8-tetrahydro-pyrido[4,3-d]pyrimidin-2-yl]-amide,

[155] N-{6-[2-(4-trifluoromethyl-phenyl)-acetyl]-5,6,7,8-tetrahydro-pyrido[4,3-d]pyrimidin-2-yl}-benzamide,

[156] N-[6-(3,4-dichloro-benzoyl)-5,6,7,8-tetrahydro-pyrido[4,3-d]pyrimidin-2-yl]-nicotinamide,

[157] 4-ethyl-N-{6-[2-(2,2,2-trifluoro-acetyl)-1,2,3,4-tetrahydro-isoquinoline-7-sulfonyl]-5,6,7,8-tetrahydro-pyrido[4,3-d]pyrimidin-2-yl}-benzamide,

[158] 2-methoxy-N-[6-(4-methoxy-2,3,6-trimethyl-benzenesulfonyl)-5,6,7,8-tetrahydro-pyrido[4,3-d]pyrimidin-2-yl]-benzamide,

[159] 4-ethyl-N-[6-(2-methoxy-acetyl)-5,6,7,8-tetrahydro-pyrido[4,3-d]pyrimidin-2-yl]-benzamide,

[160] 4-fluoro-N-[6-(propane-1-sulfonylamino)-5,6,7,8-tetrahydro-quinazolin-2-yl]-benzamide,

[162] N-[6-(7,7-dimethyl-2-oxo-bicyclo[2.2.1]hept-1-yl-methanesulfonylamino)-5,6,7,8-tetrahydro-quinazolin-2-yl]-butyramide,

[163] N-{6-[2-(2,5-dimethyl-phenyl)-acetylamino]-5,6,7,8-tetrahydro-quinazolin-2-yl}-4-fluoro-benzamide,

[165] thiophene-2-carboxylic acid (6-phenylmethanesulfonylamino-5,6,7,8-tetrahydro-quinazolin-2-yl)-amide,

[166] N-[6-(3,4-dimethoxy-benzenesulfonylamino)-5,6,7,8-tetrahydro-quinazolin-2-yl]-butyramide,

[167] N-{6-[4-(1,1-dimethyl-propyl)-benzenesulfonylamino]-5,6,7,8-tetrahydro-quinazolin-2-yl}-butyramide,

[168] N-(2-butyrylamino-5,6,7,8-tetrahydro-quinazolin-6-yl)-3-(3-trifluoromethyl-phenyl)-acrylamide,

[169] N-[6-(butane-1-sulfonylamino)-5,6,7,8-tetrahydro-quinazolin-2-yl]-4-fluoro-benzamide,

[170] naphthalene-1-carboxylic acid (6-acetyl-5,6,7,8-tetrahydro-pyrido[4,3-d]pyrimidin-2-yl)-amide,

[171] 3,5-dichloro-N-[6-(3-diethylcarbamoyl-propionyl)-5,6,7,8-tetrahydro-pyrido[4,3-d]pyrimidin-2-yl]-benzamide,

[172] 4-ethyl-N-[6-(4-methoxy-benzenesulfonyl)-5,6,7,8-tetrahydro-pyrido[4,3-d]pyrimidin-2-yl]-benzamide,

[173] 4-ethyl-N-[6-(quinoline-6-carbonyl)-5,6,7,8-tetrahydro-pyrido[4,3-d]pyrimidin-2-yl]-benzamide,

[174] N-[6-(2-cyclopropyl-acetyl)-5,6,7,8-tetrahydro-pyrido[4,3-d]pyrimidin-2-yl]-2-fluoro-benzamide,

[175] N-[6-(2H-chromene-3-carbonyl)-5,6,7,8-tetrahydro-pyrido[4,3-d]pyrimidin-2-yl]-3,4-difluoro-benzamide,

[176] N-{6-[2-(4-chloro-phenyl)-propionyl]-5,6,7,8-tetrahydro-pyrido[4,3-d]pyrimidin-2-yl}-benzamide,

[177] thiophene-2-carboxylic acid [6-(2-naphthalen-1-yl-acetylamino)-5,6,7,8-tetrahydro-quinazolin-2-yl]-amide,

[178] 4-fluoro-N-(6-phenylmethanesulfonyl-5,6,7,8-tetrahydro-pyrido[4,3-d]pyrimidin-2-yl)-benzamide,

[180] thiophene-2-carboxylic acid [6-(2,5-dichloro-thiophene-3-sulfonylamino)-5,6,7,8-tetrahydro-quinazolin-2-yl]-amide,

[181] {5-[2-(4-fluoro-benzoylamino)-5,6,7,8-tetrahydro-quinazolin-6-ylcarbamoyl]-pentyl}-carbamic acid benzyl ester,

[182] N-[6-(2,5-dimethyl-2H-pyrazole-3-carbonyl)-5,6,7,8-tetrahydro-pyrido[4,3-d]pyrimidin-2-yl]-4-ethyl-benzamide,

[183] naphthalene-1-carboxylic acid [6-(3-fluoro-benzoyl)-5,6,7,8-tetrahydro-pyrido[4,3-d]pyrimidin-2-yl]-amide,

[184] N-[6-(benzo[b]thiophene-3-carbonyl)-5,6,7,8-tetrahydro-pyrido[4,3-d]pyrimidin-2-yl]-4-tert-butyl-benzamide,

[185] 4-fluoro-N-[6-(4-methoxy-benzenesulfonyl)-5,6,7,8-tetrahydro-pyrido[4,3-d]pyrimidin-2-yl]-benzamide,

[186] 4-tert-butyl-N-[6-(2,3-dihydro-benzo[1,4]dioxin-6-sulfonyl)-5,6,7,8-tetrahydro-pyrido[4,3-d]pyrimidin-2-yl]-benzamide,

[187] 3-chloro-N-{6-[2-(2,6-dichloro-phenyl)-acetyl]-5,6,7,8-tetrahydro-pyrido[4,3-d]pyrimidin-2-yl}-benzamide,

[188] thiophene-2-carboxylic acid [6-(2,3-dihydro-benzo[1,4]dioxin-6-sulfonylamino)-5,6,7,8-tetrahydro-quinazolin-2-yl]-amide,

[189] N-{6-[2-(3-chloro-phenoxy)-acetyl]-5,6,7,8-tetrahydro-pyrido[4,3-d]pyrimidin-2-yl}-4-methyl-benzamide,

[190] N-[6-(5-phenyl-pentanoyl)-5,6,7,8-tetrahydro-pyrido[4,3-d]pyrimidin-2-yl]-benzamide,

[191] 4-ethyl-N-[6-(2-ethyl-butyryl)-5,6,7,8-tetrahydro-pyrido[4,3-d]pyrimidin-2-yl]-benzamide,

[192] 3,5-dichloro-N-[6-(4-trifluoromethoxy-benzoyl)-5,6,7,8-tetrahydro-pyrido[4,3-d]pyrimidin-2-yl]-benzamide,

[193] naphthalene-1-carboxylic acid [6-(4-methyl-octanoyl)-5,6,7,8-tetrahydro-pyrido[4,3-d]pyrimidin-2-yl]-amide,

[194] 4-[2-(4-fluoro-benzoylamino)-5,6,7,8-tetrahydro-quinazolin-6-ylcarbamoyl]-piperidine-1-carboxylic acid tert-butyl ester,

[195] N-[6-(2-benzyloxy-acetyl)-5,6,7,8-tetrahydro-pyrido[4,3-d]pyrimidin-2-yl]-2-methoxy-benzamide,

[196] N-[6-(2-trifluoromethyl-benzenesulfonylamino)-5,6,7,8-tetrahydro-quinazolin-2-yl]-butyramide,

[197] N-[2-(4-fluoro-benzoylamino)-5,6,7,8-tetrahydro-quinazolin-6-yl]-2-methyl-6-trifluoromethyl-nicotinamide,

[198] N-[6-(3-cyano-benzoyl)-5,6,7,8-tetrahydro-pyrido[4,3-d]pyrimidin-2-yl]-2-trifluoromethyl-benzamide,

[199] 3-methoxy-N-[6-(3-trifluoromethoxy-benzoyl)-5,6,7,8-tetrahydro-pyrido[4,3-d]pyrimidin-2-yl]-benzamide,

[200] N-(6-butyryl-5,6,7,8-tetrahydro-pyrido[4,3-d]pyrimidin-2-yl)-2-fluoro-benzamide,

[201] N-(6-benzenesulfonylamino-5,6,7,8-tetrahydro-quinazolin-2-yl)-4-fluoro-benzamide,

[202] N-[6-(5-chloro-thiophene-2-sulfonylamino)-5,6,7,8-tetrahydro-quinazolin-2-yl]-4-fluoro-benzamide,

[203] naphthalene-1-carboxylic acid (6-hexanoyl-5,6,7,8-tetrahydro-pyrido[4,3-d]pyrimidin-2-yl)-amide,

[204] N-(6-propionyl-5,6,7,8-tetrahydro-pyrido[4,3-d]pyrimidin-2-yl)-2-trifluoromethyl-benzamide,

[205] N-[6-(2-ethyl-butyryl)-5,6,7,8-tetrahydro-pyrido[4,3-d]pyrimidin-2-yl]-4-methyl-benzamide,

[206] 2-fluoro-N-[6-(3-trifluoromethyl-benzenesulfonyl)-5,6,7,8-tetrahydro-pyrido[4,3-d]pyrimidin-2-yl]-benzamide,

[207] 5-benzyl-furan-2-carboxylic acid {2-[(thiophene-2-carbonyl)-amino]-5,6,7,8-tetrahydro-quinazolin-6-yl}-amide,

[208] thiophene-2-carboxylic acid {6-[2-(2,5-dimethyl-phenyl)-acetylamino]-5,6,7,8-tetrahydro-quinazolin-2-yl}-amide,

[210] 4-fluoro-N-[6-(propane-1-sulfonyl)-5,6,7,8-tetrahydro-pyrido[4,3-d]pyrimidin-2-yl]-benzamide,

[211] 2-[2-(3-fluoro-benzoylamino)-7,8-dihydro-5H-pyrido[4,3-d]pyrimidine-6-sulfonyl]-benzoic acid methyl ester,

[212] 3,5-dichloro-N-[6-(5-[1,2]dithiolan-3-yl-pentanoyl)-5,6,7,8-tetrahydro-pyrido[4,3-d]pyrimidin-2-yl]-benzamide,

[213] thiophene-2-carboxylic acid [6-(2-phenoxy-butyrylamino)-5,6,7,8-tetrahydro-quinazolin-2-yl]-amide,

[214] thiophene-2-carboxylic acid {6-[2-(4-methoxyphenyl)-acetylamino]-5,6,7,8-tetrahydro-quinazolin-2-yl}-amide,

[215] N-(6-cyclohexanecarboxylic-5,6,7,8-tetrahydro-pyrido[4,3-d]pyrimidin-2-yl)-2-trifluoromethyl-benzamide,

[216] N-[6-(2,4-dimethyl-thiazole-5-sulfonyl)-5,6,7,8-tetrahydro-pyrido[4,3-d]pyrimidin-2-yl]-2-trifluoromethyl-benzamide,

[217] 2-thiophen-2-yl-thiazole-4-carboxylic acid {2-[(thiophene-2-carbonyl)-amino]-5,6,7,8-tetrahydro-quinazolin-6-yl}-amide,

[219] thiophene-2-carboxylic acid {6-[3-(3-trifluoromethyl-phenyl)-acryloylamino]-5,6,7,8-tetrahydro-quinazolin-2-yl}-amide,

[220] thiophene-2-carboxylic acid [6-(5-phenyl-pentanoylamino)-5,6,7,8-tetrahydro-quinazolin-2-yl]-amide,

[221] thiophene-2-carboxylic acid [6-(2-chloro-5-trifluoromethyl-benzoylamino)-5,6,7,8-tetrahydro-quinazolin-2-yl]-amide,
[222] 4-fluoro-N-[6-(2,3,5,6-tetramethyl-benzenesulfonylamino)-5,6,7,8-tetrahydro-quinazolin-2-yl]-benzamide,
[223] 4-fluoro-N-[6-(4-methyl-octanoyl)-5,6,7,8-tetrahydro-pyrido[4,3-d]pyrimidin-2-yl]-benzamide,
[224] 2-{2-[(thiophene-2-carbonyl)-amino]-5,6,7,8-tetrahydro-quinazolin-6-ylsulfamoyl}-benzoic acid methyl ester,
[225] [(3-methyl-1-{2-[(thiophene-2-carbonyl)-amino]-5,6,7,8-tetrahydro-quinazolin-6-ylcarbamoyl}-butylcarbamoyl)-methyl]-carbamic acid benzyl ester,
[226] 3-chloro-N-(6-pentanoyl-5,6,7,8-tetrahydro-pyrido[4,3-d]pyrimidin-2-yl)-benzamide,
[227] 4-fluoro-N-[6-(5-oxo-5-phenyl-pentanoylamino)-5,6,7,8-tetrahydro-quinazolin-2-yl]-benzamide,
[228] thiophene-2-carboxylic acid [6-(3-phenyl-acryloylamino)-5,6,7,8-tetrahydro-quinazolin-2-yl]-amide,
[229] N-[6-(5-[1,2]dithiolan-3-yl-pentanoylamino)-5,6,7,8-tetrahydro-quinazolin-2-yl]-4-fluoro-benzamide,
[230] benzoic acid 2-(2-{2-[(thiophene-2-carbonyl)-amino]-5,6,7,8-tetrahydro-quinazolin-6-ylcarbamoyl}-ethyl)-phenyl ester,
[231] 4-fluoro-N-[6-(2-methyl-5-nitro-benzenesulfonylamino)-5,6,7,8-tetrahydro-quinazolin-2-yl]-benzamide,
[232] 4-chloro-N-[6-(2-phenoxy-acetyl)-5,6,7,8-tetrahydro-pyrido[4,3-d]pyrimidin-2-yl]-benzamide,
[234] N-[6-(5-bromo-thiophene-2-carbonyl)-5,6,7,8-tetrahydro-pyrido[4,3-d]pyrimidin-2-yl]-2-fluoro-benzamide,
[235] 4-fluoro-N-[6-(5-fluoro-2-methyl-benzenesulfonylamino)-5,6,7,8-tetrahydro-quinazolin-2-yl]-benzamide,
[236] N-[6-(4-acetylamino-benzenesulfonylamino)-5,6,7,8-tetrahydro-quinazolin-2-yl]-4-fluoro-benzamide,
[237] thiophene-2-carboxylic acid [6-(2-trifluoromethyl-benzoylamino)-5,6,7,8-tetrahydro-quinazolin-2-yl]-amide,
[238] 3,4-difluoro-N-[6-(quinoline-6-carbonyl)-5,6,7,8-tetrahydro-pyrido[4,3-d]pyrimidin-2-yl]-benzamide,
[239] {1-[2-(4-fluoro-benzoylamino)-5,6,7,8-tetrahydro-quinazolin-6-ylcarbamoyl]-2-phenyl-ethyl}-carbamic acid tert-butyl ester,
[240] thiophene-2-carboxylic acid [6-(2-methyl-benzoylamino)-5,6,7,8-tetrahydro-quinazolin-2-yl]-amide,
[241] 3-chloro-N-{6-[3-(2-oxo-benzooxazol-3-yl)-propionyl]-5,6,7,8-tetrahydro-pyrido[4,3-d]pyrimidin-2-yl}-benzamide,
[242] 3-chloro-N-[6-(5-chloro-thiophene-2-sulfonyl)-5,6,7,8-tetrahydro-pyrido[4,3-d]pyrimidin-2-yl]-benzamide,
[243] 3,5-dichloro-N-[6-(4-methoxy-benzenesulfonyl)-5,6,7,8-tetrahydro-pyrido[4,3-d]pyrimidin-2-yl]-benzamide,
[244] 4-tert-butyl-N-[6-(5-methyl-isoxazole-3-carbonyl)-5,6,7,8-tetrahydro-pyrido[4,3-d]pyrimidin-2-yl]-benzamide,
[245] N-[6-(5-bromo-2-methoxy-benzenesulfonyl)-5,6,7,8-tetrahydro-pyrido[4,3-d]pyrimidin-2-yl]-4-methyl-benzamide,
[246] 4-tert-butyl-N-{6-[3-(2-hydroxyphenyl)-propionyl]-5,6,7,8-tetrahydro-pyrido[4,3-d]pyrimidin-2-yl}-benzamide,
[247] 4-fluoro-N-[6-(2-phenyl-butyrylamino)-5,6,7,8-tetrahydro-quinazolin-2-yl]-benzamide,
[248] 4-tert-butyl-N-[6-(4-propyl-benzoyl)-5,6,7,8-tetrahydro-pyrido[4,3-d]pyrimidin-2-yl]-benzamide,
[249] thiophene-2-carboxylic acid [6-(2-bromo-benzoylamino)-5,6,7,8-tetrahydro-quinazolin-2-yl]-amide,
[250] 2-methoxy-N-[6-(6-phenoxy-pyridine-3-carbonyl)-5,6,7,8-tetrahydro-pyrido[4,3-d]pyrimidin-2-yl]-benzamide,
[251] N-[6-(4-acetylamino-benzenesulfonyl)-5,6,7,8-tetrahydro-pyrido[4,3-d]pyrimidin-2-yl]-4-ethyl-benzamide,
[252] 3,5-dichloro-N-[6-(4-fluoro-benzenesulfonyl)-5,6,7,8-tetrahydro-pyrido[4,3-d]pyrimidin-2-yl]-benzamide,
[253] N-[6-(1-benzenesulfonyl-1H-indole-2-carbonyl)-5,6,7,8-tetrahydro-pyrido[4,3-d]pyrimidin-2-yl]-4-fluoro-benzamide,
[255] N-[6-(3-chloro-benzenesulfonylamino)-5,6,7,8-tetrahydro-quinazolin-2-yl]-4-fluoro-benzamide, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

The present invention also provides a process for the production of substituted 5,6,7,8-tetrahydro-pyrido[4,3-d]pyrimidin-2-yl-compounds of the above-stated general formula I, in which X denotes an $NR^{2a}$ group, according to which an N-protected piperidin-4-one of the general formula II,

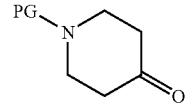

in which PG denotes a protective group, is converted by reaction with dimethoxy-methyl-dimethyl-amine of the formula III

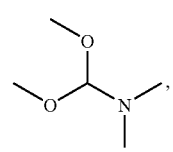

in an organic reaction medium to yield a compound of the general formula IV,

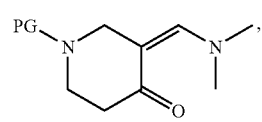

in which PG has the above-stated meaning, this latter compound is optionally purified and/or isolated, and is converted by reaction with guanidine of the formula V,

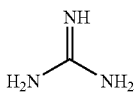

optionally in the form of a corresponding salt, in an organic reaction medium, optionally in the presence of at least one base to yield a compound of the general formula VI,

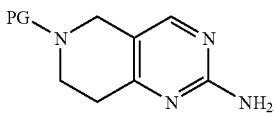

in which PG has the above-stated meaning, this latter compound is optionally purified and/or isolated, and is reacted in an organic reaction medium, optionally in the presence of at least one base and/or at least one catalyst, with a compound of the general formula $R^3$—C(=O)—$X^1$ or a compound of the general formula $(R^3$—C(=O))$_2$O, or by reaction with a compound of the general formula $R^3$—C(=O)—OH in an organic reaction medium in the presence of at least one coupling agent, optionally in the presence of at least one base, or by reaction with a compound of the general formula $R^4$—O—C(=O)—$X^{1a}$ in an organic reaction medium, optionally in the presence of at least one base, wherein $R^3$ and $R^4$ in each case have the above-stated meaning and $X^1$ and $X^{1a}$ in each case denote a leaving group, to yield a compound of the general formula VII,

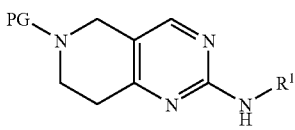

in which PG and $R^1$ have the above-stated meaning, this latter compound is optionally purified and/or isolated, and by elimination of the protective group PG is converted to yield an appropriately substituted compound of the general formula VIII,

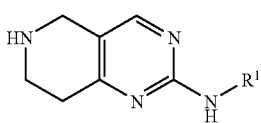

optionally in the form of a corresponding salt, this latter compound is optionally purified and/or isolated, and is converted by reaction with a compound of the general formula $R^5$—C(=O)—$X^2$ or $(R^5$—C(=O))$_2$O, in which $R^5$ in each case has the above-stated meaning and $X^2$ denotes a leaving group, in an organic reaction medium, optionally in the presence of at least one base and/or in the presence at least one catalyst, or by reaction with a compound of the general formula $R^6$—$SO_2$—$X^3$, in which $R^6$ has the above-stated meaning and $X^3$ denotes a leaving group, in an organic reaction medium, optionally in the presence of at least one base, or by reaction with a compound of the general formula $R^5$—COOH, in which $R^5$ has the above-stated meaning, in an organic reaction medium, in the presence of at least one suitable coupling agent, optionally in the presence of at least one base, to yield a compound of the general formula IX

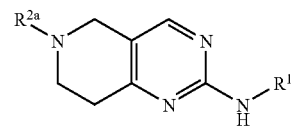

in which $R^1$ and $R^{2a}$ have the above-stated meaning, this latter compound is optionally purified and/or isolated, and optionally converted to yield a corresponding salt and this is optionally purified and/or isolated, or piperidin-4-one of the general formula X

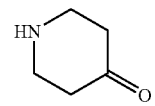

optionally in the form of a corresponding salt, is converted by reaction with a compound of the general formula R5-C(=O)—X2 or (R5-C(=O))2O, in which R5 in each case has the above-stated meaning and X2 denotes a leaving group, in an organic reaction medium, optionally in the presence of at least one base and/or in the presence of at least one catalyst, or by reaction with a compound of the general formula R6-SO2-X3, in which R6 has the above-stated meaning and X3 denotes a leaving group, in an organic reaction medium, optionally in the presence of at least one base, or by reaction with a compound of the general formula R5-COOH, in which R5 has the above-stated meaning, in an organic reaction medium, in the presence of a suitable coupling agent, optionally in the presence of at least one base, to yield a compound of the general formula XI,

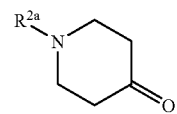

in which $R^{2a}$ has the above-stated meaning, this latter compound is optionally purified and/or isolated, and is converted by reaction with dimethoxy-methyl-dimethyl-amine of the formula III

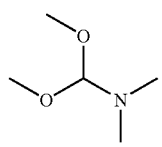

in an organic reaction medium to yield a compound of the general formula XII,

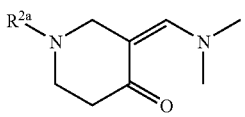

XII in which $R^{2a}$ has the above-stated meaning, this compound is optionally purified and/or isolated, and is converted with guanidine of the formula V,

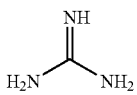

V optionally in the form of a corresponding salt, in an organic reaction medium, optionally in the presence of at least one base, to yield a compound of the general formula XIII optionally in the presence of at least one base, wherein $R^3$ and $R^4$ in each case have the above-stated meaning and $X^1$ and $X^{1a}$ denote a leaving group, to yield a compound of the general formula XIV

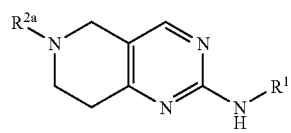

XIV in which $R^1$ and $R^{2a}$ have the above-stated meaning, and this latter compound is optionally purified and/or isolated, and optionally converted to yield a corresponding salt and this salt is optionally purified and/or isolated.

The process according to the invention for the production of substituted 5,6,7,8-tetrahydro-pyrido[4,3-d]pyrimidin-2-yl compounds of the above-stated general formula I, in which X denotes an —$NR^{2a}$ group starting from N-protected piperidin-4-one, is also reproduced in the following scheme I.

Scheme I:

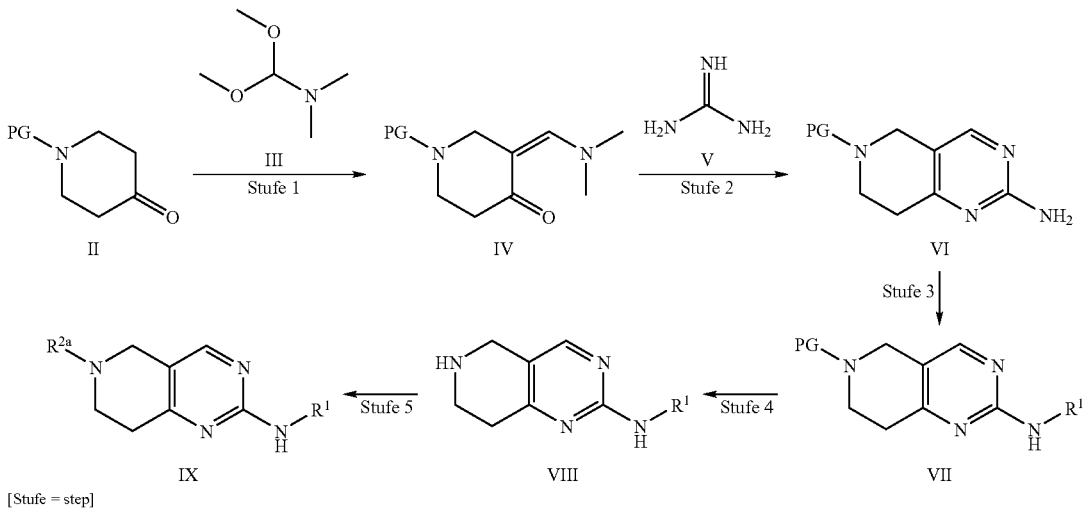

[Stufe = step]

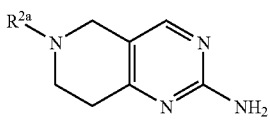

XIII this compound is optionally purified and/or isolated, and is reacted in an organic reaction medium, optionally in the presence of at least one base and/or at least one catalyst, with a compound of the general formula $R^3$—(C═O)—$X^1$ or a compound of the general formula ($R^3$—C(═O))$_2$O, or by reaction with a compound of the general formula $R^3$—COOH in an organic reaction medium in the presence of at least one coupling agent, optionally in the presence of at least one base, or by reaction with a compound of the general formula $R^4$—O—C(═O)—$X^{1a}$ in an organic reaction medium, In Step 1, piperidin-4-one, which is provided on the nitrogen atom with a protective group (PG), is firstly reacted with dimethoxymethyl-dimethyl-amine in an organic reaction medium, preferably toluene and/or benzene, to yield at least one compound of the above-stated general formula IV, which is preferably used without further working up in Step 2.

Dimethoxymethyl-dimethyl-amine, piperidin-4-one and N-protected piperidone are commercially obtainable, but may also be produced using conventional methods known to the person skilled in the art. Examples of suitable protective groups which may be considered for piperidone are trifluoroacetamide, methoxycarbonyl, ethoxycarbonyl, tert-butoxycarbonyl, benzyloxycarbonyl, allyloxycarbonyl or 9-fluorenylmethoxycarbonyl. Suitable reagents and methods for introducing these protective groups are known to the person skilled in the art.

In Step 2, the respective compound of the general formula IV is reacted optionally in the presence of at least one organic base and/or at least one organometallic base, preferably in the presence of sodium ethanolate and/or sodium methanolate, in an organic reaction medium, preferably methanol and/or ethanol, with guanidine of the formula V, optionally in the form of a corresponding salt such as for example guanidine hydrochloride, to yield the respective compound of the above-stated general formula VI.

Guanidine and the corresponding salts thereof are commercially obtainable, but may also be produced using conventional methods known to the person skilled in the art.

In Step 3, the respective compound of the general formula VI is reacted under conventional conditions known to the person skilled in the art in an organic reaction medium such as for example pyridine by acylation with at least one compound of the general formula $R^3$—C(=O)—$X^1$ or at least one compound of the general formula ($R^3$—C(=O))$_2$O, optionally in the presence of at least one organic base and/or at least one inorganic base, which may preferably be selected from the group consisting of diisopropylethylamine, triethylamine, pyridine and diethylamine, optionally in the presence of at least one catalyst, preferably in the presence of dimethylaminopyridine (DMAP), to yield the respective compound of the general formula VII.

Alternatively, the reaction of the respective compound of the general formula VI may also proceed with at least one carboxylic acid of the general formula $R^3$—COOH, in which $R^3$ in each case has the above-stated meaning, in an organic reaction medium, preferably selected from the group consisting of dichloromethane, DMF, THF and acetonitrile, optionally in the presence of at least one conventional coupling agent known to the person skilled in the art, preferably selected from the group consisting of N,N'-carbonyldiimidazole (CDI), N,N'-dicyclohexylcarbodiimide (DCC) and N-ethyl-N'-[3-(dimethylamino)-propyl]-carbodiimide (EDCI), or in the presence of 1-hydroxy-7-azabenzotriazole (HOAt) and at least one organic base such as for example diisopropylethylamine (DIPEA).

A further possible alternative is for the reaction to proceed with at least one compound of the general formula $R^4$—O—C(=O)—$X^{1a}$, in which $R^4$ has the above-stated meaning and $X^{1a}$ denotes a leaving group, in an organic reaction medium such as for example acetonitrile, DMF or dichloromethane, optionally in the presence of at least one base for example selected from the group consisting of aqueous potassium carbonate, sodium hydrogencarbonate, sodium hydroxide solution, diisopropylethylamine, triethylamine, pyridine and diethylamine.

The respective compound of the general formula VII is converted by elimination of the respective protective group (PG) in Step 4 under conventional conditions known to the person skilled in the art to yield the respective compound of the above-stated general formula VIII, optionally in the form of a corresponding salt such as for example trifluoroacetate.

For example, elimination of the above-stated protective groups may proceed in the presence of at least one inorganic base, acid or Lewis acid, such as for example potassium carbonate, lithium hydroxide, potassium hydroxide, sulfuric acid, hydrobromic acid, hydrofluoric acid, hydrochloric acid, boron trifluoride etherate or boron trichloride, at least one organic acid such as for example trifluoroacetic acid, trifluoromethanesulfonic acid or acetic acid, or in the presence of at least one organic base, such as for example morpholine, triethylamine, diethylamine, diisopropylethylamine or pyridine or by hydrogenation.

The respective compound of the above-stated general formula VIII is reacted in Step 5 under conventional conditions known to the person skilled in the art in an organic reaction medium, such as for example pyridine, by acylation with at least one compound of the general formula $R^5$—C(=O)—$X^2$ or at least one compound of the general formula ($R^5$—C(=O))$_2$O, in which $R^5$ in each case has the above-stated meaning and $X^2$ denotes a conventional leaving group familiar to the person skilled in the art, preferably a halogen such as for example chlorine, optionally in the presence of at least one organic base and/or at least one inorganic base, preferably at least one base selected from the group consisting of diisopropylethylamine, triethylamine, pyridine and diethylamine, optionally in the presence of at least one catalyst, preferably dimethylaminopyridine (DMAP), or by sulfonylation with at least one sulfonyl compound of the general formula $R^6$—S(=O)$_2$—$X^3$, in which $R^6$ in each case has the above-stated meaning and $X^3$ denotes a conventional leaving group familiar to the person skilled in the art, preferably a halogen such as for example chlorine, optionally in the presence of at least one organic base and/or at least one inorganic base, preferably at least one base selected from the group consisting of sodium hydrogencarbonate, diisopropylethylamine, triethylamine, pyridine and diethylamine, or by reaction with at least one carboxylic acid of the general formula $R^5$—COOH, in which $R^5$ in each case has the above-stated meaning, in an organic reaction medium, preferably selected from the group consisting of dichloromethane, DMF, THF and acetonitrile, optionally in the presence of at least one conventional coupling agent known to the person skilled in the art, preferably selected from the group consisting of N,N'-carbonyldiimidazole (CDI), N,N'-dicyclohexylcarbodiimide (DCC) and N-ethyl-N'-[3-(dimethylamino)-propyl]-carbodiimide (EDCI), or in the presence of 1-hydroxy-7-azabenzotriazole (HOAt) and at least one organic base such as for example diisopropylethylamine (DIPEA) to yield the respective substituted 5,6,7,8-tetrahydro-pyrido[4,3-d]pyrimidin-2-yl compound of the above-stated general formula I.

Alternatively, the substituted 5,6,7,8-tetrahydro-pyrido[4,3-d]pyrimidin-2-yl compounds according to the invention of the above-stated general formula I, in which X denotes an —NR$^{2a}$ group, are produced starting from piperidin-4-one. The corresponding process is illustrated in Scheme II.

Scheme II:

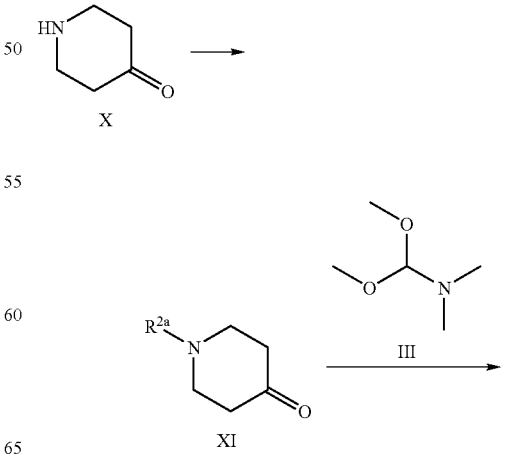

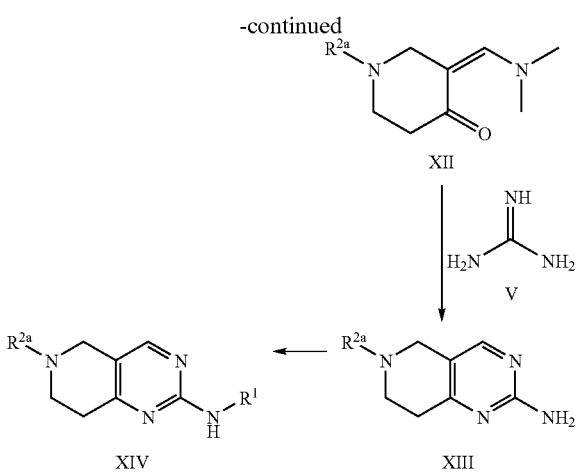

The respective compound of the above-stated general formula XI is obtained starting from piperidin-4-one of the general formula X, optionally in the form of a corresponding salt such as for example the hydrochloride, under conventional conditions known to the person skilled in the art in an organic reaction medium, such as for example pyridine, by acylation with at least one compound of the general formula $R^5$—C(=O)—$X^2$ or $(R^5$—C(=O)$)_2$O in which $R^5$ in each case has the above-stated meaning and $X^2$ denotes a conventional leaving group familiar to the person skilled in the art, preferably a halogen such as for example chlorine, optionally in the presence of at least one organic base and/or at least one inorganic base, preferably at least one base selected from the group consisting of diisopropylethylamine, triethylamine, pyridine and diethylamine, optionally in the presence of at least one catalyst, preferably DMAP, or by sulfonylation with at least one compound of the general formula $R^6$—S(=O)$_2$—$X^3$, in which $R^6$ has the above-stated meaning and $X^3$ denotes a conventional leaving group familiar to the person skilled in the art, preferably a halogen such as for example chlorine, in the presence of at least one organic base and/or at least one inorganic base, preferably at least one base selected from the group consisting of sodium hydrogencarbonate, diisopropylethylamine, triethylamine, pyridine and diethylamine, or by reaction with a carboxylic acid of the general formula $R^5$—COOH in an organic reaction medium, preferably selected from the group consisting of dichloromethane, DMF, THF and acetonitrile, in the presence of a conventional coupling agent known to the person skilled in the art, preferably selected from the group consisting of CDI, DCC and EDCI, or optionally in the presence of HOAt and at least one organic base such as for example DIPEA.

The resultant compound of the above-stated general formula XI is then reacted with dimethoxy-methyl-dimethyl-amine of the formula III in an organic reaction medium, preferably toluene and/or benzene, to yield the respective compound of the above-stated general formula XII, which compound is preferably converted without further working up in the presence of at least one organic base and/or at least one organometallic base, preferably sodium ethanolate and/or sodium methanolate, in an organic reaction medium, preferably methanol and/or ethanol, with guanidine of the above-stated formula V, optionally in the form of a corresponding salt such as for example guanidine hydrochloride, to yield the respective compound of the above-stated general formula XIII.

Reaction of the respective compound of the general formula XIII with at least one compound of the general formula $R^4$—O—(C=O)—$X^{1a}$ or at least one compound of the general formula $(R^3$—C(=O)$)_2$O or a compound of the general formula $R^3$—C(=O)—$X^1$, in which $R^3$ and $R^4$ in each case have the above-stated meaning and $X^1$ and $X^{1a}$ denote a conventional leaving group familiar to the person skilled in the art, preferably a halogen such as for example chlorine, in the presence of at least one base, preferably selected from the group consisting of aqueous potassium carbonate, sodium hydrogencarbonate, sodium hydroxide solution, diisopropylethylamine, triethylamine, pyridine, diethylamine, optionally in an organic reaction medium, preferably selected from the group consisting of acetonitrile, DMF and dichloromethane, then leads to the respective substituted 5,6,7,8-tetrahydro-pyrido[4,3-d]pyrimidin-2-yl compounds of the above-stated general formula I, in which X denotes an —$NR^{2a}$ group and $R^1$ has the above-stated meaning.

Alternatively, reaction of the respective compound of the general formula XIII may also proceed with at least one carboxylic acid of the general formula $R^3$—COOH, in which $R^3$ in each case has the above-stated meaning, in an organic reaction medium, preferably selected from the group consisting of dichloromethane, DMF, THF and acetonitrile, optionally in the presence of at least one conventional coupling agent known to the person skilled in the art, preferably selected from the group consisting of N,N'-carbonyldiimidazole (CDI), N,N'-dicyclohexylcarbodiimide (DCC) and N-ethyl-N'-[3-(dimethylamino)-propyl]-carbodiimide (EDCI), or in the presence of 1-hydroxy-7-azabenzotriazole (HOAt) and at least one organic base such as for example diisopropylethylamine (DIPEA).

The present invention also provides a process for the production of substituted 5,6,7,8-tetrahydro-quinazolin-2-yl compounds of the above-stated general formula I, in which X denotes a C(H)(NHR$^2$) group, according to which 1,4-dioxa-spiro[4.5]dec-8-yl-amine of the formula C

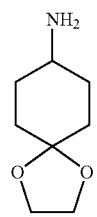

is converted by reaction with a compound of the general formula $R^5$—C(=O)—$X^4$ or $(R^5$—C(=O)$)_2$O, in which $R^5$ in each case has the above-stated meaning and $X^4$ denotes a leaving group, in an organic reaction medium, optionally in the presence of at least one base and/or in the presence at least one catalyst, or by reaction with a compound of the general formula $R^6$—SO$_2$—$X^5$, in which $R^6$ has the above-stated meaning and $X^5$ denotes a leaving group, in an organic reaction medium, optionally in the presence of at least one base, or by reaction with a compound of the general formula $R^5$—COOH, in which $R^5$ has the above-stated meaning, in an organic reaction medium, in the presence of a suitable coupling agent, optionally in the presence of at least one base, to yield a compound of the general formula D

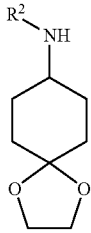

D in which $R^2$ has the above-stated meaning, this latter compound is optionally purified and/or isolated, and converted by elimination of the acetal group in an organic reaction medium in the presence of water and at least one acid to yield a compound of the general formula E,

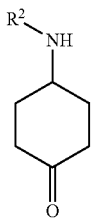

E in which $R^2$ has the above-stated meaning, and this latter compound is converted by introduction of a protective group ($PG^1$) in an organic reaction medium to yield the compound of the general formula F

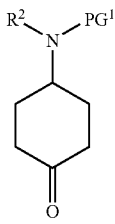

F in which $R^2$ has the above-stated meaning and $PG^1$ denotes a protective group, this latter compound is optionally purified and/or isolated, and is converted by reaction with dimethoxymethyl-dimethyl-amine of the general formula III

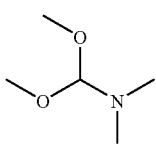

III in an organic reaction medium to yield a compound of the general formula G

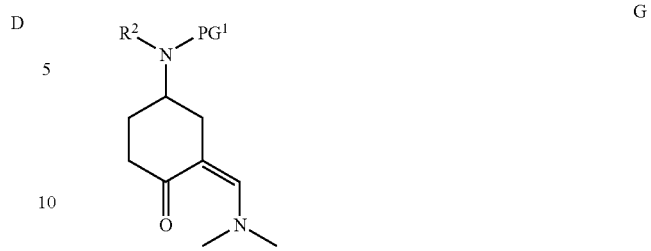

G in which $R^2$ and $PG^1$ have the above-stated meaning, and this latter compound is optionally purified and/or isolated, and optionally converted in the presence of at least one base in an organic reaction medium with a guanidine compound of the formula V, optionally in the form of a corresponding salt,

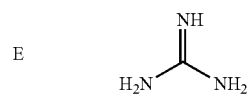

V to yield a compound of the general formula H

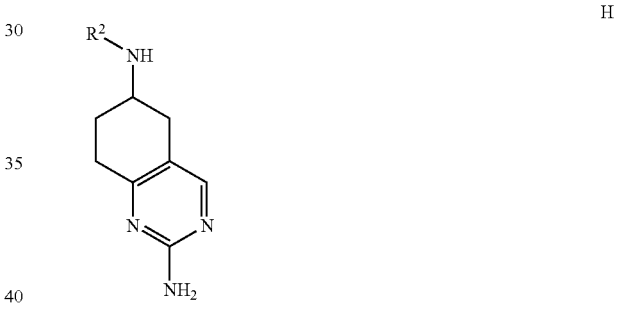

H this latter compound is optionally purified and/or isolated, and is converted by introduction of a protective group (PG2) in an organic reaction medium to yield a compound of the general formula I

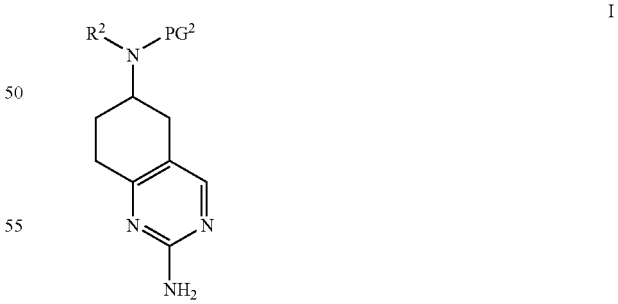

I in which $R^2$ and $PG^2$ have the above-stated meaning, this latter compound is optionally purified and/or isolated, and converted by reaction with a compound of the general formula $R^3$—C(=O)—$X^6$ or a compound of the general formula $(R^3$—C(=O)$)_2$O, in which $R^3$ in each case has the above-stated meaning and $X^6$ denotes a leaving group, or by reaction with a compound of the general formula $R^3$COOH, in which $R^3$ has the above-stated meaning, in an organic reaction medium in the presence of a coupling agent, optionally in the presence of at least one base, or by reaction with a compound of the general formula $R^4$—O—C(=O)—$X^{1a}$ in an organic reaction medium, optionally in the presence of a base, to yield a compound of the general formula J

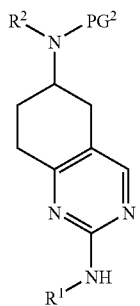

in which $R^2$ and $PG^2$ have the above-stated meaning and $R^1$ has the above-stated meaning, this latter compound is optionally purified and/or isolated, and converted by elimination of the protective group to yield a 5,6,7,8-tetrahydro-quinazolin-2-yl compound of the general formula I, in which X denotes a C(H)($NHR^2$) group, this latter compound is optionally purified and/or isolated and then optionally converted to yield a corresponding salt, and this is optionally purified and/or isolated.

The process according to the invention for the production of substituted 5,6,7,8-tetrahydro-quinazolin-2-yl compounds of the above-stated general formula I, in which X denotes a C(H)($NHR^2$) group, is also reproduced in Scheme III below.

1,4-Dioxa-spiro[4.5]dec-8-yl-amine of the formula C may be produced using conventional methods known to the person skilled in the art, for example starting from 1,4-dioxa-spiro [4.5]decan-8-one, which is converted via reductive amination with benzylamine in an organic reaction medium, such as for example dichloromethane, in the presence of sodium cyanoborohydride or sodium triacetoxyborohydride or by reaction with hydroxylamine hydrochloride in the presence of an organic base, such as triethylamine or Amberlyst, in an organic reaction medium, such as ethanol, to yield the compound of the general formula B, in which R denotes a hydroxy group or a benzyl residue, which compound is optionally purified and/or isolated, and is reacted in the presence of at least one catalyst such as palladium on activated carbon (Pd (C)) by hydrogenation or by reduction with at least one metal hydride such as for example lithium aluminium hydride in an organic reaction medium, preferably ethanol and/or THF, to yield 1,4-dioxa-spiro[4.5]dec-8-yl-amine of the formula C.

The compound 1,4-dioxa-spiro[4.5]dec-8-yl-amine of the formula C is then reacted under conventional conditions known to the person skilled in the art in an organic reaction medium, such as for example pyridine, by acylation with a compound of the general formula $R^5$—C(=O)—$X^4$ or ($R^5$— C(=O))$_2$O, in which $R^5$ has the above-stated meaning, and $X^4$ denotes a conventional leaving group known to the person skilled in the art, preferably halogen, particularly preferably chlorine, optionally in the presence of at least one organic base and/or at least one inorganic base, preferably at least one base selected from the group consisting of diisopropylethylamine, triethylamine, pyridine and diethylamine, optionally in the presence of at least one catalyst, preferably DMAP, or by sulfonylation of the compound 1,4-dioxa-spiro[4.5]dec-8-yl-amine of the formula C with at least one sulfonyl com- Scheme III:

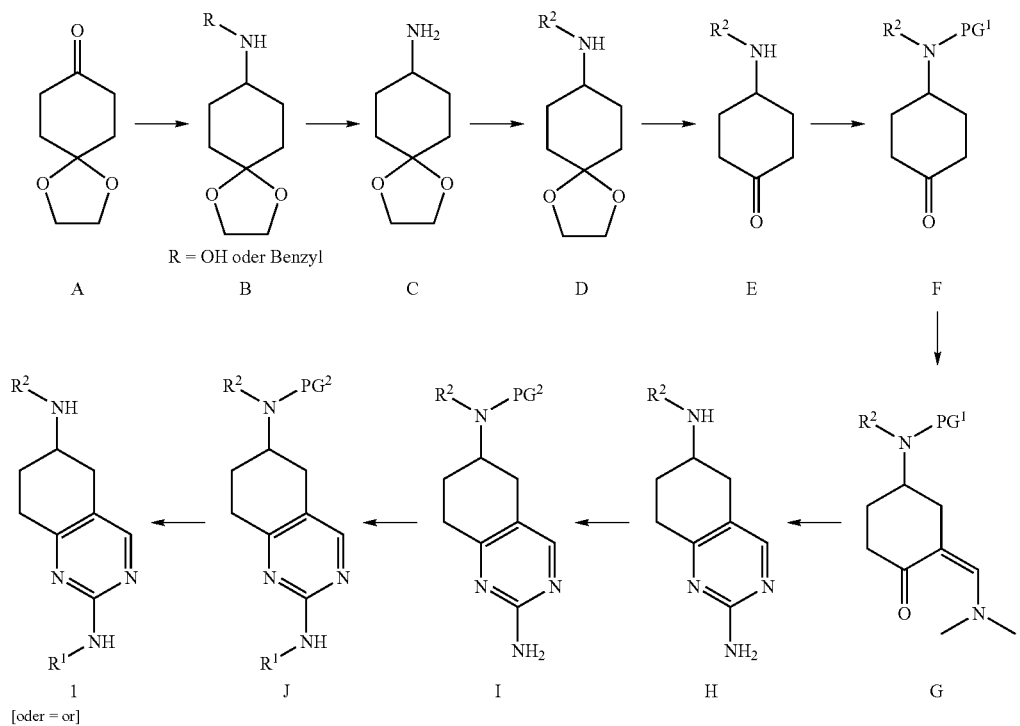

R = OH oder Benzyl

[oder = or]

pound of the general formula $R^6$—$SO_2$—$X^5$, in which $R^6$ has the above-stated meaning, and $X^5$ denotes a conventional leaving group known to the person skilled in the art, preferably halogen, particularly preferably chlorine, in an organic reaction medium, preferably acetonitrile and/or dichloromethane, in the presence of at least one organic base and/or at least one inorganic base, preferably in the presence of at least one base selected from the group consisting of potassium carbonate, sodium hydrogencarbonate, diisopropylethylamine, triethylamine, pyridine and diethylamine, or by reaction of the compound 1,4-dioxa-spiro[4.5]dec-8-yl-amine of the formula C with at least one carboxylic acid of the general formula $R^5$—COOH, in which $R^5$ has the above-stated meaning, in at least one organic reaction medium, preferably selected from the group consisting of dichloromethane, DMF, THF and acetonitrile, in the presence of at least one conventional coupling agent known to the person skilled in the art to yield the corresponding compound of the general formula D.

Corresponding coupling agents which lead to the formation of an amide grouping are for example CDI, DCC or EDCI. Alternatively, HOAt, in conjunction with at least one organic base, such as for example DIPEA, may also be considered.

The respective compound of the general formula D is then converted by elimination of the acetal protective group under conventional conditions known to the person skilled in the art to yield a compound of the general formula E, preferably by elimination of the acetal protective group in an organic reaction medium, preferably dichloromethane and/or methanol, in the presence of water with at least one inorganic acid and/or at least one organic acid, preferably selected from the group consisting of methanolic hydrochloric acid, hydrochloric acid, p-toluenesulfonic acid, trifluoroacetic acid, acetic acid, and citric acid, or in the presence of a Lewis acid.

Starting from a compound of the general formula E, the respective compound F is obtained by introduction of a protective group (PG1).

Suitable protective groups (PG1) are for example trifluoroacetamide, methoxycarbonyl, ethoxycarbonyl, tert-butoxycarbonyl, benzyloxycarbonyl, allyloxycarbonyl and 9-fluorenylmethoxycarbonyl. Suitable reagents and processes for introducing these protective groups are known to the person skilled in the art.

The respective compound of the general formula F is then reacted with dimethoxymethyl-dimethyl-amine of the general formula III in an organic reaction medium, preferably toluene and/or benzene, to yield the corresponding compound of the general formula G, which is preferably reacted without further working up in the presence of at least one organic base or at least one organometallic base, preferably in the presence of sodium ethanolate and/or sodium methanolate, in an organic reaction medium, preferably methanol and/or ethanol, with guanidine of the general formula V, preferably in the form of a corresponding salt, such as for example guanidine hydrochloride, to yield the respective compound of the general formula H.

The protective group may optionally be partially eliminated in the process and is reintroduced under conventional conditions known to the person skilled in the art, such that the respective compound of the formula I is obtained. The protective group (PG2) introduced may be identical to or different from, preferably identical to, the above-stated protective group (PG1).

The respective compound of the above-stated general formula I is then reacted under conventional conditions known to the person skilled in the art in an organic reaction medium such as for example pyridine by acylation with at least one compound of the general formula $R^3$—C(=O)—$X^6$ or a compound of the general formula $(R^3$—C(=O)$)_2$O, in which $R^3$ in each case has the above-stated meaning and $X^6$ denotes a conventional leaving group known to the person skilled in the art, preferably halogen, particularly preferably chlorine, in an organic reaction medium, optionally in the presence of at least one organic base and/or at least one inorganic base, preferably a base selected from the group consisting of diisopropylethylamine, triethylamine, pyridine and diethylamine, optionally in the presence of at least one catalyst, preferably DMAP, or by reaction with at least one carboxylic acid $R^3$—COOH, in which $R^3$ has the above-stated meaning, in an organic reaction medium, preferably selected from the group consisting of dichloromethane, DMF, THF and acetonitrile, in the presence of at least one conventional coupling agent, preferably selected from the group consisting of CDI, DCC and EDCI, or in the presence of HOAt and at least one organic base such as for example DIPEA to yield the corresponding compound of the general formula J.

A further possible alternative is for the reaction to proceed with at least one compound of the general formula $R^4$—O—C(=O)—$X^{1a}$, in which $R^4$ has the above-stated meaning and $X^{1a}$ denotes a leaving group, in an organic reaction medium, such as for example acetonitrile, DMF or dichloromethane, optionally in the presence of at least one base for example selected from the group consisting of aqueous potassium carbonate, sodium hydrogencarbonate, sodium hydroxide solution, diisopropylethylamine, triethylamine, pyridine and diethylamine.

The respective compound of the general formula J is then converted by elimination of the protective group (PG2) under conventional conditions known to the person skilled in the art to yield the respective substituted 5,6,7,8-tetrahydroquinazolin-2-yl compound of the above-stated general formula I, in which X denotes a C(H)(NHR$^2$) group.

Elimination of the above-stated protective group (PG2) may proceed for example in the presence of an inorganic base, acid or Lewis acid, such as potassium carbonate, lithium hydroxide, potassium hydroxide, sulfuric acid, hydrobromic acid, hydrofluoric acid, hydrochloric acid, boron trifluoride etherate, boron trichloride, an organic acid such as trifluoroacetic acid, trifluoromethanesulfonic acid, acetic acid, or in the presence of an organic base, such as morpholine, triethylamine, diethylamine, diisopropylethylamine, pyridine or by hydrogenation.

The compounds of the general formulae $R^3$—C(=O)—$X^1$, $R^5$—C(=O)—$X^2$, $R^5$—C(=O)—$X^4$, $R^3$—C(=O)—$X^6$, $(R^3$—C(=O)$)_2$O, $(R^5$—C(=O)$)_2$O, $R^3$—COOH, $R^5$—COOH, $R^6$—$SO_2$—$X^3$, $R^6$—$SO_2$—$X^5$ and $R^4$—O—(C=O)—$X^{1a}$ are in each case commercially obtainable and/or may be produced using conventional methods known to the person skilled in the art.

The above-described reactions may in each case be performed under conventional conditions familiar to the person skilled in the art, for example with regard to temperature, pressure or the sequence of addition of the components. Optimum control of the process under the respective conditions may optionally be established by the person skilled in the art by simple preliminary testing.

The intermediate and final products obtained by the above-described reactions may in each case, if desired and/or necessary, be purified and/or isolated by conventional methods known to the person skilled in the art. Suitable purification methods are, for example, extraction methods and chromatographic methods such as column chromatography or preparative chromatography.

All the above-described process steps and in each case also the purification and/or isolation of intermediate or final products may be performed in part or entirely under an inert gas atmosphere, preferably under a nitrogen atmosphere.

If the substituted 5,6,7,8-tetrahydro-pyrido[4,3-d]pyrimidin-2-yl and 5,6,7,8-tetrahydro-quinazolin-2-yl compounds according to the invention of the above-stated general formula I are obtained after production thereof in the form of a mixture of the stereoisomers thereof, preferably in the form of the racemates thereof or other mixtures of the various enantiomers and/or diastereomers thereof, these may be resolved and optionally isolated using conventional methods known to the person skilled in the art. Examples are chromatographic separation processes, in particular liquid chromatography processes at standard pressure or at elevated pressure, preferably MPLC and HPLC processes, and fractional crystallisation processes. Individual enantiomers, for example diastereomeric salts formed by means of HPLC on a chiral phase or by means of crystallisation with chiral acids, for instance (+)-tartaric acid, (−)-tartaric acid or (+)-10-camphorsulfonic acid, may here in particular be separated from one another.

The substituted 5,6,7,8-tetrahydro-pyrido[4,3-d]pyrimidin-2-yl and 5,6,7,8-tetrahydro-quinazolin-2-yl compounds according to the invention of the above-stated general formula I and optionally in each case corresponding stereoisomers may be obtained using conventional methods known to the person skilled in the art in the form of corresponding salts, in particular in the form of corresponding physiologically acceptable salts, wherein the pharmaceutical preparation according to the invention may comprise one or more salts of one or more of these compounds.

The respective salts of the substituted 5,6,7,8-tetrahydro-pyrido[4,3-d]pyrimidin-2-yl and 5,6,7,8-tetrahydro-quinazolin-2-yl compounds according to the invention of the above-stated general formula I and corresponding stereoisomers may be obtained for example by reaction with one or more inorganic acids and/or one or more organic acids. Suitable acids may preferably be selected from the group consisting of perchloric acid, hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, saccharic acid, cyclohexanesulfamic acid, aspartame, monomethylsebacic acid, 5-oxo-proline, hexane-1-sulfonic acid, nicotinic acid, 2-aminobenzoic acid, 3-aminobenzoic acid or 4-aminobenzoic acid, 2,4,6-trimethylbenzoic acid, □-lipoic acid, acetylglycine, hippuric acid, phosphoric acid, maleic acid, malonic acid and aspartic acid.

The substituted 5,6,7,8-tetrahydro-pyrido[4,3-d]pyrimidin-2-yl and 5,6,7,8-tetrahydro-quinazolin-2-yl compounds according to the invention of the above-stated general formula I and optionally corresponding stereoisomers and in each case the physiologically acceptable salts thereof may be obtained using conventional methods known to the person skilled in the art also in the form of the solvates thereof, in particular in the form of the hydrates thereof.

It has surprisingly been found that the substituted 5,6,7,8-tetrahydro-pyrido[4,3-d]pyrimidin-2-yl and 5,6,7,8-tetrahydro-quinazolin-2-yl compounds according to the invention are suitable for noradrenalin receptor regulation, in particular for inhibiting noradrenalin reuptake (noradrenalin uptake), for 5-HT receptor regulation, in particular for inhibiting 5-hydroxy-tryptophan reuptake (5-HT uptake), for mGluR5 receptor regulation and/or for batrachotoxin (BTX) receptor regulation and may therefore be used in particular as pharmaceutical active ingredients in pharmaceutical preparations for the prevention and/or treatment of disorders or diseases associated with these receptors or processes.

The substituted 5,6,7,8-tetrahydro-pyrido[4,3-d]pyrimidin-2-yl and 5,6,7,8-tetrahydro-quinazolin-2-yl compounds according to the invention of the above-stated general formula I and optionally corresponding stereoisomers and in each case the corresponding salts and solvates are toxicologically safe and are therefore suitable as pharmaceutical active ingredients in pharmaceutical preparations.

The present invention accordingly also provides a pharmaceutical preparation containing at least one substituted 5,6,7,8-tetrahydro-pyrido[4,3-d]pyrimidin-2-yl or 5,6,7,8-tetrahydro-quinazolin-2-yl compound according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances.

The pharmaceutical preparation according to the invention is suitable for noradrenalin receptor regulation, in particular for inhibiting noradrenalin reuptake (noradrenalin uptake), for 5-HT receptor regulation, in particular for inhibiting 5-hydroxy-tryptophan reuptake (5-HT uptake), for mGluR5 receptor regulation and/or for batrachotoxin (BTX) receptor regulation.

The pharmaceutical preparation according to the invention is preferably suitable for the prevention and/or treatment of disorders and/or diseases, which are mediated at least in part by noradrenalin receptors, 5-HT receptors, mGluR5 receptors and/or batrachotoxin (BTX) receptors.

The pharmaceutical preparation according to the invention is particularly preferably suitable for the prevention and/or treatment of pain, preferably of pain selected from the group consisting of acute pain, chronic pain, neuropathic pain and visceral pain, and/or for the prevention and/or treatment of migraine, depression, urinary incontinence, coughing, neurodegenerative diseases, preferably selected from the group consisting of Parkinson's disease, Huntington's chorea, Alzheimer's disease and multiple sclerosis, disorders of food intake, preferably selected from the group consisting of bulimia, anorexia, obesity and cachexia, cognitive dysfunction, preferably memory disorders, cognitive deficiency states (attention deficit syndrome, ADS), disorders of the nervous system, epilepsy, schizophrenia, cerebral ischaemia, muscle spasms, cramps, diarrhoea, pruritus, gastro-oesophageal reflux syndrome, panic attacks, alcohol and/or drug (in particular nicotine and/or cocaine) abuse and/or abuse of medicines, alcohol and/or drug (in particular nicotine and/or cocaine) dependency and/or dependency on medicines, preferably for the prevention and/or reduction of withdrawal symptoms associated with alcohol and/or drug dependency and/or dependency on medicines, for the prevention and/or reduction of a development of tolerance to medicines, in particular medicines based on opioids, for regulating food intake, for modulating locomotor activity, for regulating the cardiovascular system, for local anaesthesia, for anxiolysis, for increasing vigilance, for increasing libido, for diuresis, and/or for antinatriuresis.

The pharmaceutical preparation according to the invention is very particularly preferably suitable for the prevention and/or treatment of pain, preferably acute pain, chronic pain, neuropathic pain or visceral pain.

The present invention also provides the use of at least one substituted 5,6,7,8-tetrahydro-pyrido[4,3-d]pyrimidin-2-yl or 5,6,7,8-tetrahydro-quinazolin-2-yl compound according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically compatible auxiliary substances for the production of a pharmaceutical preparation for noradrenalin receptor regulation, in particular for inhibiting noradrenalin reuptake (noradrenalin uptake), for 5-HT receptor regulation, in particular for inhibiting 5-hydroxy-tryptophan reuptake (5-HT uptake), for mGluR5 receptor regulation and/or for batrachotoxin (BTX) receptor regulation.

The use is preferred of at least one substituted 5,6,7,8-tetrahydro-pyrido[4,3-d]pyrimidin-2-yl or 5,6,7,8-tetrahydro-quinazolin-2-yl compound according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically compatible auxiliary substances for the production of a pharmaceutical preparation for the prevention and/or treatment of disorders and/or diseases which are mediated at least in part by noradrenalin receptors, 5-HT receptors, mGluR5 receptors and/or batrachotoxin (BTX) receptors.

The use is particularly preferred of at least one substituted 5,6,7,8-tetrahydro-pyrido[4,3-d]pyrimidin-2-yl or 5,6,7,8-tetrahydro-quinazolin-2-yl compound according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically compatible auxiliary substances for the production of a pharmaceutical preparation for the prevention and/or treatment of pain, preferably of pain selected from the group consisting of acute pain, chronic pain, neuropathic pain and visceral pain, and/or for the prevention and/or treatment of migraine, depression, urinary incontinence, coughing, neurodegenerative diseases, preferably selected from the group consisting of Parkinson's disease, Huntington's chorea, Alzheimer's disease and multiple sclerosis, disorders of food intake, preferably selected from the group consisting of bulimia, anorexia, obesity and cachexia, cognitive dysfunction, preferably memory disorders, cognitive deficiency states (attention deficit syndrome, ADS), disorders of the nervous system, epilepsy, schizophrenia, cerebral ischaemia, muscle spasms, cramps, diarrhoea, pruritus, gastro-oesophageal reflux syndrome, panic attacks, alcohol and/or drug abuse and/or abuse of medicines, alcohol and/or drug dependency and/or dependency on medicines, preferably for the prevention and/or reduction of withdrawal symptoms associated with alcohol and/or drug dependency and/or dependency on medicines, for the prevention and/or reduction of the development of tolerance to medicines, in particular medicines based on opioids, for regulating food intake, for modulating locomotor activity, for regulating the cardiovascular system, for local anaesthesia, for anxiolysis, for increasing vigilance, for increasing libido, for diuresis, and/or for antinatriuresis.

The use is very particularly preferred of at least one substituted 5,6,7,8-tetrahydro-pyrido[4,3-d]pyrimidin-2-yl or 5,6,7,8-tetrahydro-quinazolin-2-yl compound according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically compatible auxiliary substances for the production of a pharmaceutical preparation for the prevention and/or treatment of pain, preferably of acute pain, chronic pain, neuropathic pain or visceral pain.

The pharmaceutical preparation according to the invention is suitable for administration to adults and children including small children and babies.

The pharmaceutical preparation according to the invention may be formulated as a liquid, semisolid or solid dosage form, for example in the form of solutions for injection, drops, succi, syrups, sprays, suspensions, tablets, patches, capsules, dressings, suppositories, ointments, creams, lotions, gels, emulsions, aerosols or in multiparticulate form, for example in the form of pellets or granules, optionally pressed into tablets, packaged in capsules or suspended in a liquid, and may also be administered as such.

In addition to at least one substituted 5,6,7,8-tetrahydro-pyrido[4,3-d]pyrimidin-2-yl or 5,6,7,8-tetrahydro-quinazolin-2-yl compound according to the invention of the above-stated general formula I, optionally in the form of the pure stereoisomer thereof, in particular enantiomer or diastereomer, the racemate thereof or in the form of mixtures of the stereoisomers, in particular the enantiomers or diastereomers, in any desired mixing ratio, or optionally in the form of a corresponding salt or in each case in the form of a corresponding solvate, the pharmaceutical preparation according to the invention conventionally contains further physiologically acceptable pharmaceutical auxiliary substances, which may preferably be selected from the group consisting of matrix materials, fillers, solvents, diluents, surface-active substances, dyes, preservatives, disintegrants, slip agents, lubricants, aromas and binders.

Selection of the physiologically acceptable auxiliary substances and the quantities thereof which are to be used depends upon whether the pharmaceutical preparation is to be administered orally, subcutaneously, parenterally, intravenously, intraperitoneally, intradermally, intramuscularly, intranasally, buccally, rectally or topically, for example onto infections of the skin, mucous membranes or eyes. Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration.

The substituted 5,6,7,8-tetrahydro-pyrido[4,3-d]pyrimidin-2-yl or 5,6,7,8-tetrahydro-quinazolin-2-yl compounds used in the pharmaceutical preparation according to the invention in a depot in dissolved form or in a dressing, optionally with the addition of skin penetration promoters, are suitable percutaneous administration preparations.

Orally or percutaneously administrable formulations may also release the respective substituted 5,6,7,8-tetrahydro-pyrido[4,3-d]pyrimidin-2-yl or 5,6,7,8-tetrahydro-quinazolin-2-yl compounds in delayed manner.

Production of the pharmaceutical preparations according to the invention proceeds with the assistance of conventional means, devices, methods and processes known from the prior art, such as are described for example in "Remington's Pharmaceutical Sciences", ed. A. R. Gennaro, 17th ed., Mack Publishing Company, Easton, Pa. (1985), in particular in part 8, chapters 76 to 93. The corresponding description is hereby introduced as a reference and is deemed to be part of the disclosure.

The quantity of the respective substituted 5,6,7,8-tetrahydro-pyrido[4,3-d]pyrimidin-2-yl or 5,6,7,8-tetrahydroquinazolin-2-yl compound to be administered to the patient may vary and is for example dependent on the weight or age of the patient and on the mode of administration, the indication and the severity of the complaint. Conventionally, 0.005 to 5000 mg/kg, preferably 0.05 to 500 mg/kg, particularly preferably 0.05 to 75 mg/kg of patient body weight of at least one such compound are administered.

Pharmacological Methods:

I. Method for Determining Noradrenalin and 5-HT Uptake Inhibition:

Synaptosomes from rat brain regions are freshly isolated for in vitro studies, as described in the publication "The isolation of nerve endings from brain" by E. G. Gray and V. P. Whittaker, J. Anatomy 96, pages 79-88, 1962. The corresponding literature description is hereby introduced as a reference and is deemed to be part of the disclosure.

The tissue (hypothalamus for the determination of noradrenalin uptake inhibition and medulla and pons for the determination of 5-HT uptake inhibition) is homogenised in ice-cooled 0.32 M sucrose (100 mg of tissue/1 mL) in a glass homogeniser with Teflon pestle using five complete up and down strokes at 840 revolutions/minute.

The homogenate is centrifuged at 4° C. for 10 minutes at 1000 g. After subsequent centrifugation at 17000 g for 55 minutes, the synaptosomes ($P_2$ fraction) are obtained, which are resuspended in 0.32 M glucose (0.5 mL/100 mg of original weight).

The particular uptake is measured in a 96-well microtitre plate. The volume is 250 µl and the incubation proceeds at room temperature (approx. 20-25° C.) under an $O_2$ atmosphere.

The incubation time is 7.5 minutes for [$^3$H]—NA and 5 minutes for [$^3$H]-5-HT.

The 96 samples are then filtered through a Unifilter GF/B□ microtitre plate (Packard) and washed with 200 mL of incubated buffer using a "Brabdel MPXRI-96T Cell-Harvester". The Unifilter GF/B plate is dried for 1 hour at 55° C. The plate is then sealed with a Back seal□ (Packard) and 35 µl of scintillation fluid are added per well (Ultima Gold□, Packard). After sealing with a top seal□ (Packard) and establishing an equilibrium (around 5 hours), radioactivity is determined in a "Trilux 1450 Microbeta" (Wallac).

The quantity of protein used in the above determination corresponds to the values known from the literature, as for example described in "Protein measurement with the folin phenol reagent", Lowry et al., J. Biol. Chem., 193, 265-275, 1951.

A detailed description of the method may additionally be found in the literature, for example in M. Ch. Frink, H.-H. Hennies, W. Engelberger, M. Haurand and B. Wilffert (1996) Arzneim.-Forsch./Drug Res. 46 (III), 11, 1029-1036.

The corresponding literature descriptions are hereby introduced in each case as a reference and are deemed to be part of the present disclosure.

The following characteristics were determined for the NA or 5-HT transporter:

NA uptake: $Km$=0.32±0.11 µM

5HT uptake: $Km$=0.084±0.011 µM

II. Method for Determining Affinity for the Batrachotoxin (BTX) Binding Site of the Sodium Channel:

Binding site 2 of the sodium channel is the so-called batrachotoxin (BTX) binding site. [$^3$H]-Batrachotoxinin A20 □benzoate (10 nM in the batch) is used as ligand. The ion channel particles (synaptosomes) are enriched from rat cerebrocortex, as described in the publication by Gray and Whittaker (E. G. Gray and V. P. Whittaker (1962) J. Anat. 76,79-88. The corresponding description is hereby introduced as a reference and is deemed to be part of the present disclosure. The radioactivity measured in the presence of veratridine ($3 \times 10^{-4}$ M in the batch) is defined as non-specific binding.

The assay conditions are as published by Pauwels, Leysen and Laduron, as described in Eur. J. Pharmacol. 124, 291-298. The corresponding description is hereby introduced as a reference and is deemed to be part of the present disclosure.

At variance with this method, the total batch is reduced to 250 µl, such that the assay may be performed on 96-well microtitre plates. The incubation time in these microtitre plates amounts to two hours at room temperature (approx. 20-25° C.).

The following characteristics were determined for the $K_D$ value of the binding site:

$K_D$: 24.63±1.56 nM.

III. Method for Determining Affinity for the mGluR5 Receptor

Pig brain homogenate is produced by homogenisation (Polytron Pt 3000, Kinematica AG, 10,000 rpm (revolutions per minute) for 90 seconds) of pig brain hemispheres without medulla, cerebellum and pons in a buffer of pH 8.0 (30 mM Hepes, Sigma, order number H3375+1 tablet Complete Roche Diagnostics, order number 1836145 made up to 100 ml) in a ratio of 1:20 (brain weight/volume) and differential centrifugation at 900 g and 40,000 g. 450 µg of protein from brain homogenate is incubated in each case in 250 µl incubation batches in 96-well microtitre plates with 15 nM $^3$[H]-MPEP (Tocris, order number R1212) and the compounds to be investigated (in each case 10 µM in the test) in the above-stated buffer at room temperature for 60 minutes.

The batches are then filtered with the assistance of a Brandel Cell Harvester (Brandel, Grade Robotic 9600) on Unifilter plates with glass filter mats (Perkin Elmer, order number 6005177) and then rewashed 3 times with buffer of the above-stated composition using 250 µl per sample. The filter plates are then dried for 60 minutes at 55° C. Then 30 µl of Ultima Gold scintillating material (Packard BioScience, order number 6013159) is added per well and after 3 hours the samples are measured using the B counter (Microbial, Perkin Elmer). Nonspecific binding is determined by the addition of 10 µM 2-methyl-6-(phenylethynyl)-pyridine (Tocris, order number 1212).

The invention is explained below with reference to Examples. These explanations are given merely by way of example and do not restrict the general concept of the invention.

EXAMPLES

The yields of the compounds produced have not been optimised.

All temperatures are uncorrected.

The term "ether" means diethyl ether, "EE" ethyl acetate, "DCM" dichloromethane, "DMF" dimethylformamide, "DME" dimethoxyethane, "DMSO" dimethyl sulfoxide and "THF" tetrahydrofuran. The term "equivalents" means molar equivalents, "mp" melting point or melting range, "decomp." decomposition, "RT" room temperature, i.e. approx. 20° C., "abs." absolute (anhydrous), "rac." racemic, "conc." concentrated, "min" minutes, "h" hours, "d" days, "vol. %" percent by volume and "wt. %" weight percent and "M" is an indication of concentration in mol/l.

Further abbreviations:

| | |
|---|---|
| DIPEA | diisopropylethylamine |
| HOAt | 1-hydroxy-7-azabenzotriazole |
| EDCI | N-ethyl-N'-[3-(dimethylamino)-propyl]-carbodiimide |
| DCC | N,N'-dicyclohexylcarbodiimide |
| DMA | dimethoxymethyl-dimethyl-amine |
| DMAP | dimethylaminopyridine |
| CDI | N,N'-carbonyldiimidazole |
| Pd(C) | palladium on activated carbon |

The chemicals and solvents used were purchased from conventional suppliers (Acros, Avocado, Aldrich, Bachem, Fluka, Lancaster, Maybridge, Merck, Sigma, TCI, Oakwood etc.) or synthesised by conventional methods familiar to the person skilled in the art.

Silica gel 60 (0.040-0.063 mm) from E. Merck, Darmstadt, was used as the stationary phase for the column chromatography.

Thin-layer chromatography was performed with pre-coated silica gel 60 F 254 HPTLC plates from E. Merck, Darmstadt.

The mobile solvent mixture ratios for chromatographic investigations are always stated in volume/volume.

Analysis was carried out by NMR and HPLC-MS.

General method for the production of exemplary substituted 5,6,7,8-tetrahydro-pyrido[4,3-d]pyrimidin-2-yl compounds The synthesis of 2-amino-7,8-dihydro-5H-pyrido[4,3-d]pyrimidine-6-carboxylic acid tert-butyl ester of the formula VI (PG=tert-butyloxycarbonyl, BOC) proceeded as described in detail hereinafter.

In Step 3 the compound VI was acylated by reaction with carboxylic acid chlorides of the general formula $R^3$—(C=O)—Cl or carboxylic acid bromides of the general formula $R^3$—(C=O)—Br, wherein the respective carboxylic acid chloride was optionally produced directly from the corresponding carboxylic acid $R^3$—(C=O)—OH.

To this end, in Step 3 oxalyl chloride (5 equivalents) and a few drops of DMF were added to a solution of the respective carboxylic acid (1 equivalent) in $CH_2Cl_2$ and stirring was performed for 1 h at RT under nitrogen as inert gas. After removal of the solvent, the respective carboxylic acid chloride was dissolved in pyridine. If a carboxylic acid chloride or carboxylic acid bromide was used, this (1 equivalent) was dissolved directly in pyridine.

2-Amino-7,8-dihydro-5H-pyrido[4,3-d]pyrimidine-6-carboxylic acid tert-butyl ester of the formula VI (0.85 equivalents) was added to this solution at 0° C. and stirring was performed for 2 h at 0° C. and then for 2 h at RT under nitrogen as inert gas. After the addition of aqueous 1 M NaOH and stirring for 20 minutes, $CH_2Cl_2$ was added and the aqueous phase extracted with $CH_2Cl_2$. The combined organic phases were dried over $Na_2SO_4$. After filtration and removal of the solvent, purification was performed by means of column chromatography and the respective compound of the general formula VII was obtained.

In Step 4, trifluoroacetic acid (65 equivalents) was added to a solution of the Boc-protected compound of the general formula VII (1 equivalent) in $CH_2Cl_2$ under nitrogen as inert gas and stirring was performed for 2 h at RT. After removal of the solvent, the unprotected compounds of the general formula VIII were obtained, which were used without further working up in Step 5.

In Step 5, acylation of the compounds of the general formula VIII proceeded with carboxylic acid chlorides of the general formula $R^5$—C(=O)—Cl, carboxylic acid bromides

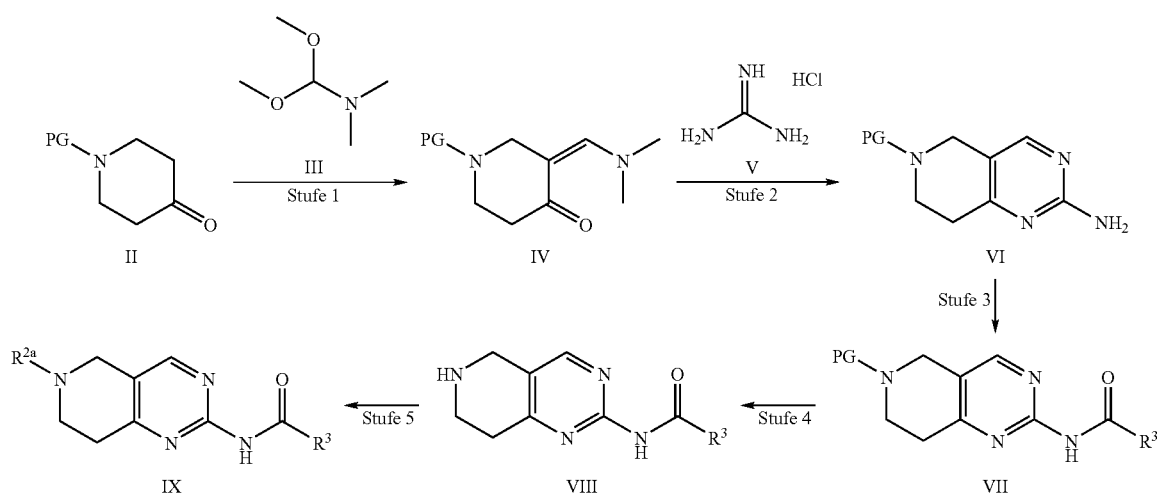

[Stufe = step]

of the general formula $R^5$—C(=O)—Br or by reaction with carboxylic acids of the general formula $R^5$—C(=O)—OH.

For acylation by means of a carboxylic acid in Step 5, the respective compound VIII was dissolved in $CH_2Cl_2$ and DIPEA and the respective carboxylic acid (1 equivalent) were added. After cooling of the reaction mixture to 0° C., EDCI (1 equivalent) and HOAt (20 mg, 0.15 equivalents) were added. The reaction mixture was stirred for 1 h at 0° C. and then overnight at RT. After removal of the solvent, purification proceeded via preparative HPLC or column chromatography and the respective compound of the general formula IX was obtained.

For acylation by means of a carboxylic acid halide, the respective compound of the general formula VIII (1 equivalent) was dissolved in $CH_2Cl_2$, triethylamine (2 equivalents), a catalytic quantity of DMAP and the respective carboxylic acid halide (1 equivalent) were added and then stirring was performed overnight at RT. After removal of the solvent, purification proceeded via preparative HPLC or column chromatography and the respective compound of the general formula IX was obtained.

In Step 5, sulfonylation of the compounds of the general formula VIII proceeded with sulfonyl chlorides of the general formula $R^6$—S(=O)$_2$—Cl.

For sulfonylation, the respective compound of the general formula VIII (1 equivalent) was dissolved in $CH_2Cl_2$ and triethylamine (2 equivalents) and the respective sulfonyl chloride (1 equivalent) were added at 0° C. The reaction mixture was stirred overnight at RT. After removal of the solvent, purification proceeded via preparative HPLC or column chromatography and the respective compound of the general formula IX was obtained.

Hereinafter, the above-described method for the production of substituted 5,6,7,8-tetrahydro-pyrido[4,3-d]pyrimidin-2-yl compounds is explained in detail with reference to a number of exemplary compounds:

Production of 2-amino-7,8-dihydro-5H-pyrido[4,3-d] pyrimidine-6-carboxylic acid tert-butyl ester Dimethoxymethyl-dimethyl-amine (DMA) 35.5 ml (266 mmol) was added to a solution of 4-oxo-piperidine-1-carboxylic acid tert-butyl ester 10.59 g (53.14 mmol) in toluene (50 ml) with stirring and with nitrogen as inert gas and refluxing was performed for 3.5 h. After removal of the solvent, the product 3-dimethylaminomethylene-4-oxo-piperidine-1-carboxylic acid tert-butyl ester was obtained, which was used in the subsequent reaction without further purification.

Guanidine hydrochloride 7.07 g (74 mmol) was added at 0° C. to a solution of sodium 1.65 g (74 mmol) in absolute ethanol and stirring was performed for 2 h at RT under nitrogen as inert gas. 60 ml (60 mmol) of this reaction mixture were added to the solution of 3-dimethylaminomethylene-4-oxo-piperidine-1-carboxylic acid tert-butyl ester in 100 ml of absolute ethanol and refluxing was performed for 5 h. After removal of the solvent and purification by means of column chromatography, 2-amino-7,8-dihydro-5H-pyrido[4,3-d]pyrimidine-6-carboxylic acid tert-butyl ester 5.72 g (43% of theoretical) was obtained.

Example 5

3,5-Dichloro-N-[6-(3-trifluoromethyl-benzoyl)-5,6,7,8-tetrahydro-pyrido[4,3-d]pyrimidin-2-yl]-benzamide a) Production of 2-(3,5-dichloro-benzoylamino)-7,8-dihydro-5H-pyrido[4,3-d]pyrimidine-6-carboxylic acid tert-butyl ester Oxalyl chloride 1184 µl (13.8 mmol) and two drops of DMF were added to a solution of 3,5-dichlorobenzoic acid 527 mg (2.76 mmol) in CH2Cl2 and stirring was performed for 1 h at RT under nitrogen as inert gas. After removal of the solvent, the 3,5-dichlorobenzoyl chloride was dissolved in pyridine (30 ml). 2-Amino-7,8-dihydro-5H-pyrido[4,3-d]pyrimidine-6-carboxylic acid tert-butyl ester 599 mg (2.39 mmol) was added to this solution at 0° C. and stirring was performed for 2 h at 0° C. and then for 2 h at RT under nitrogen as inert gas. After the addition of aqueous 1 M NaOH (40 ml) and stirring for 20 minutes, CH2Cl2 (50 ml) was added and the aqueous phase extracted with CH2Cl2 (3×20 ml). The combined organic phases were dried over Na2SO4. After filtration and removal of the solvent, purification was performed by means of column chromatography and the product 2-(3,5-dichloro-benzoylamino)-7,8-dihydro-5H-pyrido[4,3-d]pyrimidine-6-carboxylic acid tert-butyl ester 573 mg (1.35 mmol, 57% of theoretical) was obtained.

b) 3,5-Dichloro-N-[6-(3-trifluoromethyl-benzoyl)-5,6,7,8-tetrahydro-pyrido[4,3-d]pyrimidin-2-yl]-benzamide Trifluoroacetic acid 5.0 ml (65 mmol) was added to a solution of 2-(3,5-dichloro-benzoylamino)-7,8-dihydro-5H-pyrido[4,3-d]pyrimidine-6-carboxylic acid tert-butyl ester 404 mg (0.954 mmol) in CH2Cl2 (7 ml) under nitrogen as inert gas and stirring was performed for 2 h at RT. After removal of the solvent, the intermediate (3,5-dichloro-N-(5,6,7,8-tetrahydro-pyrido[4,3-d]pyrimidin-2-yl)-benzamide trifluoroacetate) was dissolved in CH2Cl2 (10 ml) and DIPEA 340 µl and 3-trifluoromethylbenzoic acid 200 mg (1.05 mmol) were added. After cooling the reaction mixture to 0° C., EDCI 201 mg (1.05 mmol) and HOAt 20 mg (0.15 mmol) were added. The reaction mixture was stirred for 1 h at 0° C. and then overnight at RT. After removal of the solvent, purification was performed by means of column chromatography and the product 3,5-dichloro-N-[6-(3-trifluoromethyl-benzoyl)-5,6,7,8-tetrahydro-pyrido[4,3-d]pyrimidin-2-yl]-benzamide 260 mg (0.53 mmol, 55% of theoretical) was obtained.

Example 145

N-[6-(3-chloro-thiophene-2-carbonyl)-5,6,7,8-tetrahydro-pyrido[4,3-d]pyrimidin-2-yl]-2-ethoxy-benzamide a) Production of 2-(2-ethoxy-benzoylamino)-7,8-dihydro-5H-pyrido[4,3-d]pyrimidine-6-carboxylic acid tert-butyl ester 2-Amino-7,8-dihydro-5H-pyrido[4,3-d]pyrimidine-6-carboxylic acid tert-butyl ester 528 mg (2.11 mmol) was added at 0° C. to a solution of 2-ethoxybenzoic acid chloride 390 mg (2.11 mmol) in pyridine (25 ml) and stirring was performed for 2 h at 0° C. and then for 72 h at RT under nitrogen as inert gas. After the addition of aqueous 1 M NaOH (40 ml) and stirring for 20 minutes, $CH_2Cl_2$ (50 ml) was added and the aqueous phase extracted with $CH_2Cl_2$ (3×20 ml). The combined organic phases were dried over $Na_2SO_4$. After filtration and removal of the solvent, purification was performed by means of column chromatography and the product 2-(2-ethoxy-benzoylamino)-7,8-dihydro-5H-pyrido[4,3-d]pyrimidine-6-carboxylic acid tert-butyl ester 600 mg (1.51 mmol, 72% of theoretical) was obtained.

b) N-[6-(3-chloro-thiophene-2-carbonyl)-5,6,7,8-tetrahydro-pyrido[4,3-d]pyrimidin-2-yl]-2-ethoxy-benzamide Trifluoroacetic acid 3.6 ml (49 mmol) was added to a solution of 2-(2-ethoxy-benzoylamino)-7,8-dihydro-5H-pyrido[4,3-d]pyrimidine-6-carboxylic acid tert-butyl ester 300 mg (0.753 mmol) in $CH_2Cl_2$ (10 ml) under nitrogen as inert gas and stirring was performed for 2 h at RT. After removal of the solvent, the intermediate (2-ethoxy-N-(5,6,7,8-tetrahydro-pyrido[4,3-d]pyrimidin-2-yl)-benzamide trifluoroacetate) was dissolved in $CH_2Cl_2$ (10 ml) and DIPEA 225 µl and 3-chlorothiophene-2-carboxylic acid 129 mg (0.791 mmol) were added. After cooling the reaction mixture to 0° C., EDCI 158 mg (0.828 mmol) and HOAt 15 mg (0.11 mmol) were added. The reaction mixture was stirred for 1 h at 0° C. and then overnight at RT. After removal of the solvent, purification was performed by means of column chromatography and the product N-[6-(3-chloro-thiophene-2-carbonyl)-5,6,7,8-tetrahydro-pyrido[4,3-d]pyrimidin-2-yl]-2-ethoxy-benzamide 170 mg (0.38 mmol, 51% of theoretical) was obtained.

Example 109

3-Chloro-N-[6-(2-methyl-benzoyl)-5,6,7,8-tetrahydro-pyrido[4,3-d]pyrimidin-2-yl]-benzamide a) Production of 2-(3-chloro-benzoylamino)-7,8-dihydro-5H-pyrido[4,3-d]pyrimidine-6-carboxylic acid tert-butyl ester 2-Amino-7,8-dihydro-5H-pyrido[4,3-d]pyrimidine-6-carboxylic acid tert-butyl ester 1202 mg (4.8 mmol) was added at 0° C. to a solution of 3-chlorobenzoic acid chloride 615 µl (4.8 mmol) in pyridine (25 ml) and stirring was performed for 2 h at 0° C. and then overnight at RT under nitrogen as inert gas. After the addition of aqueous 1 M NaOH (40 ml) and stirring for 20 minutes, $CH_2Cl_2$ (50 ml) was added and the aqueous phase extracted with $CH_2Cl_2$ (3×20 ml). The combined organic phases were dried over $Na_2SO_4$. After filtration and removal of the solvent, purification was performed by means of column chromatography and the product 2-(3-chloro-benzoylamino)-7,8-dihydro-5H-pyrido[4,3-d]pyrimidine-6-carboxylic acid tert-butyl ester 790 mg (2.55 mmol, 53% of theoretical) was obtained.

b) Production of 3-chloro-N-[6-(2-methyl-benzoyl)-5,6,7,8-tetrahydro-pyrido[4,3-d]pyrimidin-2-yl]-benzamide Trifluoroacetic acid 4.0 ml (54 mmol) was added to a solution of 2-(3-chloro-benzoylamino)-7,8-dihydro-5H-pyrido[4,3-d]pyrimidine-6-carboxylic acid tert-butyl ester 307 mg (0.789 mmol) in $CH_2Cl_2$ (8 ml) under nitrogen as inert gas and stirring was performed for 2 h at RT. After removal of the solvent, the intermediate (3-chloro-N-(5,6,7,8-tetrahydro-pyrido[4,3-d]pyrimidin-2-yl)-benzamide trifluoroacetate) was dissolved in $CH_2Cl_2$ (10 ml) and DIPEA 380 µl and 2-methylbenzoic acid 118 mg (0.868 mmol) were added. After cooling the reaction mixture to 0° C., EDCI 166 mg (0.868 mmol) and HOAt 16 mg (0.12 mmol) were added. The reaction mixture was stirred for 1 h at 0° C. and then overnight at RT. After removal of the solvent, purification was performed by means of column chromatography and the product 3-chloro-N-[6-(2-methyl-benzoyl)-5,6,7,8-tetrahydro-pyrido[4,3-d]pyrimidin-2-yl]-benzamide 260 mg (0.64 mmol, 81% of theoretical) was obtained.

Example 121

4-Ethyl-N-[6-(thiophene-3-sulfonyl)-5,6,7,8-tetrahydro-pyrido[4,3-d]pyrimidin-2-yl]-benzamide a) Production of 2-(4-ethyl-benzoylamino)-7,8-dihydro-5H-pyrido[4,3-d]pyrimidine-6-carboxylic acid tert-butyl ester 2-Amino-7,8-dihydro-5H-pyrido[4,3-d]pyrimidine-6-carboxylic acid tert-butyl ester 501 mg (2.0 mmol) was added at 0° C. to a solution of 4-ethylbenzoic acid chloride 296 µl (2.0 mmol) in pyridine (25 ml) and stirring was performed for 2 h at 0° C. and then overnight at RT under nitrogen as inert gas. After the addition of aqueous 1 M NaOH (40 ml) and stirring for 20 minutes, $CH_2Cl_2$ (50 ml) was added and the aqueous phase extracted with $CH_2Cl_2$ (3×20 ml). The combined organic phases were dried over $Na_2SO_4$. After filtration and removal of the solvent, purification was performed by means of column chromatography and the product 2-(4-ethyl-benzoylamino)-7,8-dihydro-5H-pyrido[4,3-d]pyrimidine-6-carboxylic acid tert-butyl ester 640 mg (1.67 mmol, 84% of theoretical) was obtained.

b) Production of 4-ethyl-N-[6-(thiophene-3-sulfonyl)-5,6,7,8-tetrahydro-pyrido[4,3-d]pyrimidin-2-yl]-benzamide Trifluoroacetic acid 7.3 ml (96 mmol) was added to a solution of 2-(4-ethyl-benzoylamino)-7,8-dihydro-5H-pyrido[4,3-d]pyrimidine-6-carboxylic acid tert-butyl ester 567 mg (1.48 mmol) in $CH_2Cl_2$ (10 ml) under nitrogen as inert gas and stirring was performed for 1.5 h at RT. After removal of the solvent, the intermediate (4-ethyl-N-(5,6,7,8-tetrahydro-pyrido[4,3-d]pyrimidin-2-yl)-benzamide trifluoroacetate) was dissolved in $CH_2Cl_2$ (10 ml). After the addition of triethylamine 1150 µl (8.20 mmol), the solution was cooled to 0° C. and 3-thiophene sulfonyl chloride 253 mg (1.39 mmol) was added. The reaction mixture was stirred for 1 h at 0° C. and then overnight at RT. After removal of the solvent, purification was performed by means of column chromatography and the product 4-ethyl-N-[6-(thiophene-3-sulfonyl)-5,6,7,8-tetrahydro-pyrido[4,3-d]pyrimidin-2-yl]-benzamide 400 mg (0.93 mmol, 63% of theoretical) was obtained.

Example 125

N-[6-(3-bromo-benzenesulfonyl)-5,6,7,8-tetrahydro-pyrido[4,3-d]pyrimidin-2-yl]-3-chloro-benzamide a) Production of 2-(3-chloro-benzoylamino)-7,8-dihydro-5 H-pyrido[4,3-d]pyrimidine-6-carboxylic acid tert-butyl ester 2-Amino-7,8-dihydro-5H-pyrido[4,3-d]pyrimidine-6-carboxylic acid tert-butyl ester 1202 mg (4.8 mmol) was added at 0° C. to a solution of 3-chlorobenzoic acid chloride 615 μl (4.8 mmol) in pyridine (25 ml) and stirring was performed for 2 h at 0° C. and then overnight at RT under nitrogen as inert gas. After the addition of aqueous 1 M NaOH (40 ml) and stirring for 20 minutes, $CH_2Cl_2$ (50 ml) was added and the aqueous phase extracted with $CH_2Cl_2$ (3×20 ml). The combined organic phases were dried over $Na_2SO_4$. After filtration and removal of the solvent, purification was performed by means of column chromatography and the product 2-(3-chloro-benzoylamino)-7,8-dihydro-5H-pyrido[4,3-d]pyrimidine-6-carboxylic acid tert-butyl ester 790 mg (2.55 mmol, 53% of theoretical) was obtained.

b) Production of N-[6-(3-bromo-benzenesulfonyl)-5,6,7,8-tetrahydro-pyrido[4,3-d]pyrimidin-2-yl]-3-chloro-benzamide Trifluoroacetic acid 6.2 ml (81 mmol) was added to a solution of 2-(3-chloro-benzoylamino)-7,8-dihydro-5H-pyrido[4,3-d]pyrimidine-6-carboxylic acid tert-butyl ester 487 mg (1.25 mmol) in $CH_2Cl_2$ (8 ml) under nitrogen as inert gas and stirring was performed for 1.5 h at RT. After removal of the solvent, the intermediate (3-chloro-N-(5,6,7,8-tetrahydro-pyrido[4,3-d]pyrimidin-2-yl)-benzamide trifluoroacetate) was dissolved in $CH_2Cl_2$ (15 ml). After the addition of triethylamine 820 μl (5.84 mmol), the solution was cooled to 0° C. and 3-bromo benzenesulfonyl chloride 311 mg (1.37 mmol) was added. The reaction mixture was stirred for 1 h at 0° C. and then overnight at RT. After removal of the solvent, purification was performed by means of column chromatography and the product N-[6-(3-bromo-benzenesulfonyl)-5,6,7,8-tetrahydro-pyrido[4,3-d]pyrimidin-2-yl]-3-chloro-benzamide 525 mg (81% of theoretical) was obtained.

General method for the production of substituted 5,6,7,8-tetrahydro-quinazolin-2-yl compounds

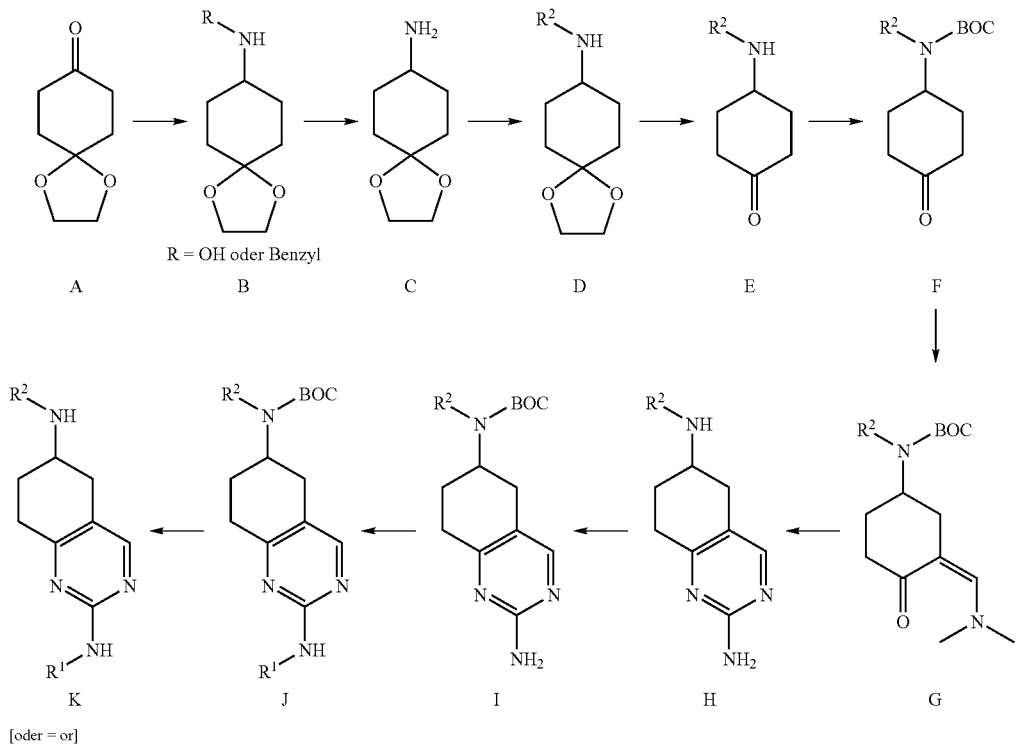

[oder = or]

The synthesis of 1,4-dioxa-spiro[4.5]dec-8-ylamine of the formula C proceeded as described in detail hereinafter.

Sulfonylation of 1,4-dioxa-spiro[4.5]dec-8-ylamine of the formula C proceeded by means of sulfonyl chlorides of the general formula $R^6$—$S(=O)_2$—Cl.

For sulfonylation, $K_2CO_3$ (5 equivalents) was added to a solution of 1,4-dioxa-spiro[4.5]dec-8-ylamine of the formula C (1 equivalent) in $CH_3CN$. A solution of the respective sulfonyl chloride (1 equivalent) in $CH_3CN$ was added and stirring was performed at RT for 2 h under nitrogen as inert gas. The reaction mixture was filtered and the residue washed with $CH_2Cl_2$. After purification by column chromatography, the respective compound of the general formula D was obtained.

Alternatively, for sulfonylation, triethylamine (2 equivalents) and the respective sulfonyl chloride (1 equivalent) were added at 0° C. to a solution of 1,4-dioxa-spiro[4.5]dec-8-ylamine of the formula C (1 equivalent) in $CH_2Cl_2$. The reaction mixture was stirred overnight at RT. The respective compound of the general formula D was obtained after removal of the solvent and purification by means of preparative HPLC or column chromatography.

Acylation of the compounds C proceeded with carboxylic acid chlorides of the general formula $R^5$—C(=O)—Cl, carboxylic acid bromides of the general formula R⁵—C(=O)—Br or by reaction with carboxylic acids of the general formula R⁵—C(=O)—OH.

For acylation by means of a carboxylic acid, the compound C (1 equivalent) was dissolved in $CH_2Cl_2$ and DIPEA and the respective carboxylic acid (1 equivalent) were added. After cooling of the reaction mixture to 0° C., EDCI (1 equivalent) and HOAt (0.15 equivalents) were added. The reaction mixture was stirred for 1 h at 0° C. and then overnight at RT. After removal of the solvent, the respective compound of the formula D was purified by means of column chromatography.

For acylation by means of a carboxylic acid halide, the respective compound of the general formula D (1 equivalent) was dissolved in $CH_2Cl_2$, triethylamine (2 equivalents), a catalytic quantity of DMAP and the respective carboxylic acid halide (1 equivalent) were added and then stirring was performed overnight at RT. After removal of the solvent and purification by means of column chromatography, the respective compound of the general formula D was obtained.

Reaction to yield the compounds of the formulae D to I proceeded as described in detail hereinafter.

Reaction of the respective compound I to yield the compounds J proceeded by acylation with carboxylic acid chlorides of the general formula R³—(C=O)—Cl, carboxylic acid bromides of the general formula R³—(C=O)—Br or by reaction with carboxylic acids of the general formula R³—(C=O)—OH.

For acylation by means of a carboxylic acid, the respective compound I (1 equivalent) was dissolved in $CH_2Cl_2$ and DIPEA and the respective carboxylic acid (1 equivalent) were added. After cooling of the reaction mixture to 0° C., EDCI (1 equivalent) and HOAt (0.15 equivalents) were added. The reaction mixture was stirred for 1 h at 0° C. and then overnight at RT. After removal of the solvent, the respective compound of the general formula J was purified by means of column chromatography.

For acylation by means of a carboxylic acid halide, the respective compound of the general formula I (1 equivalent) was dissolved in $CH_2Cl_2$, triethylamine (2 equivalents), a catalytic quantity of DMAP and the respective carboxylic acid halide (1 equivalent) were added and then stirring was performed overnight at RT. After removal of the solvent and purification by means of column chromatography, the respective compound of the general formula J was obtained.

Final elimination of the BOC protective group proceeded as described in detail hereinafter.

Example 180

Thiophene-2-carboxylic acid [6-(2,5-dichloro-thiophene-3-sulfonylamino)-5,6,7,8-tetrahydro-quinazolin-2-yl]-amide a) Production of benzyl-(1,4-dioxa-spiro[4.5]dec-8-yl)-amine $Na(OAc)_3BH$ 2.03 g (9.6 mmol) was added to a solution of 1,4-dioxa-spiro[4.5]decan-8-one 1.0 g (6.4 mmol) and benzylamine 0.69 g (6.4 mmol) in $CH_2Cl_2$ (20 ml) under nitrogen as inert gas and stirring was performed for 2 h at RT. After the addition of $CH_2Cl_2$ (80 ml), the organic phase was washed with aqueous saturated $NaHCO_3$ solution. After drying of the separated organic phases over $Na_2SO_4$ and filtration, the solvent was removed by distillation and the product benzyl-(1,4-dioxa-spiro[4.5]dec-8-yl)-amine 1.6 g (100% of theoretical) was obtained.

b) Production of 1,4-dioxa-spiro[4.5]dec-8-ylamine

Benzyl-(1,4-dioxa-spiro[4.5]dec-8-yl)-amine (6.4 mmol) was dissolved in EtOH (10 ml) and hydrogenated under nitrogen with Pd(C) 340 mg (0.32 mmol) with stirring overnight at RT. The reaction mixture was filtered out over Celite and washed with $CH_2Cl_2$. After removal of the solvent, the product 1,4-dioxa-spiro[4.5]dec-8-ylamine 824 mg (82% of theoretical) was obtained.

c) Production of 2,5-dichloro-thiophene-3-sulfonic acid (1,4-dioxa-spiro[4.5]dec-8-yl)-amide $K_2CO_3$ 2.51 g (18.16 mmol) was added to a solution of 1,4-dioxa-spiro[4.5]dec-8-ylamine 571 mg (3.63 mmol) in $CH_3CN$ (10 ml). A solution of 3,5-dichlorothiophene-3-sulfonylchloride (914 mg, 3.63 mmol) in $CH_3CN$ (10 ml) was added and stirring was performed at RT for 100 min under nitrogen as inert gas. The reaction mixture was filtered and the residue washed with $CH_2Cl_2$. After purification by column chromatography, the 2,5-dichloro-thiophene-3-sulfonic acid (1,4-dioxa-spiro[4.5]dec-8-yl)-amide 914 mg (68% of theoretical) was obtained.

d) Production of 2,5-dichloro-thiophene-3-sulfonic acid (4-oxo-cyclohexyl)-amide p-TosOH×$H_2O$ 4 g (21.0 mmol) was added to a solution of 2,5-dichloro-thiophene-3-sulfonic acid-(1,4-dioxa-spiro[4.5]dec-8-yl)-amide 894 mg (2.40 mmol) in acetone (10 ml) and water (1 ml) and stirring was performed for 6 h at RT. After addition of aqueous 1M NaOH (100 ml) and aqueous saturated NaCl solution (100 ml), extraction was performed with $CH_2Cl_2$ (3×200 ml). After separation of the organic phases, drying over $Na_2SO_4$ and filtration, the solvent was removed by distillation. After purification by means of column chromatography, the product 2,5-dichloro-thiophene-3-sulfonic acid (4-oxo-cyclohexyl)-amide 634 mg (80% of theoretical) was obtained.

e) Production of N-Boc-protected 2,5-dichloro-thiophene-3-sulfonic acid (4-oxo-cyclohexyl)-amide $Et_3N$ 179 mg (1.77 mmol) and DMAP 29 mg (0.24 mmol) were added to a solution of 2,5-dichloro-thiophene-3-sulfonic acid (4-oxo-cyclohexyl)-amide 388 mg (1.18 mmol) in $CH_2Cl_2$ (10 ml). After cooling to 0° C., $Boc_2O$ 386 mg (1.77 mmol) was added and stirring was performed for 2 h under nitrogen as inert gas. After removal of the solvent and purification by means of column chromatography, the product N-Boc-protected 2,5-dichloro-thiophene-3-sulfonic acid (4-oxo-cyclohexyl)-amide 419 mg (83% of theoretical) was obtained.

f) Production of 2,5-dichloro-thiophene-3-sulfonic acid (2-amino-5,6,7,8-tetrahydro-quinazoline-6-yl)-amide A reaction solution of N-Boc-protected 2,5-dichloro-thiophene-3-sulfonic acid (4-oxo-cyclohexyl)-amide 383 mg (0.89 mmol) and dimethoxymethyl-dimethyl-amine 533 mg (4.47 mmol) in toluene (10 ml) was refluxed for 4 h with stirring and nitrogen as inert gas. After removal of the solvent, the crude product N-Boc-protected 2,5-dichloro-thiophene-3-sulfonic acid (3-dimethylaminomethylene-4-oxo-cyclohexyl)-amide was obtained, which was used without further purification in the next step.

Guanidine hydrochloride 245 mg (2.56 mmol) was added to a solution of sodium 59 mg (2.6 mmol) in absolute ethanol (26 ml) and stirring was performed for 30 min at RT under nitrogen as inert gas. 9 ml (60 mmol) of this reaction mixture was added to N-Boc-protected 2,5-dichloro-thiophene-3-sulfonic acid (3-dimethylaminomethylene-4-oxo-cyclohexyl)-amide (0.89 mmol) and refluxing was performed for 8 h under nitrogen as inert gas. After the addition of $CH_2Cl_2$ (5 ml) and TFA (5 ml) and stirring for 1 h at RT and removal of the solvent, purification was performed by means of column chromatography and the product 2,5-dichloro-thiophene-3-sulfonic acid (2-amino-5,6,7,8-tetrahydro-quinazolin-6-yl)-amide 133 mg (39% of theoretical) was obtained.

g) Production of N-Boc-protected 2,5-dichloro-thiophene-3-sulfonic acid (2-amino-5,6,7,8-tetrahydro-quinazolin-6-yl)-amide $Boc_2O$ 41 mg (0.188 mmol) and DMAP 2 mg (0.016 mmol) was added at 0° C. to a solution of 2,5-dichloro-thiophene-3-sulfonic acid (2-amino-5,6,7,8-tetrahydro-quinazolin-6-yl)-amide 63 mg (0.17 mmol) in CH2Cl2 (10 ml) and stirring was performed under nitrogen as inert gas for 3.5 h at 0° C. After the addition of Boc2O 20 mg and stirring for 30 min at 0° C., the solvent was removed by distillation. After purification by means of column chromatography, the product N-Boc-protected 2,5-dichloro-thiophene-3-sulfonic acid (2-amino-5,6,7,8-tetrahydro-quinazolin-6-yl)-amide 58 mg (73% of theoretical) was obtained.

h) Production of N-Boc-protected thiophene-2-carboxylic acid [6-(2,5-dichloro-thiophene-3-sulfonylamino)-5,6,7,8-tetrahydro-quinazolin-2-yl]-amide Thiophene-2-carboxylic acid chloride 25 mg (0.17 mmol) dissolved in $CH_2Cl_2$ (1 ml) was added at 0° C. to a solution of N-Boc-protected 2,5-dichloro-thiophene-3-sulfonic acid (2-amino-5,6,7,8-tetrahydro-quinazolin-6-yl)-amide 54 mg (0.11 mmol) in $CH_2Cl_2$ (4 ml) and pyridine (5 ml) and stirring was performed for 1 h at 0° C. and overnight at RT and under nitrogen as inert gas. After removal of the solvent and purification by means of column chromatography, the product N-Boc-protected thiophene-2-carboxylic acid [6-(2,5-dichloro-thiophene-3-sulfonylamino)-5,6,7,8-tetrahydro-quinazolin-2-yl]-amide 21 mg (32% of theoretical) was obtained.

i) Production of thiophene-2-carboxylic acid [6-(2,5-dichloro-thiophene-3-sulfonylamino)-5,6,7,8-tetrahydro-quinazolin-2-yl]-amide TFA (2 ml) was added to a solution of N-Boc-protected thiophene-2-carboxylic acid [6-(2,5-dichloro-thiophene-3-sulfonylamino)-5,6,7,8-tetrahydro-quinazolin-2-yl]-amide 21 mg (36 µmol) in $CH_2Cl_2$ (1 ml) and stirring was performed for 2 h at RT. After removal of the solvent and purification by means of column chromatography, the product thiophene-2-carboxylic acid [6-(2,5-dichloro-thiophene-3-sulfonylamino)-5,6,7,8-tetrahydro-quinazolin-2-yl]-amide 12 mg (69% of theoretical) was obtained.

The production, not described in detail above, of the other compounds according to the Examples stated below also proceeded in accordance with the above-stated production methods, wherein the educts used in each case are known to the person skilled in the art on the basis of these methods.

| Example | Compound |
|---|---|
| 1 | 3-fluoro-N-[6-(4-fluoro-benzoyl)-5,6,7,8-tetrahydro-pyrido[4,3-d]pyrimidin-2-yl]-benzamide |
| 2 | 3,5-dichloro-N-[6-(3-fluoro-4-methoxy-benzoyl)-5,6,7,8-tetrahydro-pyrido[4,3-d]pyrimidin-2-yl]-benzamide |
| 3 | 4-tert-butyl-N-(6-hexanoyl-5,6,7,8-tetrahydro-pyrido[4,3-d]pyrimidin-2-yl)-benzamide |
| 4 | N-(6-acetyl-5,6,7,8-tetrahydro-pyrido[4,3-d]pyrimidin-2-yl)-3,4-dichloro-benzamide |
| 5 | 3,5-dichloro-N-[6-(3-trifluoromethyl-benzoyl)-5,6,7,8-tetrahydro-pyrido[4,3-d]pyrimidin-2-yl]-benzamide |
| 6 | 3-chloro-N-[6-(4-methoxy-2,3,6-trimethyl-benzenesulfonyl)-5,6,7,8-tetrahydro-pyrido[4,3-d]pyrimidin-2-yl]-benzamide |
| 7 | N-[6-(2-ethoxy-benzoyl)-5,6,7,8-tetrahydro-pyrido[4,3-d]pyrimidin-2-yl]-3-fluoro-benzamide |
| 8 | 3-chloro-N-[6-(3-phenyl-propionyl)-5,6,7,8-tetrahydro-pyrido[4,3-d]pyrimidin-2-yl]-benzamide |
| 9 | 4-tert-butyl-N-[6-(isoxazole-5-carbonyl)-5,6,7,8-tetrahydro-pyrido[4,3-d]pyrimidin-2-yl]-benzamide |
| 10 | N-[6-(2-benzylsulfanyl-acetyl)-5,6,7,8-tetrahydro-pyrido[4,3-d]pyrimidin-2-yl]-2-methoxy-benzamide |
| 11 | thiophene-2-carboxylic acid {6-[2-(4-chloro-phenyl)-2-methyl-propionyl]-5,6,7,8-tetrahydro-pyrido[4,3-d]pyrimidin-2-yl}-amide |
| 12 | N-(6-benzoyl-5,6,7,8-tetrahydro-pyrido[4,3-d]pyrimidin-2-yl)-3-methyl-benzamide |
| 13 | N-[6-(2,3-dihydro-benzofuran-5-carbonyl)-5,6,7,8-tetrahydro-pyrido[4,3-d]pyrimidin-2-yl]-2-fluoro-benzamide |
| 14 | thiophene-2-carboxylic acid [6-(3,4,5-trimethoxy-benzoylamino)-5,6,7,8-tetrahydro-quinazolin-2-yl]-amide |
| 15 | naphthalene-1-carboxylic acid [6-(3-methyl-5-phenyl-isoxazole-4-carbonyl)-5,6,7,8-tetrahydro-pyrido[4,3-d]pyrimidin-2-yl]-amide |
| 16 | 3-chloro-N-{6-[2-(5-methyl-2-phenyl-thiazol-4-yl)-acetyl]-5,6,7,8-tetrahydro-pyrido[4,3-d]pyrimidin-2-yl}-benzamide |

-continued

| Example | Compound |
|---|---|
| 17 | N-[6-(4-chloro-2,5-dimethyl-benzenesulfonyl)-5,6,7,8-tetrahydro-pyrido[4,3-d]pyrimidin-2-yl]-2-trifluoromethyl-benzamide |
| 18 | N-[6-(1-benzenesulfonyl-1H-indole-2-carbonyl)-5,6,7,8-tetrahydro-pyrido[4,3-d]pyrimidin-2-yl]-3-methoxy-benzamide |
| 20 | N-[6-(5-methyl-1-phenyl-1H-pyrazole-4-sulfonyl)-5,6,7,8-tetrahydro-pyrido[4,3-d]pyrimidin-2-yl]-2-trifluoromethyl-benzamide |
| 21 | N-[6-(3-chloro-2-methyl-benzenesulfonyl)-5,6,7,8-tetrahydro-pyrido[4,3-d]pyrimidin-2-yl]-3-fluoro-benzamide |
| 22 | 3,5-dichloro-N-[6-(3,5-dimethyl-isoxazole-4-carbonyl)-5,6,7,8-tetrahydro-pyrido[4,3-d]pyrimidin-2-yl]-benzamide |
| 23 | thiophene-2-carboxylic acid [6-(4-trifluoromethoxy-benzenesulfonylamino)-5,6,7,8-tetrahydro-quinazolin-2-yl]-amide |
| 25 | N-[6-(furan-2-carbonyl)-5,6,7,8-tetrahydro-pyrido[4,3-d]pyrimidin-2-yl]-3-methoxy-benzamide |
| 26 | N-{6-[4-(2,3-dihydro-indol-1-yl)-4-oxo-butyryl]-5,6,7,8-tetrahydro-pyrido[4,3-d]pyrimidin-2-yl}-3-methyl-benzamide |
| 27 | N-{6-[2-(4-methyl-cyclohexyl)-acetyl]-5,6,7,8-tetrahydro-pyrido[4,3-d]pyrimidin-2-yl}-2-trifluoromethyl-benzamide |
| 28 | 3,4-difluoro-N-[6-(6-phenoxy-pyridine-3-carbonyl)-5,6,7,8-tetrahydro-pyrido[4,3-d]pyrimidin-2-yl]-benzamide |
| 29 | 4-tert-butyl-N-[6-(2-phenyl-thiazole-4-carbonyl)-5,6,7,8-tetrahydro-pyrido[4,3-d]pyrimidin-2-yl]-benzamide |
| 30 | 3,5-dichloro-N-[6-(2-trifluoromethyl-benzenesulfonyl)-5,6,7,8-tetrahydro-pyrido[4,3-d]pyrimidin-2-yl]-benzamide |
| 31 | thiophene-2-carboxylic acid [6-(3-bromo-benzenesulfonylamino)-5,6,7,8-tetrahydro-quinazolin-2-yl]-amide |
| 32 | N-[6-(2-chloro-pyridine-4-carbonyl)-5,6,7,8-tetrahydro-pyrido[4,3-d]pyrimidin-2-yl]-3-methoxy-benzamide |
| 33 | 4-fluoro-N-[6-(2-methanesulfonyl-benzenesulfonylamino)-5,6,7,8-tetrahydro-quinazolin-2-yl]-benzamide |
| 35 | N-(6-dimethylsulfamoyl-5,6,7,8-tetrahydro-pyrido[4,3-(d)]pyrimidin-2-yl)-3-fluoro-benzamide |
| 36 | 3-fluoro-N-{6-[2-(4-trifluoromethyl-phenyl)-acetyl]-5,6,7,8-tetrahydro-pyrido[4,3-(d)]pyrimidin-2-yl}-benzamide |
| 37 | N-{6-[2-(1,3-dioxo-1,3-dihydro-isoindol-2-yl)-acetyl]-5,6,7,8-tetrahydro-pyrido[4,3-(d)]pyrimidin-2-yl}-2-trifluoromethyl-benzamide |
| 38 | thiophene-2-carboxylic acid {6-[4-(4-chloro-2-methyl-phenoxy)-butyrylamino]-5,6,7,8-tetrahydro-quinazolin-2-yl}-amide |
| 39 | N-[6-(butane-1-sulfonyl)-5,6,7,8-tetrahydro-pyrido[4,3-(d)]pyrimidin-2-yl]-3-fluoro-benzamide |
| 40 | 2-methoxy-N-[6-(2-propyl-pentanoyl)-5,6,7,8-tetrahydro-pyrido[4,3-d]pyrimidin-2-yl]-benzamide |
| 41 | N-[6-(4,5-dichloro-thiophene-2-sulfonylamino)-5,6,7,8-tetrahydro-quinazolin-2-yl]-4-fluoro-benzamide |
| 42 | 4-chloro-N-[6-(2-trifluoromethyl-benzenesulfonyl)-5,6,7,8-tetrahydro-pyrido[4,3-d]pyrimidin-2-yl]-benzamide |
| 43 | thiophene-2-carboxylic acid [6-(4-methoxy-benzenesulfonylamino)-5,6,7,8-tetrahydro-quinazolin-2-yl]-amide |
| 44 | 5-[2-(3,4-difluoro-benzoylamino)-7,8-dihydro-5H-pyrido[4,3-(d)]pyrimidin-6-yl]-5-oxo-valeric acid methyl ester |
| 45 | N-[6-(benzo[b]thiophene-3-carbonyl)-5,6,7,8-tetrahydro-pyrido[4,3-d]pyrimidin-2-yl]-4-chloro-benzamide |
| 46 | N-[6-(5-bromo-2-methoxy-benzenesulfonylamino)-5,6,7,8-tetrahydro-quinazolin-2-yl]-4-fluoro-benzamide |
| 47 | 4-fluoro-N-[6-(4-fluoro-benzenesulfonylamino)-5,6,7,8-tetrahydro-quinazolin-2-yl]-benzamide |
| 48 | N-{6-[2-(1H-indol-3-yl)-2-oxo-acetyl]-5,6,7,8-tetrahydro-pyrido[4,3-d]pyrimidin-2-yl}-2-trifluoromethyl-benzamide |
| 49 | 5-tert-butyl-2-methyl-furan-3-carboxylic acid {2-[(thiophene-2-carbonyl)-amino]-5,6,7,8-tetrahydro-quinazolin-6-yl}-amide |
| 50 | N-[6-(2,5-dimethoxy-benzenesulfonyl)-5,6,7,8-tetrahydro-pyrido[4,3-d]pyrimidin-2-yl]-3-methoxy-benzamide |
| 51 | benzoic acid 2-{2-[(thiophene-2-carbonyl)-amino]-5,6,7,8-tetrahydro-quinazolin-6-ylcarbamoyl}-benzyl ester |
| 52 | 3,4-difluoro-N-(6-hexanoyl-5,6,7,8-tetrahydro-pyrido[4,3-(d)]pyrimidin-2-yl)-benzamide |
| 53 | 4-ethyl-N-[6-(tetrahydro-furan-2-carbonyl)-5,6,7,8-tetrahydro-pyrido[4,3-d]pyrimidin-2-yl]-benzamide |
| 54 | N-[6-(2-chloro-benzenesulfonyl)-5,6,7,8-tetrahydro-pyrido[4,3-d]pyrimidin-2-yl]-3-fluoro-benzamide |
| 55 | 4-tert-butyl-N-[6-(5-tert-butyl-2-methyl-2H-pyrazole-3-carbonyl)-5,6,7,8-tetrahydro-pyrido[4,3-d]pyrimidin-2-yl]-benzamide |
| 56 | 3-methoxy-N-[6-(4-methoxy-benzenesulfonyl)-5,6,7,8-tetrahydro-pyrido[4,3-d]pyrimidin-2-yl]-benzamide |
| 57 | {2-[2-(3,4-difluoro-benzoylamino)-7,8-dihydro-5H-pyrido[4,3-d]pyrimidin-6-yl]-2-oxo-1-phenyl-ethyl}-carbamic acid benzyl ester |

-continued

| Example | Compound |
|---|---|
| 58 | 5-phenyl-oxazole-4-carboxylic acid {2-[(thiophene-2-carbonyl)-amino]-5,6,7,8-tetrahydro-quinazolin-6-yl}-amide |
| 59 | 4-chloro-N-(6-dimethylsulfamoyl-5,6,7,8-tetrahydro-pyrido[4,3-d]pyrimidin-2-yl)-benzamide |
| 60 | 4-tert-butyl-N-[6-(2-fluoro-benzenesulfonyl)-5,6,7,8-tetrahydro-pyrido[4,3-d]pyrimidin-2-yl]-benzamide |
| 61 | 4-chloro-N-[6-(3-cyclopentyl-propionyl)-5,6,7,8-tetrahydro-pyrido[4,3-d]pyrimidin-2-yl]-benzamide |
| 62 | 4-chloro-N-[6-(4-phenyl-butyryl)-5,6,7,8-tetrahydro-pyrido[4,3-d]pyrimidin-2-yl]-benzamide |
| 63 | 4-tert-butyl-N-[6-(5-methyl-2-phenyl-2H-[1,2,3]triazole-4-carbonyl)-5,6,7,8-tetrahydro-pyrido[4,3-d]pyrimidin-2-yl]-benzamide |
| 64 | 2-chloro-N-{2-[(thiophene-2-carbonyl)-amino]-5,6,7,8-tetrahydro-quinazolin-6-yl}-isonicotinamide |
| 66 | N-[6-(5-chloro-thiophene-2-sulfonyl)-5,6,7,8-tetrahydro-pyrido[4,3-d]pyrimidin-2-yl]-3-fluoro-benzamide |
| 67 | N-[6-(4-diethylamino-benzoyl)-5,6,7,8-tetrahydro-pyrido[4,3-d]pyrimidin-2-yl]-3-methoxy-benzamide |
| 68 | N-[6-(2,4-dimethyl-thiazole-5-sulfonyl)-5,6,7,8-tetrahydro-pyrido[4,3-d]pyrimidin-2-yl]-3-methyl-benzamide |
| 69 | 4-chloro-N-[6-naphthalene-2-carbonyl)-5,6,7,8-tetrahydro-pyrido[4,3-d]pyrimidin-2-yl]-benzamide |
| 70 | N-[6-(2,4-difluoro-benzenesulfonyl)-5,6,7,8-tetrahydro-pyrido[4,3-d]pyrimidin-2-yl]-2-methoxy-benzamide |
| 71 | 3,4-dichloro-N-[6-(4-chloro-benzenesulfonyl)-5,6,7,8-tetrahydro-pyrido[4,3-d]pyrimidin-2-yl]-benzamide |
| 72 | 3,4-difluoro-N-[6-(thiophene-2-sulfonyl)-5,6,7,8-tetrahydro-pyrido[4,3-d]pyrimidin-2-yl]-benzamide |
| 74 | 4-ethyl-N-[6-(4-pyrazol-1-yl-benzoyl)-5,6,7,8-tetrahydro-pyrido[4,3-d]pyrimidin-2-yl]-benzamide |
| 75 | N-[6-(7,7-dimethyl-2-oxo-bicyclo[2.2.1]hept-1-ylmethanesulfonylamino)-5,6,7,8-tetrahydro-quinazolin-2-yl]-butyramide |
| 76 | 5-oxo-5-phenyl-valeric acid (2-butyrylamino-5,6,7,8-tetrahydro-quinazolin-6-yl)-amide |
| 77 | 3-[2-(4-chloro-benzoylamino)-7,8-dihydro-5H-pyrido[4,3-d]pyrimidin-6-yl]-3-oxo-propionic acid methyl ester |
| 78 | N-{6-[5-(4-chloro-phenyl)-2-methyl-furan-3-carbonyl]-5,6,7,8-tetrahydro-pyrido[4,3-d]pyrimidin-2-yl}-2-methoxy-benzamide |
| 79 | 4-chloro-N-[6-(2,4-dimethyl-thiazole-5-sulfonyl)-5,6,7,8-tetrahydro-pyrido[4,3-d]pyrimidin-2-yl]-benzamide |
| 80 | N-[6-(2,3-difluoro-benzoyl)-5,6,7,8-tetrahydro-pyrido[4,3-d]pyrimidin-2-yl]-3-methoxy-benzamide |
| 81 | 4-chloro-N-{6-[2-(2-methoxy-ethoxy)-acetyl]-5,6,7,8-tetrahydro-pyrido[4,3-d]pyrimidin-2-yl}-benzamide |
| 82 | 2-[2-(2-ethoxy-benzoylamino)-7,8-dihydro-5H-pyrido[4,3-d]pyrimidine-6-sulfonyl]-benzoic acid methyl ester |
| 83 | 4-tert-butyl-N-[6-(4-nitro-benzenesulfonyl)-5,6,7,8-tetrahydro-pyrido[4,3-d]pyrimidin-2-yl]-benzamide |
| 86 | N-[6-(5-chloro-thiophene-2-sulfonyl)-5,6,7,8-tetrahydro-pyrido[4,3-d]pyrimidin-2-yl]-2-methoxy-benzamide |
| 87 | 4-fluoro-N-[6-(furan-2-carbonyl)-5,6,7,8-tetrahydro-pyrido[4,3-d]pyrimidin-2-yl]-benzamide |
| 88 | 4-{2-[(thiophene-2-carbonyl)-amino]-5,6,7,8-tetrahydro-quinazolin-6-ylcarbamoyl}-piperidine-1-carboxylic acid tert-butyl ester |
| 89 | 1-(4-chloro-phenyl)-cyclopropanecarboxylic acid (2-butyrylamino-5,6,7,8-tetrahydro-quinazolin-6-yl)-amide |
| 90 | N-(6-ethanesulfonyl-5,6,7,8-tetrahydro-pyrido[4,3-d]pyrimidin-2-yl)-3-methoxy-benzamide |
| 91 | 5-methyl-thiophene-2-carboxylic acid (2-butyrylamino-5,6,7,8-tetrahydro-quinazolin-6-yl)-amide |
| 92 | 4-tert-butyl-N-[6-(4-methyl-3-nitro-benzoyl)-5,6,7,8-tetrahydro-pyrido[4,3-d]pyrimidin-2-yl]-benzamide |
| 94 | 4-fluoro-N-[6-(3-phenyl-propionylamino)-5,6,7,8-tetrahydro-quinazolin-2-yl]-benzamide |
| 95 | 3,4-dichloro-N-[6-(2,4,6-trimethyl-benzenesulfonyl)-5,6,7,8-tetrahydro-pyrido[4,3-d]pyrimidin-2-yl]-benzamide |
| 96 | N-[6-(4-methyl-3,4-dihydro-2H-benzo[1,4]oxazine-7-sulfonyl)-5,6,7,8-tetrahydro-pyrido[4,3-d]pyrimidin-2-yl]-nicotinamide |
| 97 | thiophene-2-carboxylic acid [6-(3,5-difluoro-benzoylamino)-5,6,7,8-tetrahydro-quinazolin-2-yl]-amide |
| 98 | N-[6-(2,4-difluoro-benzenesulfonylamino)-5,6,7,8-tetrahydro-quinazolin-2-yl]-butyramide |
| 99 | thiophene-2-carboxylic acid [6-(2,3,5,6-tetramethyl-benzenesulfonyl)-5,6,7,8-tetrahydro-pyrido[4,3-d]pyrimidin-2-yl]-amide |
| 101 | N-[6-(3,4-dichloro-benzoyl)-5,6,7,8-tetrahydro-pyrido[4,3-d]pyrimidin-2-yl]-4-ethyl-benzamide |

-continued

| Example | Compound |
|---|---|
| 102 | N-[6-(7,7-dimethyl-2-oxo-bicyclo[2.2.1]hept-1-ylmethanesulfonyl)-5,6,7,8-tetrahydro-pyrido[4,3-d]pyrimidin-2-yl]-3-fluoro-benzamide |
| 103 | N-[6-(6-fluoro-4H-benzo[1,3]dioxin-8-carbonyl)-5,6,7,8-tetrahydro-pyrido[4,3-d]pyrimidin-2-yl]-2-trifluoromethyl-benzamide |
| 104 | [5-(2-butyrylamino-5,6,7,8-tetrahydro-quinazolin-6-ylcarbamoyl)-pentyl]-carbamic acid benzyl ester |
| 105 | 2-ethoxy-N-[6-(4-oxo-pentanoyl)-5,6,7,8-tetrahydro-pyrido[4,3-d]pyrimidin-2-yl]-benzamide |
| 106 | naphthalene-1-carboxylic acid [6-(propane-1-sulfonyl)-5,6,7,8-tetrahydro-pyrido[4,3-d]pyrimidin-2-yl]-amide |
| 107 | N-[6-(5-fluoro-2-methyl-benzenesulfonyl)-5,6,7,8-tetrahydro-pyrido[4,3-d]pyrimidin-2-yl]-4-methyl-benzamide |
| 109 | 3-chloro-N-[6-(2-methyl-benzoyl)-5,6,7,8-tetrahydro-pyrido[4,3-d]pyrimidin-2-yl]-benzamide |
| 110 | thiophene-2-carboxylic acid [6-(3-chloro-benzo[b]thiophene-2-carbonyl)-5,6,7,8-tetrahydro-pyrido[4,3-d]pyrimidin-2-yl]-amide |
| 112 | thiophene-2-carboxylic acid [6-(2-cyclopentyl-acetylamino)-5,6,7,8-tetrahydro-quinazolin-2-yl]-amide |
| 113 | N-[6-(3,4-dichloro-benzoyl)-5,6,7,8-tetrahydro-pyrido[4,3-d]pyrimidin-2-yl]-2-fluoro-benzamide |
| 114 | N-[6-(2-chloro-benzenesulfonyl)-5,6,7,8-tetrahydro-pyrido[4,3-d]pyrimidin-2-yl]-4-ethyl-benzamide |
| 115 | thiophene-2-carboxylic acid [6-(4-bromo-3-methyl-benzoylamino)-5,6,7,8-tetrahydro-quinazolin-2-yl]-amide |
| 116 | 3-methyl-N-[6-(toluene-3-sulfonyl)-5,6,7,8-tetrahydro-pyrido[4,3-d]pyrimidin-2-yl]-benzamide |
| 117 | naphthalene-1-carboxylic acid [6-(5-chloro-thiophene-2-sulfonyl)-5,6,7,8-tetrahydro-pyrido[4,3-d]pyrimidin-2-yl]-amide |
| 118 | N-(2-butyrylamino-5,6,7,8-tetrahydro-quinazolin-6-yl)-2,6-difluoro-benzamide |
| 119 | 3-chloro-N-[6-(3,4-dimethoxy-benzoyl)-5,6,7,8-tetrahydro-pyrido[4,3-d]pyrimidin-2-yl]-benzamide |
| 120 | N-[6-(3-chloro-benzo[b]thiophene-2-carbonyl)-5,6,7,8-tetrahydro-pyrido[4,3-d]pyrimidin-2-yl]-benzamide |
| 121 | 4-ethyl-N-[6-(thiophene-3-sulfonyl)-5,6,7,8-tetrahydro-pyrido[4,3-d]pyrimidin-2-yl]-benzamide |
| 123 | 2-ethoxy-N-[6-(2-ethylsulfanyl-pyridine-3-carbonyl)-5,6,7,8-tetrahydro-pyrido[4,3-d]pyrimidin-2-yl]-benzamide |
| 124 | 3-[2-(3-chloro-benzoylamino)-7,8-dihydro-5H-pyrido[4,3-d]pyrimidin-6-yl]-3-oxo-propionic acid ethyl ester |
| 125 | N-[6-(3-bromo-benzenesulfonyl)-5,6,7,8-tetrahydro-pyrido[4,3-d]pyrimidin-2-yl]-3-chloro-benzamide |
| 126 | 3,4-dichloro-N-{6-[2-(4-chloro-phenyl)-acetyl]-5,6,7,8-tetrahydro-pyrido[4,3-d]pyrimidin-2-yl}-benzamide |
| 127 | 3-chloro-N-[6-(2-chloro-6-fluoro-benzoyl)-5,6,7,8-tetrahydro-pyrido[4,3-d]pyrimidin-2-yl]-benzamide |
| 128 | 4-fluoro-N-(6-hexanoylamino-5,6,7,8-tetrahydro-quinazolin-2-yl)-benzamide |
| 129 | N-[6-(5-bromo-2-methoxy-benzenesulfonyl)-5,6,7,8-tetrahydro-pyrido[4,3-d]pyrimidin-2-yl]-3-methoxy-benzamide |
| 132 | N-[6-(3-cyclopentyl-propionyl)-5,6,7,8-tetrahydro-pyrido[4,3-d]pyrimidin-2-yl]-isonicotinamide |
| 133 | 5-benzyl-furan-2-carboxylic acid (2-butyrylamino-5,6,7,8-tetrahydro-quinazolin-6-yl)-amide |
| 134 | 3,4-dichloro-N-[6-(4-trifluoromethoxy-benzenesulfonyl)-5,6,7,8-tetrahydro-pyrido[4,3-d]pyrimidin-2-yl]-benzamide |
| 135 | [(2-butyrylamino-5,6,7,8-tetrahydro-quinazolin-6-ylcarbamoyl)-phenyl-methyl]-carbamic acid benzyl ester |
| 136 | N-[6-(3,4-dimethoxy-benzenesulfonyl)-5,6,7,8-tetrahydro-pyrido[4,3-d]pyrimidin-2-yl]-4-fluoro-benzamide |
| 137 | 2-fluoro-N-[6-(2-methyl-5-phenyl-furan-3-carbonyl)-5,6,7,8-tetrahydro-pyrido[4,3-d]pyrimidin-2-yl]-benzamide |
| 138 | thiophene-2-carboxylic acid (6-pent-4-enoylamino-5,6,7,8-tetrahydro-quinazolin-2-yl)-amide |
| 139 | (2-methyl-1-{2-[(thiophene-2-carbonyl)-amino]-5,6,7,8-tetrahydro-quinazolin-6-ylcarbamoyl}-propyl)-carbamic acid 9H-fluoren-9-ylmethyl ester |
| 140 | (5-{2-[(thiophene-2-carbonyl)-amino]-5,6,7,8-tetrahydro-quinazolin-6-ylcarbamoyl}-pentyl)-carbamic acid tert-butyl ester |
| 141 | 3-fluoro-N-[6-(1,2,3,4-tetrahydro-naphthalene-2-carbonyl)-5,6,7,8-tetrahydro-pyrido[4,3-d]pyrimidin-2-yl]-benzamide |
| 142 | 4-chloro-N-{6-[2-(2,5-dioxo-imidazolidin-4-yl)-acetyl]-5,6,7,8-tetrahydro-pyrido[4,3-d]pyrimidin-2-yl}-benzamide |
| 143 | 3-fluoro-N-[6-(toluene-4-sulfonyl)-5,6,7,8-tetrahydro-pyrido[4,3-d]pyrimidin-2-yl]-benzamide |
| 144 | 3,5-dichloro-N-[6-(4-thiophen-2-yl-benzoyl)-5,6,7,8-tetrahydro-pyrido[4,3-d]pyrimidin-2-yl]-benzamide |
| 145 | N-[6-(3-chloro-thiophene-2-carbonyl)-5,6,7,8-tetrahydro-pyrido[4,3-d]pyrimidin-2-yl]-2-ethoxy-benzamide |

-continued

| Example | Compound |
|---|---|
| 146 | N-[6-(toluene-3-sulfonylamino)-5,6,7,8-tetrahydro-quinazolin-2-yl]-butyramide |
| 147 | thiophene-2-carboxylic acid {6-[2-(2,2,2-trifluoro-acetyl)-1,2,3,4-tetrahydro-isoquinoline-7-sulfonylamino]-5,6,7,8-tetrahydro-quinazolin-2-yl}-amide |
| 148 | 4-methyl-N-[6-(4-trifluoromethylsulfanyl-benzoyl)-5,6,7,8-tetrahydro-pyrido[4,3-d]pyrimidin-2-yl]-benzamide |
| 149 | (2-{2-[(thiophene-2-carbonyl)-amino]-5,6,7,8-tetrahydro-quinazolin-6-ylcarbamoyl}-ethyl)-carbamic acid tert-butyl ester |
| 150 | 2-fluoro-N-[6-(2-methyl-5-nitro-benzenesulfonyl)-5,6,7,8-tetrahydro-pyrido[4,3-d]pyrimidin-2-yl]-benzamide |
| 151 | N-[6-(4-methoxy-benzenesulfonylamino)-5,6,7,8-tetrahydro-quinazolin-2-yl]-butyramide |
| 152 | 4-chloro-N-[6-(2,4-difluoro-benzoyl)-5,6,7,8-tetrahydro-pyrido[4,3-d]pyrimidin-2-yl]-benzamide |
| 153 | 4-methyl-N-(6-pent-4-enoyl-5,6,7,8-tetrahydro-pyrido[4,3-d]pyrimidin-2-yl)-benzamide |
| 154 | naphthalene-1-carboxylic acid [6-(3-fluoro-4-methyl-benzoyl)-5,6,7,8-tetrahydro-pyrido[4,3-d]pyrimidin-2-yl]-amide |
| 155 | N-{6-[2-(4-trifluoromethyl-phenyl)-acetyl]-5,6,7,8-tetrahydro-pyrido[4,3-d]pyrimidin-2-yl}-benzamide |
| 156 | N-[6-(3,4-dichloro-benzoyl)-5,6,7,8-tetrahydro-pyrido[4,3-d]pyrimidin-2-yl]-nicotinamide |
| 157 | 4-ethyl-N-{6-[2-(2,2,2-trifluoro-acetyl)-1,2,3,4-tetrahydro-isoquinoline-7-sulfonyl]-5,6,7,8-tetrahydro-pyrido[4,3-d]pyrimidin-2-yl}-benzamide |
| 158 | 2-methoxy-N-[6-(4-methoxy-2,3,6-trimethyl-benzenesulfonyl)-5,6,7,8-tetrahydro-pyrido[4,3-d]pyrimidin-2-yl]-benzamide |
| 159 | 4-ethyl-N-[6-(2-methoxy-acetyl)-5,6,7,8-tetrahydro-pyrido[4,3-d]pyrimidin-2-yl]-benzamide |
| 160 | 4-fluoro-N-[6-(propane-1-sulfonylamino)-5,6,7,8-tetrahydro-quinazolin-2-yl]-benzamide |
| 162 | N-[6-(7,7-dimethyl-2-oxo-bicyclo[2.2.1]hept-1-ylmethanesulfonylamino)-5,6,7,8-tetrahydro-quinazolin-2-yl]-butyramide |
| 163 | N-{6-[2-(2,5-dimethyl-phenyl)-acetylamino]-5,6,7,8-tetrahydro-quinazolin-2-yl}-4-fluoro-benzamide |
| 165 | thiophene-2-carboxylic acid (6-phenylmethanesulfonylamino-5,6,7,8-tetrahydro-quinazolin-2-yl)-amide |
| 166 | N-[6-(3,4-dimethoxy-benzenesulfonylamino)-5,6,7,8-tetrahydro-quinazolin-2-yl]-butyramide |
| 167 | N-{6-[4-(1,1-dimethyl-propyl)-benzenesulfonylamino]-5,6,7,8-tetrahydro-quinazolin-2-yl}-butyramide |
| 168 | N-(2-butyrylamino-5,6,7,8-tetrahydro-quinazolin-6-yl)-3-(3-trifluoromethyl-phenyl)-acrylamide |
| 169 | N-[6-(butane-1-sulfonylamino)-5,6,7,8-tetrahydro-quinazolin-2-yl]-4-fluoro-benzamide |
| 170 | naphthalene-1-carboxylic acid (6-acetyl-5,6,7,8-tetrahydro-pyrido[4,3-d]pyrimidin-2-yl)-amide |
| 171 | 3,5-dichloro-N-[6-(3-diethylcarbamoyl-propionyl)-5,6,7,8-tetrahydro-pyrido[4,3-d]pyrimidin-2-yl]-benzamide |
| 172 | 4-ethyl-N-[6-(4-methoxy-benzenesulfonyl)-5,6,7,8-tetrahydro-pyrido[4,3-d]pyrimidin-2-yl]-benzamide |
| 173 | 4-ethyl-N-[6-(quinoline-6-carbonyl)-5,6,7,8-tetrahydro-pyrido[4,3-d]pyrimidin-2-yl]-benzamide |
| 174 | N-[6-(2-cyclopropyl-acetyl)-5,6,7,8-tetrahydro-pyrido[4,3-d]pyrimidin-2-yl]-2-fluoro-benzamide |
| 175 | N-[6-(2H-chromene-3-carbonyl)-5,6,7,8-tetrahydro-pyrido[4,3-d]pyrimidin-2-yl]-3,4-difluoro-benzamide |
| 176 | N-{6-[2-(4-chloro-phenyl)-propionyl]-5,6,7,8-tetrahydro-pyrido[4,3-d]pyrimidin-2-yl}-benzamide |
| 177 | thiophene-2-carboxylic acid [6-(2-naphthalen-1-yl-acetylamino)-5,6,7,8-tetrahydro-quinazolin-2-yl]-amide |
| 178 | 4-fluoro-N-(6-phenylmethanesulfonyl-5,6,7,8-tetrahydro-pyrido[4,3-d]pyrimidin-2-yl)-benzamide |
| 180 | thiophene-2-carboxylic acid [6-(2,5-dichloro-thiophene-3-sulfonylamino)-5,6,7,8-tetrahydro-quinazolin-2-yl]-amide |
| 181 | {5-[2-(4-fluoro-benzoylamino)-5,6,7,8-tetrahydro-quinazolin-6-ylcarbamoyl]-pentyl}-carbamic acid benzyl ester |
| 182 | N-[6-(2,5-dimethyl-2H-pyrazole-3-carbonyl)-5,6,7,8-tetrahydro-pyrido[4,3-d]pyrimidin-2-yl]-4-ethyl-benzamide |
| 183 | naphthalene-1-carboxylic acid [6-(3-fluoro-benzoyl)-5,6,7,8-tetrahydro-pyrido[4,3-d]pyrimidin-2-yl]-amide |
| 184 | N-[6-(benzo[b]thiophene-3-carbonyl)-5,6,7,8-tetrahydro-pyrido[4,3-d]pyrimidin-2-yl]-4-tert-butyl-benzamide |
| 185 | 4-fluoro-N-[6-(4-methoxy-benzenesulfonyl)-5,6,7,8-tetrahydro-pyrido[4,3-d]pyrimidin-2-yl]-benzamide |
| 186 | 4-tert-butyl-N-[6-(2,3-dihydro-benzo[1,4]dioxin-6-sulfonyl)-5,6,7,8-tetrahydro-pyrido[4,3-d]pyrimidin-2-yl]-benzamide |

-continued

| Example | Compound |
|---|---|
| 187 | 3-chloro-N-{6-[2-(2,6-dichloro-phenyl)-acetyl]-5,6,7,8-tetrahydro-pyrido[4,3-d]pyrimidin-2-yl}-benzamide |
| 188 | thiophene-2-carboxylic acid [6-(2,3-dihydro-benzo[1,4]dioxin-6-sulfonylamino)-5,6,7,8-tetrahydro-quinazolin-2-yl]-amide |
| 189 | N-{6-[2-(3-chloro-phenoxy)-acetyl]-5,6,7,8-tetrahydro-pyrido[4,3-d]pyrimidin-2-yl}-4-methyl-benzamide |
| 190 | N-[6-(5-phenyl-pentanoyl)-5,6,7,8-tetrahydro-pyrido[4,3-d]pyrimidin-2-yl]-benzamide |
| 191 | 4-ethyl-N-[6-(2-ethyl-butyryl)-5,6,7,8-tetrahydro-pyrido[4,3-d]pyrimidin-2-yl]-benzamide |
| 192 | 3,5-dichloro-N-[6-(4-trifluoromethoxy-benzoyl)-5,6,7,8-tetrahydro-pyrido[4,3-d]pyrimidin-2-yl]-benzamide |
| 193 | naphthalene-1-carboxylic acid [6-(4-methyl-octanoyl)-5,6,7,8-tetrahydro-pyrido[4,3-d]pyrimidin-2-yl]-amide |
| 194 | 4-[2-(4-fluoro-benzoylamino)-5,6,7,8-tetrahydro-quinazolin-6-ylcarbamoyl]-piperidine-1-carboxylic acid tert-butyl ester |
| 195 | N-[6-(2-benzyloxy-acetyl)-5,6,7,8-tetrahydro-pyrido[4,3-d]pyrimidin-2-yl]-2-methoxy-benzamide |
| 196 | N-[6-(2-trifluoromethyl-benzenesulfonylamino)-5,6,7,8-tetrahydro-quinazolin-2-yl]-butyramide |
| 197 | N-[2-(4-fluoro-benzoylamino)-5,6,7,8-tetrahydro-quinazolin-6-yl]-2-methyl-6-trifluoromethyl-nicotinamide |
| 198 | N-[6-(3-cyano-benzoyl)-5,6,7,8-tetrahydro-pyrido[4,3-d]pyrimidin-2-yl]-2-trifluoromethyl-benzamide |
| 199 | 3-methoxy-N-[6-(3-trifluoromethoxy-benzoyl)-5,6,7,8-tetrahydro-pyrido[4,3-d]pyrimidin-2-yl]-benzamide |
| 200 | N-(6-butyryl-5,6,7,8-tetrahydro-pyrido[4,3-d]pyrimidin-2-yl)-2-fluoro-benzamide |
| 201 | N-(6-benzenesulfonylamino-5,6,7,8-tetrahydro-quinazolin-2-yl)-4-fluoro-benzamide |
| 202 | N-[6-(5-chloro-thiophene-2-sulfonylamino)-5,6,7,8-tetrahydro-quinazolin-2-yl]-4-fluoro-benzamide |
| 203 | naphthalene-1-carboxylic acid (6-hexanoyl-5,6,7,8-tetrahydro-pyrido[4,3-d]pyrimidin-2-yl)-amide |
| 204 | N-(6-propionyl-5,6,7,8-tetrahydro-pyrido[4,3-d]pyrimidin-2-yl)-2-trifluoromethyl-benzamide |
| 205 | N-[6-(2-ethyl-butyryl)-5,6,7,8-tetrahydro-pyrido[4,3-d]pyrimidin-2-yl]-4-methyl-benzamide |
| 206 | 2-fluoro-N-[6-(3-trifluoromethyl-benzenesulfonyl)-5,6,7,8-tetrahydro-pyrido[4,3-d]pyrimidin-2-yl]-benzamide |
| 207 | 5-benzyl-furan-2-carboxylic acid {2-[(thiophene-2-carbonyl)-amino]-5,6,7,8-tetrahydro-quinazolin-6-yl}-amide |
| 208 | thiophene-2-carboxylic acid {6-[2-(2,5-dimethyl-phenyl)-acetylamino]-5,6,7,8-tetrahydro-quinazolin-2-yl}-amide |
| 210 | 4-fluoro-N-[6-(propane-1-sulfonyl)-5,6,7,8-tetrahydro-pyrido[4,3-d]pyrimidin-2-yl]-benzamide |
| 211 | 2-[2-(3-fluoro-benzoylamino)-7,8-dihydro-5H-pyrido[4,3-d]pyrimidine-6-sulfonyl]-benzoic acid methyl ester |
| 212 | 3,5-dichloro-N-[6-(5-[1,2]dithiolan-3-yl-pentanoyl)-5,6,7,8-tetrahydro-pyrido[4,3-d]pyrimidin-2-yl]-benzamide |
| 213 | thiophene-2-carboxylic acid [6-(2-phenoxy-butyrylamino)-5,6,7,8-tetrahydro-quinazolin-2-yl]-amide |
| 214 | thiophene-2-carboxylic acid {6-[2-(4-methoxyphenyl)-acetylamino]-5,6,7,8-tetrahydro-quinazolin-2-yl}-amide |
| 215 | N-(6-cyclohexanecarboxylic-5,6,7,8-tetrahydro-pyrido[4,3-d]pyrimidin-2-yl)-2-trifluoromethyl-benzamide |
| 216 | N-[6-(2,4-dimethyl-thiazole-5-sulfonyl)-5,6,7,8-tetrahydro-pyrido[4,3-d]pyrimidin-2-yl]-2-trifluoromethyl-benzamide |
| 217 | 2-thiophen-2-yl-thiazole-4-carboxylic acid {2-[(thiophene-2-carbonyl)-amino]-5,6,7,8-tetrahydro-quinazolin-6-yl}-amide |
| 219 | thiophene-2-carboxylic acid {6-[3-(3-trifluoromethyl-phenyl)-acryloylamino]-5,6,7,8-tetrahydro-quinazolin-2-yl}-amide |
| 220 | thiophene-2-carboxylic acid [6-(5-phenyl-pentanoylamino)-5,6,7,8-tetrahydro-quinazolin-2-yl]-amide |
| 221 | thiophene-2-carboxylic acid [6-(2-chloro-5-trifluoromethyl-benzoylamino)-5,6,7,8-tetrahydro-quinazolin-2-yl]-amide |
| 222 | 4-fluoro-N-[6-(2,3,5,6-tetramethyl-benzenesulfonylamino)-5,6,7,8-tetrahydro-quinazolin-2-yl]-benzamide |
| 223 | 4-fluoro-N-[6-(4-methyl-octanoyl)-5,6,7,8-tetrahydro-pyrido[4,3-d]pyrimidin-2-yl]-benzamide |
| 224 | 2-{2-[(thiophene-2-carbonyl)-amino]-5,6,7,8-tetrahydro-quinazolin-6-ylsulfamoyl}-benzoic acid methyl ester |
| 225 | [(3-methyl-1-{2-[(thiophene-2-carbonyl)-amino]-5,6,7,8-tetrahydro-quinazolin-6-ylcarbamoyl}-butylcarbamoyl)-methyl]-carbamic acid benzyl ester |
| 226 | 3-chloro-N-(6-pentanoyl-5,6,7,8-tetrahydro-pyrido[4,3-d]pyrimidin-2-yl)-benzamide |

-continued

| Example | Compound |
|---|---|
| 227 | 4-fluoro-N-[6-(5-oxo-5-phenyl-pentanoylamino)-5,6,7,8-tetrahydro-quinazolin-2-yl]-benzamide |
| 228 | thiophene-2-carboxylic acid [6-(3-phenyl-acryloylamino)-5,6,7,8-tetrahydro-quinazolin-2-yl]-amide |
| 229 | N-[6-(5-[1,2]dithiolan-3-yl-pentanoylamino)-5,6,7,8-tetrahydro-quinazolin-2-yl]-4-fluoro-benzamide |
| 230 | benzoic acid 2-(2-{2-[(thiophene-2-carbonyl)-amino]-5,6,7,8-tetrahydro-quinazolin-6-ylcarbamoyl}-ethyl)-phenyl ester |
| 231 | 4-fluoro-N-[6-(2-methyl-5-nitro-benzenesulfonylamino)-5,6,7,8-tetrahydro-quinazolin-2-yl]-benzamide |
| 232 | 4-chloro-N-[6-(2-phenoxy-acetyl)-5,6,7,8-tetrahydro-pyrido[4,3-d]pyrimidin-2-yl]-benzamide |
| 234 | N-[6-(5-bromo-thiophene-2-carbonyl)-5,6,7,8-tetrahydro-pyrido[4,3-d]pyrimidin-2-yl]-2-fluoro-benzamide |
| 235 | 4-fluoro-N-[6-(5-fluoro-2-methyl-benzenesulfonylamino)-5,6,7,8-tetrahydro-quinazolin-2-yl]-benzamide |
| 236 | N-[6-(4-acetylamino-benzenesulfonylamino)-5,6,7,8-tetrahydro-quinazolin-2-yl]-4-fluoro-benzamide |
| 237 | thiophene-2-carboxylic acid [6-(2-trifluoromethyl-benzoylamino)-5,6,7,8-tetrahydro-quinazolin-2-yl]-amide |
| 238 | 3,4-difluoro-N-[6-(quinoline-6-carbonyl)-5,6,7,8-tetrahydro-pyrido[4,3-d]pyrimidin-2-yl]-benzamide |
| 239 | {1-[2-(4-fluoro-benzoylamino)-5,6,7,8-tetrahydro-quinazolin-6-ylcarbamoyl]-2-phenyl-ethyl}-carbamic acid tert-butyl ester |
| 240 | thiophene-2-carboxylic acid [6-(2-methyl-benzoylamino)-5,6,7,8-tetrahydro-quinazolin-2-yl]-amide |
| 241 | 3-chloro-N-{6-[3-(2-oxo-benzooxazol-3-yl)-propionyl]-5,6,7,8-tetrahydro-pyrido[4,3-d]pyrimidin-2-yl}-benzamide |
| 242 | 3-chloro-N-[6-(5-chloro-thiophene-2-sulfonyl)-5,6,7,8-tetrahydro-pyrido[4,3-d]pyrimidin-2-yl]-benzamide |
| 243 | 3,5-dichloro-N-[6-(4-methoxy-benzenesulfonyl)-5,6,7,8-tetrahydro-pyrido[4,3-d]pyrimidin-2-yl]-benzamide |
| 244 | 4-tert-butyl-N-[6-(5-methyl-isoxazole-3-carbonyl)-5,6,7,8-tetrahydro-pyrido[4,3-d]pyrimidin-2-yl]-benzamide |
| 245 | N-[6-(5-bromo-2-methoxy-benzenesulfonyl)-5,6,7,8-tetrahydro-pyrido[4,3-d]pyrimidin-2-yl]-4-methyl-benzamide |
| 246 | 4-tert-butyl-N-{6-[3-(2-hydroxyphenyl)-propionyl]-5,6,7,8-tetrahydro-pyrido[4,3-d]pyrimidin-2-yl}-benzamide |
| 247 | 4-fluoro-N-[6-(2-phenyl-butyrylamino)-5,6,7,8-tetrahydro-quinazolin-2-yl]-benzamide |
| 248 | 4-tert-butyl-N-[6-(4-propyl-benzoyl)-5,6,7,8-tetrahydro-pyrido[4,3-d]pyrimidin-2-yl]-benzamide |
| 249 | thiophene-2-carboxylic acid [6-(2-bromo-benzoylamino)-5,6,7,8-tetrahydro-quinazolin-2-yl]-amide |
| 250 | 2-methoxy-N-[6-(6-phenoxy-pyridine-3-carbonyl)-5,6,7,8-tetrahydro-pyrido[4,3-d]pyrimidin-2-yl]-benzamide |
| 251 | N-[6-(4-acetylamino-benzenesulfonyl)-5,6,7,8-tetrahydro-pyrido[4,3-d]pyrimidin-2-yl]-4-ethyl-benzamide |
| 252 | 3,5-dichloro-N-[6-(4-fluoro-benzenesulfonyl)-5,6,7,8-tetrahydro-pyrido[4,3-d]pyrimidin-2-yl]-benzamide |
| 253 | N-[6-(1-benzenesulfonyl-1H-indole-2-carbonyl)-5,6,7,8-tetrahydro-pyrido[4,3-d]pyrimidin-2-yl]-4-fluoro-benzamide |
| 255 | N-[6-(3-chloro-benzenesulfonylamino)-5,6,7,8-tetrahydro-quinazolin-2-yl]-4-fluoro-benzamide |

Pharmacological Data:

The affinity of the substituted 5,6,7,8-tetrahydro-pyrido[4,3-d]pyrimidin-2-yl or 5,6,7,8-tetrahydro-quinazolin-2-yl compound according to the invention for the batrachotoxin (BTX) binding site and for the mGluR5-receptor and the inhibition of noradrenalin or 5-HT reuptake was determined as described above.

The substituted 5,6,7,8-tetrahydro-pyrido[4,3-d]pyrimidin-2-yl or 5,6,7,8-tetrahydro-quinazolin-2-yl compounds according to the invention exhibit good to very good inhibition of noradrenalin reuptake and good to very good inhibition of 5-hydroxy-tryptophan reuptake.

Furthermore, these compounds according to the invention also exhibit excellent affinity for the batrachotoxin (BTX) binding site of the sodium channel and the mGluR5 receptor.

Table I below gives the respective pharmacological data for some exemplary substituted 5,6,7,8-tetrahydro-pyrido[4,3-d]pyrimidin-2-yl or 5,6,7,8-tetrahydro-quinazolin-2-yl compounds.

TABLE I

| Compound according to Example | mGluR5 (MPEP), 10 µM, % inhibition | BTX inhibition | 5-HT uptake, rat, 1 µM, % inhibition | NA uptake, rat, 10 µM, % inhibition |
|---|---|---|---|---|
| 29 | 40.51 | | | |
| 68 | | 35 | | |
| 69 | | 64 | 70 | 73 |
| 71 | | 69 | 47 | 74 |
| 72 | | 31 | | 41 |
| 74 | | 66 | 54 | 43 |

TABLE I-continued

| Compound according to Example | mGluR5 (MPEP), 10 µM, % inhibition | BTX inhibition | 5-HT uptake, rat, 1 µM, % inhibition | NA uptake, rat, 10 µM, % inhibition |
|---|---|---|---|---|
| 78 | 41.06 | 31 | | |
| 79 | | 34 | | |
| 80 | | | | 54 |
| 82 | 36.33 | 38 | | 32 |
| 83 | | | 39 | 77 |
| 86 | | 62 | | 32 |
| 92 | | 75 | 66 | 35 |
| 94 | | 47 | | |
| 95 | | 77 | 59 | 72 |
| 97 | | | 30 | |
| 99 | | 78 | 41 | 56 |
| 101 | | 68 | 65 | 84 |
| 102 | | | 63 | |
| 103 | | | 65 | |
| 107 | 38.23 | 73 | 36 | 39 |
| 109 | | | 30 | 92 |
| 110 | | 40 | 96 | 75 |
| 113 | 31.26 | 38 | 45 | 67 |
| 114 | | 82 | 50 | 73 |
| 115 | 34.26 | 82 | 56 | 49 |
| 116 | | 53 | 31 | 52 |
| 117 | | 37 | 32 | 31 |
| 119 | | | 34 | 72 |
| 120 | | 48 | 92 | 78 |
| 121 | | 57 | 52 | 92 |
| 124 | | | | 65 |
| 125 | | 66 | 43 | 70 |
| 126 | | 70 | 55 | 89 |
| 127 | | 30 | 35 | 71 |
| 128 | | 33 | | |
| 129 | 51.14 | 76 | | |
| 132 | 58.08 | 72 | | |
| 133 | | 39 | | |
| 134 | | 64 | 58 | 59 |
| 137 | | 43 | | |
| 139 | 31.02 | 62 | | |
| 141 | | 63 | 54 | 55 |
| 143 | 37.25 | 61 | | 53 |
| 144 | | 81 | 42 | 67 |
| 145 | 84.43 | 46 | | |
| 146 | 39.64 | | | |
| 147 | | 48 | | |
| 148 | | 85 | 32 | |
| 149 | | | 32 | |
| 150 | | 49 | 54 | |
| 152 | 34.01 | 55 | 33 | |
| 154 | 30.72 | | | 50 |
| 155 | | 62 | | |
| 156 | 45.96 | | | 50 |
| 157 | | 63 | 43 | 61 |
| 158 | | 74 | 55 | 36 |
| 160 | | | 40 | |
| 162 | | | 29 | |
| 163 | | 28 | | |
| 165 | | | 35 | |
| 167 | | 51 | 32 | |
| 168 | 33.45 | 39 | 46 | |
| 171 | | | 32 | |
| 172 | 70.12 | 57 | 57 | 85 |
| 173 | | 69 | | |
| 175 | | 49 | 32 | 46 |
| 176 | | | | 38 |
| 177 | 41.98 | | 39 | |
| 178 | 45.31 | | | |
| 180 | 86.74 | 46 | | 34 |
| 181 | 36.39 | | | |
| 183 | | 31 | | 63 |
| 184 | | 87 | 48 | 69 |
| 185 | | | | 36 |
| 186 | | 77 | 46 | 82 |
| 187 | | 43 | 29 | 100 |
| 189 | 39.49 | 55 | 46 | 53 |
| 190 | | 56 | 36 | 73 |
| 192 | | 87 | 47 | 73 |
| 193 | 51.83 | 84 | 38 | 43 |
| 194 | 45.64 | | | |
| 195 | | | 35 | 31 |
| 197 | 32.15 | | | |
| 199 | | 48 | | 52 |
| 202 | 33.07 | | | |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A 5,6,7,8-tetrahydro-pyrido[4,3-d]pyrimidin-2-yl compound corresponding to formula I,

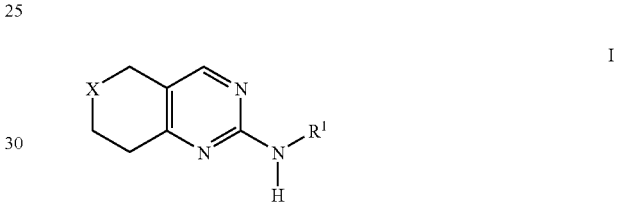

wherein x represents an $NR^{2a}$ group;

$R^1$ represents a —C(=O)—$R^3$ group or a —C(=O)—O—$R^4$ group;

$R^{2a}$ represents a —C(=O)—$R^5$ group or an —S(=O)$_2$—$R^6$ group;

$R^3$ represents a linear or branched, unsubstituted or at least monosubstituted, saturated or unsaturated aliphatic group, which may comprise at least one heteroatom as a chain link; an unsubstituted or at least monosubstituted, saturated or unsaturated cycloaliphatic group, which may comprise at least one heteroatom as a ring member, which group may be attached via a linear or branched, unsubstituted or at least monosubstituted alkylene group, which may comprise at least one heteroatom as a chain link; or an unsubstituted or at least monosubstituted aryl or heteroaryl group, which may be attached via a linear or branched, unsubstituted or at least monosubstituted alkylene group;

$R^4$ represents an unsubstituted or at least monosubstituted aryl or heteroaryl group, which may be attached via a linear or branched, unsubstituted or at least monosubstituted alkylene group;

$R^5$ represents a linear or branched, unsubstituted or at least monosubstituted, saturated or unsaturated aliphatic group, which may comprise at least one heteroatom as a chain link;

an unsubstituted or at least monosubstituted, saturated or unsaturated cycloaliphatic group, which may comprise at least one heteroatom as a ring member, which group may be attached via a linear or branched, unsubstituted or at least monosubstituted alkylene group, which may comprise at least one heteroatom as a chain link or may be fused with an unsubstituted or at least monosubstituted, mono- or polycyclic ring system;

an unsubstituted or at least monosubstituted aryl or heteroaryl group, which may be attached via a linear or branched, unsubstituted or at least monosubstituted alkylene, alkenylene or alkynylene group, which may comprise at least one heteroatom as a chain link or may be fused with an unsubstituted or at least monosubstituted, mono- or polycyclic ring system;

a —C(=O)—$R^7$ group, which may be attached via a linear or branched, unsubstituted or at least monosubstituted alkylene group;

a —C(=O)—$R^8$ group, which may be attached via a linear or branched, unsubstituted or at least monosubstituted alkylene group, or an —N(H)—C(=O)—O—$R^9$ group, which may be attached via a linear or branched, unsubstituted or at least monosubstituted alkylene group, which may comprise at least one —N(H)—C(=O) or at least one —C(=O)—N(H) grouping as a chain link;

$R^6$ represents an —$NR^{10}R^{11}$ group;

a linear or branched, unsubstituted or at least monosubstituted, saturated or unsaturated aliphatic group, which may comprise at least one heteroatom as a chain link;

an unsubstituted or at least monosubstituted, saturated or unsaturated cycloaliphatic group, which may comprise at least one heteroatom as a ring member, and which may be fused with an unsubstituted or at least monosubstituted mono- or polycyclic ring system, which group may be attached via a linear or branched, unsubstituted or at least monosubstituted alkylene group, which may comprise at least one heteroatom as a chain link or may be bridged with a linear or branched alkylene group; or an unsubstituted or at least monosubstituted aryl or heteroaryl group, which may be attached via a linear or branched, unsubstituted or at least monosubstituted alkylene group or may be fused with an unsubstituted or at least monosubstituted mono- or polycyclic ring system;

$R^7$ represents a linear or branched, unsubstituted or at least monosubstituted alkyl group, an unsubstituted or at least monosubstituted aryl or heteroaryl group, an unsubstituted or at least monosubstituted, saturated or unsaturated cycloaliphatic group, which may comprise at least one heteroatom as a ring member, which group may be fused with an unsubstituted or at least monosubstituted mono- or polycyclic ring system, or an —$NR^{7a}R^{7b}$ group, wherein $R^{7a}$ and $R^{7b}$, identically or differently, in each case, represent a linear or branched alkyl group, $R^8$ represents a linear or branched, unsubstituted or at least monosubstituted alkyl group or an unsubstituted or at least monosubstituted aryl or heteroaryl group, which may be attached by a linear or branched alkylene group, $R^9$ represents a linear or branched, unsubstituted or at least monosubstituted alkyl group, an unsubstituted or at least monosubstituted aryl or heteroaryl group, which may be attached via a linear or branched alkylene group, or an unsubstituted or at least monosubstituted, saturated or unsaturated cycloaliphatic group, which may be fused with at least one unsubstituted or at least monosubstituted mono- or polycyclic ring system, $R^{10}$ and $R^{11}$, identically or differently, in each case, represent a linear or branched alkyl group, or a salt thereof wherein said heteroatom as a chain link is an oxygen or sulfur atom or an NH group.

2. The compound of claim 1, wherein said compound is present in the form of an isolated enantiomer or isolated diastereoisomer.

3. The compound of claim 1, wherein said compound is present in the form of a mixture of stereoisomers.

4. The compound of claim 1, wherein said compound is present in the form of a racemic mixture.

5. A compound according to claim 1, wherein $R^3$ represents a linear or branched, unsubstituted or at least monosubstituted, saturated or unsaturated aliphatic $C_{1-8}$ group, which may comprise at least one heteroatom as a chain link; an unsubstituted or at least monosubstituted, saturated or unsaturated 3- to 8-membered cycloaliphatic group, which may comprise at least one heteroatom as a ring member, which group may be attached via a linear or branched, unsubstituted or at least monosubstituted $C_{1-3}$ alkylene group, which may comprise at least one heteroatom as a chain link, or an unsubstituted or at least monosubstituted 5- to 14-membered aryl or heteroaryl group, which may be attached via a linear or branched, unsubstituted or at least monosubstituted $C_{1-3}$ alkylene group;

$R^4$ represents an unsubstituted or at least monosubstituted 5- to 14-membered aryl or heteroaryl group, which may be attached via a linear or branched, unsubstituted or at least monosubstituted $C_{1-3}$ alkylene group;

$R^5$ represents a linear or branched, unsubstituted or at least monosubstituted, saturated or unsaturated aliphatic $C_{1-10}$ group, which may comprise at least one heteroatom as a chain link;

an unsubstituted or at least monosubstituted, saturated or unsaturated 3- to 8-membered cycloaliphatic group, which may comprise at least one heteroatom as a ring member, which group may be attached via a linear or branched, unsubstituted or at least monosubstituted $C_{1-6}$ alkylene group, which may comprise at least one heteroatom as a chain link or may be fused with an unsubstituted or at least monosubstituted mono- or polycyclic ring system;

an unsubstituted or at least monosubstituted 5- to 14-membered aryl or heteroaryl group, which may be attached via a linear or branched, unsubstituted or at least monosubstituted $C_{1-6}$ alkylene, $C_{2-6}$ alkenylene or $C_{2-6}$ alkynylene group, which may comprise at least one heteroatom as a chain link or may be fused with an unsubstituted or at least monosubstituted mono- or polycyclic ring system;

a —C(=O)—$R^7$ group, which may be attached via a linear or branched, unsubstituted or at least monosubstituted $C_{1-3}$ alkylene group;

a —C(=O)—$R^8$ group, which may be attached via a linear or branched, unsubstituted or at least monosubstituted $C_{1-3}$ alkylene group; or an —N(H)—C(=O)—O—$R^9$ group, which may be attached via a linear or branched, unsubstituted or at least monosubstituted $C_{1-8}$ alkylene group, which may comprise at least one —N(H)—C(=O) or at least one —C(=O)—N(H) group as a chain link;

$R^6$ represents —$NR^{10}R^{11}$;

a linear or branched, unsubstituted or at least monosubstituted, saturated or unsaturated aliphatic $C_{1-10}$ group, which may comprise at least one heteroatom as a chain link;

an unsubstituted or at least monosubstituted, saturated or unsaturated cycloaliphatic group, which may comprise at least one heteroatom as a ring member, and may be fused with an unsubstituted or at least monosubstituted mono- or polycyclic ring system, which group may be attached via a linear or branched, unsubstituted or at least monosubstituted $C_{1-6}$ alkylene group, which may comprise at least one heteroatom as a chain link or may be bridged with a linear or branched $C_{1-6}$ alkylene group; or an unsubstituted or at least monosubstituted 5- to 14-membered aryl or heteroaryl group, which may be attached via a linear or branched, unsubstituted or at least monosubstituted $C_{1-6}$ alkylene group or may be fused with an unsubstituted or at least monosubstituted mono- or polycyclic ring system;

$R^7$ represents a linear or branched, unsubstituted or at least monosubstituted $C_{1-3}$ alkyl group, an unsubstituted or at least monosubstituted 5- to 14-membered aryl or heteroaryl group, an unsubstituted or at least monosubstituted, saturated or unsaturated 5-, 6- or 7-membered cycloaliphatic group, which may comprise at least one heteroatom as a ring member, which group may be fused with an unsubstituted or at least monosubstituted mono- or polycyclic ring system, or an —$NR^{7a}R^{7b}$ group, in which $R^{7a}$ and $R^{7b}$, identically or differently, in each case, represent a linear or branched $C_{1-5}$ alkyl group;

$R^8$ represents a linear or branched, unsubstituted or at least monosubstituted $C_{1-3}$ alkyl group or an unsubstituted or at least monosubstituted 5- or 6-membered aryl or heteroaryl group, which may be attached via a linear or branched $C_{1-3}$ alkylene group;

$R^9$ represents a linear or branched, unsubstituted or at least monosubstituted $C_{1-3}$ alkyl group; an unsubstituted or at least monosubstituted 5- or 6-membered aryl or heteroaryl group, which may be attached via a linear or branched $C_{1-3}$ alkylene group; or an unsubstituted or at least monosubstituted, saturated or unsaturated 5- or 6-membered cycloaliphatic group, which may be fused with at least one unsubstituted or at least monosubstituted mono- or polycyclic ring system, and, $R^{10}$ and $R^{11}$, identically or differently, in each case, represent a linear or branched $C_{1-5}$ alkyl group.

6. A compound according to claim 1, wherein $R^3$ represents a linear or branched, unsubstituted or at least monosubstituted $C_{1-8}$ alkyl group, which may comprise one or more oxygen atoms or one or more NH groups as chain links; an unsubstituted or at least monosubstituted, saturated or unsaturated 5-, 6- or 7-membered cycloaliphatic group which may comprise at least one heteroatom as a ring member, which group may be attached via a linear or branched, unsubstituted or at least monosubstituted $C_{1-3}$ alkylene group which may comprise at least one heteroatom as a chain link, or an unsubstituted or at least monosubstituted phenyl group, thiophenyl group (thienyl group), furanyl group (furyl group), pyridinyl group or naphthyl group, which may be attached via a linear or branched, unsubstituted or at least monosubstituted $C_{1-3}$ alkylene group.

7. A compound according to claim 1, wherein $R^3$ represents a methyl, ethyl, n-propyl, iso-propyl, n-butyl, iso-butyl, sec-butyl or tert-butyl group; an unsubstituted, saturated or unsaturated 5-, 6- or 7-membered cycloaliphatic group which may comprise one or more oxygen atoms or one or more nitrogen atoms as ring members, which group may be attached via a —$(CH_2)$—, —$(CH_2)_2$— or —$(CH_2)_3$— group, or a phenyl group, thiophenyl group, furanyl group, pyridinyl group or naphthyl group, which may be attached via a —$(CH_2)$, —$(CH_2)_2$ or —$(CH_2)_3$ group or be mono- or polysubstituted, identically or differently, with a substituent selected from the group consisting of methyl, ethyl, n-propyl, iso-propyl, n-butyl, iso-butyl, sec-butyl, tert-butyl, methoxy, ethoxy, n-propoxy, iso-propoxy, n-butoxy, iso-butoxy, sec-butoxy, tert-butoxy, F, Cl, Br, I, —CN and —$CF_3$.

8. A compound according to claim 1, wherein $R^4$ represents a phenyl group which may be attached via a —$(CH_2)$, —$(CH_2)_2$ or —$(CH_2)_3$ bridge, wherein the phenyl group, which may be unsubstituted or at least monosubstituted, identical or different, may be substituted with a substituent selected from the group consisting of methyl, ethyl, n-propyl, iso-propyl, n-butyl, iso-butyl, sec-butyl, tert-butyl, methoxy, ethoxy, n-propoxy, iso-propoxy, n-butoxy, iso-butoxy, sec-butoxy, tert-butoxy, F, Cl, Br, I, —CN and —$CF_3$.

9. A compound according to claim 1, wherein $R^4$ represents an unsubstituted benzyl group.

10. A compound according to claim 1, wherein $R^5$ represents a linear or branched $C_{1-10}$ alkyl group, which may comprise one or more oxygen atoms or one or more sulfur atoms or one or more —N(H) groups as chain links;

a linear or branched $C_{2-10}$ alkenyl group, which may comprise one or more oxygen atoms or one or more sulfur atoms or one or more —N(H) groups as chain links; a linear or branched 2-10 alkynyl group, which may comprise one or more oxygen atoms or one or more sulfur atoms or one or more —N(H) groups as chain links;

an unsubstituted or at least monosubstituted, saturated or unsaturated 3- to 8-membered cycloaliphatic group, which may comprise one or more heteroatoms, identically or differently, in each case, selected from the group consisting of oxygen, sulfur and nitrogen, as ring members, which group may be attached via a —$(CH_2)$, —$(CH_2)_2$, —$(CH_2)_3$, —$(CH_2)_4$, —$C(C_2H_5)(H)$, —$(CH_2)$—O, —$(CH_2)_2$—O, —$(CH_2)_3$—O, —$(CH_2)_4$—O, —O—$(CH_2)$, —O—$(CH_2)_2$, —O—$(CH_2)_3$, —O—$(CH_2)_4$, —$C(C_2H_5)(H)$—O—, —O—$C(C_2H_5)(H)$, —$CH_2$—O—$CH_2$, —$CH_2$—S—$CH_2$, —$C(CH_3)_2$ or —$C(H)(CH_3)$ group or may be fused with an unsubstituted or at least monosubstituted, 5- or 6-membered monocyclic ring system;

an unsubstituted or at least monosubstituted, 5- or 6-membered aryl or heteroaryl group, which may be attached via a —$(CH_2)$—, —$(CH_2)_2$, —$(CH_2)_3$, —$(CH_2)_4$, —$C(C_2H_5)(H)$, —$(CH_2)$—O, —$(CH_2)_2$—O, —$(CH_2)_3$—O, —$(CH_2)_4$—O, —O—$(CH_2)$, —O—$(CH_2)_2$, —O—$(CH_2)_3$, —O—$(CH_2)_4$, —$O(C_2H_5)(H)$—O, —O—$C(C_2H_5)(H)$—, —$CH_2$—O—$CH_2$, —$CH_2$—S—$CH_2$, —$C(CH_3)_2$, —$C(H)(CH_3)$ or —CH=CH— group or may be fused with an unsubstituted or at least monosubstituted 5- or 6-membered monocyclic ring system;

a —$C(=O)$—$R^7$ group, which may be attached via a —$(CH_2)$, —$(CH_2)_2$ or —$(CH_2)_3$ group;

a —$C(=O)$—$R^8$ group, which may be attached via a linear or branched $C_{1-3}$ alkylene group which is unsubstituted or mono- or polysubstituted with a phenyl group; or an —N(H)—C(=O)—O—$R^9$ group, which may be attached via a linear or branched $C_{1-8}$ alkylene group which is unsubstituted or mono- or polysubstituted with a phenyl group and which may comprises at least one —N(H)—C(=O) or at least one —C(=O)—N(H) group as a chain link.

11. A compound according to claim 1, wherein $R^5$ represents a member selected from the group consisting of methyl, ethyl, n-propyl, iso-propyl, n-butyl, sec-butyl, tert-butyl, n-pentyl, neopentyl, iso-pentyl, —$C(H)(C_2H_5)_2$, —C(H)

(n—C$_3$H$_7$)$_2$, —CH=CH—CH=CH—CH$_3$, —CH$_2$—CH$_2$—CH=CH$_2$, —CH$_2$—CH$_2$—C(H)(CH$_3$)—(CH$_2$)$_3$—CH$_3$, —CH$_2$—O—CH$_3$ and —CH$_2$—O—CH$_2$—CH$_2$—O—CH$_3$;

- a member selected from the group consisting of cyclopropyl, cyclobutyl, cyclopentyl, cyclohexyl, cycloheptyl, cyclooctyl, piperidinyl, piperazinyl, morpholinyl, tetrahydrofuranyl(tetrahydrofuryl), dithiolanyl, 1,2,3,4-tetrahydroindolyl, 1,2,3,4-tetrahydronaphthyl, 1,3-dihydroisoindolyl, benzooxazolyl and imidazolidinyl, wherein the cyclic group may in each case be attached via a —(CH$_2$), —(CH$_2$)$_2$, —(CH$_2$)$_3$, —(CH$_2$)$_4$, —C(C$_2$H$_5$)(H), —(CH$_2$)—O—, —(CH$_2$)$_2$—O, —(CH$_2$)$_3$—O, —(CH$_2$)$_4$—O, —O—(CH$_2$), —O—(CH$_2$)$_2$, —O—(CH$_2$)$_3$, —O—(CH$_2$)$_4$, —C(C$_2$H$_5$)(H)—O, —O—C(C$_2$H$_5$)(H), —CH$_2$—O—CH$_2$, —CH$_2$—S—CH$_2$, —C(CH$_3$)$_2$—, or —C(H)(CH$_3$) group or may be mono- or polysubstituted, identically or differently, in each case, with a substituent selected from the group consisting of phenyl, —C(=O)—O-tert-butyl, oxo (=O), —S(=O)$_2$-methyl and —S(=O)$_2$-phenyl, and wherein the above-stated phenyl groups may in each case be mono- or polysubstituted, identically or differently, in each case, with a substituent selected from the group consisting of F, Cl, Br and I;
- a member selected from the group consisting of phenyl, naphthyl, furanyl (furyl), thiophenyl(thienyl), pyridinyl, isoxazolyl, triazolyl, pyrazolyl, thiazolyl, benzo[1,2,5]—Oxadiazolyl, 2,3-dihydrobenzofuranyl, quinolinyl, chromanyl, chromenyl, benzo[b]furanyl, benzo[b]thiophenyl, benzo[1,3]-dioxinyl, indolyl, 2,3-dihydroindolyl, 3,4-dihydro-benzo[1,4]oxazinyl and 1,2,3,4-tetrahydroisoquinolinyl, wherein the member may in each case be attached via a —(CH$_2$), —(CH$_2$)$_2$, —(CH$_2$)$_3$, —(CH$_2$)$_4$, —C(C$_2$H$_5$)(H), —(CH$_2$)—O, —(CH$_2$)$_2$—O, —(CH$_2$)$_3$—O, —(CH$_2$)$_4$—O, —O—(CH$_2$), —O—(CH$_2$)$_2$, —O—(CH$_2$)$_3$, —O—(CH$_2$)$_4$, —C(C$_2$H$_5$)(H)—O, —O—C(C$_2$H$_5$)(H), —CH$_2$—O—CH$_2$, —CH$_2$—S—CH$_2$, —C(CH$_3$)$_2$, —C(H)(CH$_3$) or —CH=CH— group or may be mono- or polysubstituted, identically or differently, in each case, with a substituent selected from the group consisting of F, Cl, Br, I, —CN, —NO$_2$, —OH, —SH, methyl, ethyl, n-propyl, iso-propyl, n-butyl, iso-butyl, sec-butyl, tert-butyl, n-pentyl, iso-pentyl, neopentyl, methoxy, ethoxy, n-propoxy, iso-propoxy, n-butyloxy, iso-butyloxy, sec-butyloxy, tert-butyloxy, —S-methyl, —S-ethyl, —CF$_3$, —CHF$_2$, —CH$_2$F, —O—CF$_3$, —O—CHF$_2$, —O—CH$_2$F, —S—CF$_3$, —S—CHF$_2$, —S—CH$_2$F, —S(=O)$_2$-phenyl, pyrazolyl, phenyl, —N(CH$_3$)$_2$, —N(C$_2$H$_5$)$_2$, —CH$_2$—O—C(=O)-phenyl, —O—C(=O)-phenyl, furyl, thiadiazolyl, thiophenyl, phenoxy and benzyl, and wherein the cyclic substituents may themselves be mono- or polysubstituted, identically or differently, in each case, with a substituent selected from the group consisting of F, Cl, Br, I,
- a —C(=O)—R$^7$ residue, which may be attached via a —(CH$_2$), —(CH$_2$)$_2$ or —(CH$_2$)$_3$ group,
- a —C(=O)—O—R$^8$ residue, which may be attached via a —(CH$_2$), —(CH$_2$)$_2$, —(CH$_2$)$_3$ or —C(H)(phenyl) group, or
- an —N(H)—C(=O)—O—R$^9$ residue, which may be attached via a —(CH$_2$), —(CH$_2$)$_2$, —(CH$_2$)$_3$, —(CH$_2$)$_4$, —(CH$_2$)$_5$, —C(H)(CH$_2$phenyl), —C(H)(phenyl), —C(H)(C(H)(CH$_3$)$_2$) or —C(H)(CH$_2$—CH(CH$_3$)$_2$)—NH—C(=O)—CH$_2$ group.

12. A compound according to claim 1, wherein R$^6$ represents —NR$^{10}$R$^{11}$;

- a linear or branched, unsubstituted C$_{1-10}$ alkyl group, a linear or branched, unsubstituted C$_{2-10}$ alkenyl group, a linear or branched, unsubstituted C$_{2-10}$ alkynyl group;
- an unsubstituted or at least monosubstituted, saturated or unsaturated 3-, 4-, 5-, 6-, 7- or 8-membered cycloaliphatic group, which may be attached via a linear or branched C$_{1-3}$ alkylene group or may be bridged with a linear or branched C$_{1-3}$ alkylene group; or
- an unsubstituted or at least monosubstituted 5- to 6-membered aryl or heteroaryl group, which may be attached via a linear or branched C$_{1-6}$ alkylene group or may be fused with an unsubstituted or at least monosubstituted 5- or 6-membered monocyclic ring system.

13. A compound according to claim 1, wherein R$^6$ represents

- a linear or branched, unsubstituted C$_{1-5}$ alkyl group, a linear or branched, unsubstituted C$_{2-5}$ alkenyl group, a linear or branched, unsubstituted C$_{2-5}$ alkynyl group;
- an unsubstituted or at least monosubstituted, saturated or unsaturated, 5-, 6- or 7-membered cycloaliphatic group, which may be attached via a —(CH$_2$), —(CH$_2$) or —(CH$_2$)$_3$ group or may be bridged with a —(C)(CH$_3$)$_2$ group; or
- an unsubstituted or at least monosubstituted, 5- or 6-membered aryl or heteroaryl group, which may be attached via a —(CH$_2$), —(CH$_2$)$_2$, or —(CH$_2$)$_3$ group or may be fused with an unsubstituted or at least monosubstituted, 5- or 6-membered monocyclic ring system, which may contain one or more oxygen atoms as ring members or one or more nitrogen atoms as ring members.

14. A compound according to claim 1, wherein R$^6$ represents a methyl, ethyl, n-propyl, iso-propyl, n-butyl, iso-butyl, sec-butyl or tert-butyl group;

- a 7,7-dimethyl-2-oxo-bicyclo[2.2.1]heptyl group which may be attached via a —(CH$_2$), —(CH$_2$)$_2$ or —(CH$_2$)$_3$ group; or
- a phenyl, naphthyl, thiophenyl (thienyl), furanyl, (furyl), thiazolyl, pyrazolyl, 2,3-dihydro-benzo [1,4]-dioxinyl, 1,2,3,4-tetrahydroiso-quinolinyl or 3,4-dihydro-benzo [1,4]oxazinyl group, which may be attached via a —(CH$_2$) —(CH$_2$) or —(CH$_2$)$_3$ group or may be mono- or polysubstituted, identically or differently, in each case, with a substituent selected from the group consisting of F, Cl, Br, I, methyl, ethyl, n-propyl, iso-propyl, n-butyl, iso-butyl, sec-butyl, tert-butyl, n-pentyl, iso-pentyl, neopentyl, methoxy, ethoxy, —CN, —CF$_3$, —CF$_2$H, —CFH$_2$, —NO$_2$, —C(=O)—CF$_3$, —O—CF$_3$, —C(=O)—O—CH$_3$, —C(=O)—O—C$_2$H$_5$, —NH—C(=O)—CH$_3$, —S(=O)$_2$—CH$_3$ and phenyl.

15. A compound according to claim 1, wherein R$^7$ represents a linear or branched, unsubstituted C$_{1-3}$ alkyl group; an unsubstituted, 5- or 6-membered aryl or heteroaryl group; an unsubstituted, saturated or unsaturated 5-, 6- or 7-membered cycloaliphatic group, which may comprise a nitrogen atom as a ring member, which group may be fused with an unsubstituted, 6-membered monocyclic ring system; or an —NR$^{7a}$R$^{7b}$ group, in which R$^{7a}$ and R$^{7b}$, identical or different, in each case, represent a linear or branched C$_{1-3}$ alkyl group.

16. A compound according to claim 1, wherein R$^7$ represents a methyl, ethyl, n-propyl, phenyl, indolyl, 2,3-dihydroindolyl, dimethylamino or diethylamino group.

17. A compound according to claim 1, wherein $R^8$ represents a linear or branched, unsubstituted $C_{1-3}$ alkyl group or a phenyl group which may be attached via a linear or branched $C_{1-3}$ alkylene group.

18. A compound according to claim 1, wherein $R^5$ represents a methyl, ethyl, phenyl or benzyl group.

19. A compound according to claim 1, wherein $R^9$ represents a linear or branched, unsubstituted $C_{1-3}$ alkyl group, an unsubstituted 5- or 6-membered aryl or heteroaryl group which may be attached via a linear or branched $C_{1-3}$ alkylene group, or an unsubstituted or at least monosubstituted, saturated or unsaturated, 5- or 6-membered cycloaliphatic group, which may be fused with at least one unsubstituted, 6-membered monocyclic ring system.

20. A compound according to claim 1, wherein $R^9$ represents a methyl, ethyl, n-propyl, iso-propyl, n-butyl, iso-butyl, sec-butyl, tert-butyl, or a phenyl or fluorenyl group which maybe be attached via a —($CH_2$) group.

21. A compound according to claim 1, wherein $R^{10}$ and $R^{11}$, identical or different, in each case, represent a methyl, ethyl, n-propyl or iso-propyl group.

22. A compound according to claim 1, wherein
X represents an $NR^{2a}$ group;
$R^1$ represents a —C(=O)—$R^3$ group or a —C(=O)—O—$R^4$ group;
$R^{2a}$ represents a —C(=O)—$R^5$ group or an —S(=O)$_2$—$R^6$ group;
$R^3$ denotes a linear or branched, $C_{1-10}$ alkyl group, $C_{2-10}$ alkenyl group or $C_{2-10}$ alkynyl group which may be substituted and which may comprise 1, 2 or 3 heteroatoms selected from the group consisting of O, S and NH as chain links;
an unsaturated or saturated, 3-, 4-, 5-, 6-, 7-, 8- or 9-membered cycloaliphatic group;
a 5- to 14-membered aryl or heteroaryl group which may be substituted;
(CHR$^{12}$)—U$_a$—(CH$_2$)$_b$—V$_c$(CH$_2$)$_d$—R$^{13}$ wherein a=0 or 1, b=0 or 1, c=0 or 1 and d 0 or 1, and U and V, identically or differently, in each case, represent O, S and NH; or
—(CHR$^{14}$)—(CH$_2$)$_e$—R$^{15}$ wherein e =0, 1, 2 or 3;
$R^4$ represents a 5- to 14-membered aryl or heteroaryl group which may be substituted; or
—(CHR$^{16}$)—(CH$_2$)$_f$—R$^{17}$ wherein f=0, 1, 2 or 3;
$R^5$ represents a linear or branched, $C_{1-10}$ alkyl group, $C_{2-10}$ alkenyl group or $C_{2-10}$ alkynyl group which may be substituted and may comprise 1, 2 or 3 heteroatoms selected from the group consisting of O, S and NH as chain links;
an unsaturated or saturated, 3-, 4-, 5-, 6-, 7-, 8- or 9-membered cycloaliphatic group, which may be substituted and may be fused with a saturated, unsaturated or aromatic, mono- or polycyclic ring system which may be substituted;
a 5- to 14-membered aryl or heteroaryl group, which may be substituted and may be fused with a saturated or unsaturated, mono- or polycyclic ring system which may be substituted;
(CHR$^{18}$)$_g$—(CH$_2$)$_h$—C(=O)—R$^7$ wherein g=0 or 1 and h=0, 1, 2 or 3;
—(CHR$^{19}$)$_j$—(CH$_2$)$_k$—C(=O)—O—R$^8$ wherein j=0 or 1 and k=0, 1, 2 or 3;
—(CHR$^{20}$)$_m$—(CH$_2$)$_n$NH—C(=O)]$_p$—(CH$_2$)$_q$—NH—C(=O)—O—R$^9$ wherein m=0 or 1; n=0, 1, 2, 3, 4 or 5; p=0 or 1 and q=0, 1 or 2;
—(CR$^{21}$R$^{22}$)—W$_r$—(CH$_2$)$_s$—X$_t$—(CH$_2$)$_u$—Y$_v$—R$^{23}$ wherein r=0 or 1, s=0 or 1, t=0 or 1, u =0, 1 or 2 and v=0 or 1, and wherein W, X and Y, identically or differently, in each case, represent O, S or NH;
or —CH=CH—R$^{24}$;
$R^6$ represents a linear or branched $C_{1-10}$ alkyl group, $C_{2-10}$ alkenyl group or $C_{2-10}$ alkynyl group which may comprise 1, 2 or 3 heteroatoms selected from the group consisting of O, S, and NH as chain links;
an unsaturated or saturated, 3-, 4-, 5-, 6-, 7-, 8- or 9-membered cycloaliphatic group, which may be substituted and which may be fused with a saturated, unsaturated or aromatic, mono- or polycyclic ring system which may be substituted or may be bridged with a linear or branched $C_{1-5}$ alkylene group;
a 5- to 14-membered aryl or heteroaryl group which may be substituted, and which may be fused with a saturated or unsaturated, mono- or polycyclic ring system which may be substituted;
—(CHR$^{25}$)-Z$_w$—(CH$_2$)$_x$-A)$_y$—(CH$_2$)$_z$—R$^{26}$ wherein w=0 or 1, x=0 or 1, y=0 or 1 and z=0 or 1, wherein Z and A, identically or differently, in each case, represent O, S or NH; or
—(CHR$^{27}$)—(CH$_2$)$_{aa}$—R$^{28}$ wherein aa=0, 1, 2 or 3;
$R^7$ represents a linear or branched, $C_{1-10}$ alkyl group which may be substituted;
an unsaturated or saturated, 3-, 4-, 5-, 6-, 7-, 8- or 9-membered cycloaliphatic group which may be substituted, or which may be fused with a saturated, unsaturated or aromatic, mono- or polycyclic ring system which may be substituted;
a 5- to 14-membered aryl or heteroaryl group which may be substituted; or
an —NR$^{7a}$R$^{7b}$ group, wherein R$^{7a}$ and R$^{7b}$, identically or differently, in each case, represent a linear or branched $C_{1-10}$ alkyl group;
$R^8$ represents a linear or branched, $C_{1-10}$ alkyl group which may be substituted; or
a 5- to 14-membered aryl or heteroaryl group which may be substituted, and which may be attached via a linear or branched $C_{1-5}$-alkylene group;
$R^9$ represents a linear or branched, $C_{1-10}$ alkyl group which may be substituted;
an unsaturated or saturated, 3-, 4-, 5-, 6-, 7-, 8- or 9-membered cycloaliphatic group which may be substituted, which group may be fused with a saturated, unsaturated or aromatic, mono- or polycyclic ring system which may be substituted or which group may be attached via a linear or branched $C_{1-5}$ alkylene group; or
a 5- to 14-membered aryl or heteroaryl group which may be substituted and which may be attached via a linear or branched $C_{1-5}$ alkylene group;
$R^{10}$ and $R^{11}$, identically or differently, in each case, represent a linear or branched,
$C_{1-10}$ alkyl group which may be substituted;
$R^{12}$, $R^{14}$, $R^{16}$, $R^{18}$, $R^{21}$, $R^{22}$, $R^{25}$ and $R^{27}$, identically or differently, in each case,
represent hydrogen or
a linear or branched, $C_{1-10}$ alkyl group which may be substituted;
$R^{13}$ represents an unsaturated or saturated, 3-, 4-, 5-, 6-, 7-, 8- or 9-membered cycloaliphatic group which may be substituted;
$R^{15}$ and $R^{17}$, identically or differently, in each case, represent a 5- to 14-membered aryl or heteroaryl group which may be substituted;
$R^{19}$ represents hydrogen;

a linear or branched, $C_{1-10}$ alkyl group which may be substituted; or a phenyl group;

$R^{20}$ represents hydrogen;

a linear or branched, $C_{1-10}$ alkyl group which may be substituted; or a phenyl group, which may be attached via a linear or branched $C_{1-5}$ alkylene group;

$R^{23}$ represents an unsaturated or saturated, 3-, 4-, 5-, 6-, 7-, 8- or 9-membered cycloaliphatic group which may be substituted and which may be fused with a saturated, unsaturated or aromatic, mono- or polycyclic ring system which may be substituted; or a 5- to 14-membered aryl or heteroaryl group which may be substituted and which may be fused with a saturated or unsaturated, mono- or polycyclic ring system which may be substituted;

$R^{24}$ and $R^{28}$, identically or differently, in each case, represent a 5- to 14-membered aryl or heteroaryl group which may be substituted and which may be fused with a saturated or unsaturated, mono- or polycyclic ring system which may be substituted; and $R^{26}$ represents an unsaturated or saturated, 3-, 4-, 5-, 6-, 7-, 8- or 9-membered cycloaliphatic group which may be substituted and which may be fused with a saturated, unsaturated or aromatic, mono- or polycyclic ring system which may be substituted or which group may be bridged with a linear or branched $C_{1-5}$ alkylene group;

wherein the above-stated $C_{1-10}$ alkyl groups may be unsubstituted or substituted with 1, 2, 3, 4 or 5 substituents, identically or differently, in each case, selected from the group consisting of F, Cl, Br, I, —CN, —NO$_2$, —OH, —SH and —NH$_2$;

the above-stated $C_{2-10}$ alkenyl groups may be unsubstituted or substituted with 1, 2, 3, 4 or 5 substituents, identically or differently, in each case, selected from the group consisting of F, Cl, Br, I, —CN, —NO$_2$, —OH, —SH and —NH$_2$;

the above-stated $C_{2-10}$ alkynyl groups may be unsubstituted or substituted with 1, 2, 3, 4 or 5 substituents, identically or differently, in each case, selected from the group consisting of F, Cl, Br, I, —CN, —NO$_2$, —OH, —SH and —NH$_2$;

the above-stated cycloaliphatic groups may be unsubstituted or substituted with 1, 2, 3, 4 or 5 substituents, identically or differently, in each case, selected from the group consisting of oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, C$_{1-5}$-alkyl, —C(=O)—H, —C(=O)—C$_{1-5}$-alkyl, —C(=O)—C$_{1-5}$-perfluoroalkyl, —C(=O)—OH, —C(=O)—O—C$_{1-5}$-alkyl, —(CH$_2$)—C(=O)—OH, —(CH$_2$)—C(=O)—O—C$_{1-5}$-alkyl, —NH—C$_{1-5}$-alkyl, —N(C$_{1-5}$-alkyl)$_2$, —NH—C(=O)—O—C$_{1-5}$-alkyl, —NH—C(=O)—C$_{1-5}$-alkyl, —C(=O)—NH$_2$, —C(=O)—NH—C$_{1-5}$-alkyl, —C(=O)—N—(C$_{1-5}$-alkyl)$_2$, —S(=O)$_2$—NH$_2$, —S(=O)$_2$—NH—C$_{1-5}$-alkyl, —S(=O)$_2$—NH-phenyl, —S(=O)$_2$—C$_{1-5}$-alkyl, —S(=O)$_2$-phenyl, —(CH$_2$)-benzo[b]furanyl, —O-phenyl, —O-benzyl, phenyl, benzyl, naphthyl and —(CH$_2$)—naphthyl, wherein in each case the cyclic moiety of the groups —O-phenyl, —S(=O)$_2$—NH-phenyl, —S(=O)$_2$-phenyl, —O-benzyl, phenyl, —(CH$_2$)-benzo[b]furanyl, benzyl, naphthyl and —(CH$_2$)-naphthyl may be substituted with 1, 2, 3, 4 or 5 substituents, identically or differently, in each case, selected from the group consisting of F, Cl, Br, —OH, —CF$_3$, —SF$_5$, —CN, —NO$_2$, —O—C$_{1-5}$-alkyl, C$_{1-5}$-alkyl, —O—CF$_3$, —S—CF$_3$, phenyl and —O-benzyl, and the above-stated cycloaliphatic groups may comprise 1, 2, 3, 4 or 5 heteroatoms, identically or differently, in each case, selected from the group consisting of oxygen, nitrogen and sulfur; and the above-stated aryl- or heteroaryl groups may be unsubstituted or substituted, identically or differently, in each case, with 1, 2, 3, 4 or 5 substituents selected from the group consisting of F, Cl, Br, I, —CN, —CF$_3$, —SF$_5$, —OH, —O—C$_{1-5}$-alkyl, —O—C$_{2-5}$-alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$-alkyl, C$_{1-5}$-alkyl, —C(=O)—OH, —C(=O)—O—C$_{1-5}$-alkyl, —O—C(=O)—C$_{1-5}$-alkyl, —O—C(=O)-phenyl, —(CH$_2$)—O—C(=O)—C$_{1-5}$-alkyl, —(CH$_2$)—O—C(=O)-phenyl, —NH—C$_{1-5}$-alkyl, —N(C$_{1-5}$-alkyl)$_2$, —NH—C(=O)—O—C$_{1-5}$-alkyl, —NH—C(=O)—C$_{1-5}$-alkyl, —C(=O)—H, —C(=O)—C$_{1-5}$-alkyl, —C(=O)—C$_{1-5}$-perfluoroalkyl, —C(=O)—NH$_2$, —C(=O)—NH—C$_{1-5}$-alkyl, —C(=O)—N—(C$_{1-5}$-alkyl)$_2$, —S(=O)$_2$—NH$_2$, —S(=O)$_2$—NH—C$_{1-5}$-alkyl, —S(=O)$_2$—NH-phenyl, —S(=O)$_2$—C$_{1-5}$-alkyl, —S(=O)$_2$-phenyl, —(CH$_2$)-benzo[b]furanyl, —O-phenyl, —S-phenyl, —S-benzyl, —O-benzyl, phenyl, furanyl, thienyl(thiophenyl), pyrazolyl, thiadiazolyl and benzyl, wherein in each case the cyclic moiety of the groups —O—C(=O)-phenyl, —(CH$_2$)—O—C(=O)-phenyl, —S(=O)$_2$—NH-phenyl, —S(=O)$_2$-phenyl, —O-phenyl, —S-phenyl, —S-benzyl, —O-benzyl, phenyl, furanyl, thienyl, pyrazolyl, thiadiazolyl, —(CH$_2$)-benzo[b]furanyl and benzyl may be substituted with 1, 2, 3, 4 or 5 substituents mutually independently selected from the group consisting of F, Cl, Br, —OH, —CF$_3$, —SF$_5$, —CN, —NO$_2$, —O—C$_{1-5}$-alkyl, C$_{1-5}$-alkyl, —O—CF$_3$, —S—CF$_3$, phenyl and —O-benzyl; and and the above-stated heteroaryl groups may, in each case, comprise 1, 2, 3, 4 or 5 heteroatoms as ring members, which are, identically or differently, in each case, selected from the group consisting of oxygen, nitrogen and sulfur;

the rings of the above-stated mono- or polycyclic ring systems may be unsubstituted or substituted, identically or differently, in each case, with 1, 2, 3, 4 or 5 substituents mutually independently selected from the group consisting of oxo (=O), thioxo (=S), F, Cl, Br, I, —CN, —CF$_3$, —SF$_5$, —OH, —O—C$_{1-5}$-alkyl, —O—C$_{2-5}$-alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$-alkyl, C$_{1-5}$-alkyl, —C(=O)—OH, —C(=O)—O—C$_{1-5}$-alkyl, —O—C(=O)—C$_{1-5}$-alkyl, —O—C(=O)-phenyl, —(CH$_2$)—O—C(=O)—C$_{1-5}$-alkyl, —(CH$_2$)—O—C(=O)-phenyl, —NH—C$_{1-5}$-alkyl, —N(C$_{1-5}$-alkyl)$_2$, —NH—C(=O)—O—C$_{1-5}$-alkyl, —NH—C(=O)—C$_{1-5}$-alkyl, —C(=O)—H, —C(=O)—C$_{1-5}$-alkyl, —C(=O)—C$_{1-5}$-perfluoroalkyl, —C(=O)—NH$_2$, —C(=O)—NH—C$_{1-5}$-alkyl, —C(=O)—N—(C$_{1-5}$-alkyl)$_2$, —S(=O)$_2$—NH$_2$, —S(=O)$_2$—NH—C$_{1-5}$-alkyl, —S(=O)$_2$—NH-phenyl, —S(=O)$_2$—C$_{1-5}$-alkyl, —S(=O)$_2$-phenyl, —(CH$_2$)-benzo[b]furanyl, —O-phenyl, —S-phenyl, —S-benzyl, —O-benzyl, phenyl, furanyl, thienyl, pyrazolyl, thiadiazolyl and benzyl, wherein in each case the cyclic moiety of the groups —O—C(=O)-phenyl, —(CH$_2$)—O—C(=O)-phenyl, —S(=O)$_2$—NH-phenyl, —S(=O)$_2$-phenyl, —O-phenyl, —S-phenyl, —S-benzyl, —O-benzyl, phenyl, furanyl, thienyl, pyrazolyl, thiadiazolyl, —(CH$_2$)-benzo[b]furanyl and benzyl may be substituted with 1, 2, 3, 4 or 5 substituents, identically or differently, in each case, selected from the group consisting of F, Cl, Br, —OH, —CF$_3$, —SF$_5$, —CN, —NO$_2$, —O—C$_{1-5}$-alkyl, C$_{1-5}$-alkyl, —O—CF$_3$, —S—CF$_3$, phenyl and —O-benzyl; and the rings of the above-stated mono- or polycyclic ring systems are in each case 5-, 6- or 7-membered and may, identically or differently, in each case, comprise 1, 2, 3, 4 or 5 heteroatoms as ring members, which are, identically or differently, in each case, selected from the group consisting of oxygen, nitrogen and sulfur.

23. A compound according to claim 22, wherein
R$^3$ represents a member selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, 2-hexyl, 3-hexyl, -(CH$_2$)—(CH$_2$)—(C(CH$_3$)$_3$), n-heptyl, 3-heptyl, 4-heptyl, n-octyl, —(CH$_2$)—(CH$_2$)—(CH)(CH$_3$)—(CH$_2$)—(CH$_2$)—(CH$_2$)—(CH$_3$), vinyl, 1-propenyl, 2-propenyl, 1-butenyl, 2-butenyl, 3-butenyl, —CH=CH—CH=CH—CH$_3$, —CH$_2$—O—CH$_3$, —CH$_2$—O—CH$_2$—CH$_2$—O—CH$_3$, —CH$_2$—S—CH$_3$, —CH$_2$—S—CH$_2$—CH$_2$—S—CH$_3$, —CH$_2$—NH—CH$_3$ and —CH$_2$—NH—CH$_2$—CH$_3$;

a (hetero)cycloaliphatic group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl and dithiolanyl, wherein the (hetero)cycloaliphatic group may be substituted with 1, 2, 3, 4 or 5 substituents, identically or differently, in each case, selected from the group consisting of oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, C$_{1-5}$-alkyl, —C(=O)—H, —C(=O)—C$_{1-5}$-alkyl, —C(=O)—C$_{1-5}$-perfluoroalkyl, —C(=O)—OH, —C(=O)—O—C$_{1-5}$-alkyl, —(CH$_2$)—C(=O)—OH, —(CH$_2$)—C(=O)—O—C$_{1-5}$-alkyl, —NH—C$_{1-5}$-alkyl, —N(C$_{1-5}$-alkyl)$_2$, —O-phenyl, —O-benzyl, phenyl and benzyl, and wherein in each case the cyclic moiety of the groups —O-phenyl, —O-benzyl, phenyl and benzyl may be substituted with 1, 2, 3, 4 or 5 substituents, identically or differently, in each case, selected from the group consisting of F, Cl, Br, —OH, —CF$_3$, —SF$_5$, —CN, —NO$_2$, —O—C$_{1-5}$-alkyl, C$_{1-5}$-alkyl, —O—CF$_3$, —S—CF$_3$, phenyl and —O-benzyl;

a member selected from the group consisting of phenyl, naphthyl, thiophenyl, furanyl, pyrrolyl, pyrazolyl, pyrazinyl, triazolyl, pyridinyl, imidazolyl, indolyl, isoindolyl, benzo[b]furanyl, benzo[b]thiophenyl, thiazolyl, thiadiazolyl, oxazolyl, isoxazolyl, pyridazinyl, pyrazinyl, pyrimidinyl, indazolyl, quinazolinyl, quinolinyl, isoquinolinyl, phenazinyl, phenothiazinyl and oxadiazolyl, wherein the residue may be substituted with 1, 2, 3, 4 or 5 substituents, identically or differently, in each case, selected from the group consisting of F, Cl, Br, I, —CN, —CF$_3$, —SF$_5$, —OH, —O—C$_{1-5}$-alkyl, —O—C$_{2-5}$-alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$-alkyl, C$_{1-5}$-alkyl, —C(=O)—OH, —C(=O)—O—C$_{1-5}$-alkyl, —O—C(=O)—C$_{1-5}$-alkyl, —O—C(=O)-phenyl, —(CH$_2$)—O—C(=O)—C$_{1-5}$-alkyl, —(CH$_2$)—O—C(=O)-phenyl, —NH—C$_{1-5}$-alkyl, —N(C$_{1-5}$-alkyl)$_2$, —NH—C(=O)—O—C$_{1-5}$-alkyl, —NH—C(=O)—C$_{1-5}$-alkyl, —C(=O)—H, —C(=O)—C$_{1-5}$-alkyl, —C(=O)—C$_{1-5}$-perfluoroalkyl, —C(=O)—NH$_2$, —C(=O)—NH—C$_{1-5}$-alkyl, —C(=O)—N—(C$_{1-5}$-alkyl)$_2$, —S(=O)$_2$—NH$_2$, —S(=O)$_2$—NH—C$_{1-5}$-alkyl, —S(=O)$_2$—NH-phenyl, —S(=O)$_2$—C$_{1-5}$-alkyl, —S(=O)$_2$-phenyl, —O-phenyl, —S-phenyl, —S-benzyl, —O-benzyl, phenyl and benzyl, and wherein in each case the cyclic moiety of the groups —O—C(=O)-phenyl, —(CH$_2$)—O—C(=O)-phenyl, —S(=O)$_2$—NH-phenyl, —S(=O)$_2$-phenyl, —O-phenyl, —S-phenyl, —S-benzyl, —O-benzyl, phenyl and benzyl may be substituted with 1, 2, 3, 4 or 5 substituents, identically or differently, in each case, selected from the group consisting of F, Cl, Br, —OH, —CF$_3$, —SF$_5$, —CN, —NO$_2$, —O—C$_{1-5}$-alkyl, C$_{1-5}$-alkyl, —O—CF$_3$, —S—CF$_3$, phenyl and —O-benzyl;

—(CHR$^{12}$)—R$^3$, —(CHR$^{12}$)—(CH$_2$)—R$^{13}$, —(CHR$^{12}$)—O—R$^{13}$, —(CHR$^{12}$)—S—R$^3$, —(CHR$^{12}$)—NH—R$^{13}$, —(CHR$^{12}$)—(CH$_2$)—(CH$_2$)—R$^{13}$, —(CHR$^{12}$)—(CH$_2$)—O—R$^{13}$, —(CHR$^{12}$)—(CH$_2$)—S—R$^{13}$, —(CHR$^{12}$)—(CH$_2$)—NH—R$^{13}$, —(CHR$^{12}$)—(CH$_2$)—O—(CH$_2$)—R$^{13}$, —(CHR$^{12}$)—(CH$_2$)—S—(CH$_2$)—R$^{13}$ or —(CHR$^{12}$)—(CH$_2$)—NH—R$^{13}$; or
—(CHR$^{14}$)—R$^5$, —(CHR$^{14}$)—(CH$_2$)—R$^{15}$ or —(CHR$^{14}$)—(CH$_2$)—(CH$_2$)—R$^{15}$;

R$^4$ represents a member selected from the group consisting of phenyl, naphthyl, thiophenyl, furanyl, pyrrolyl, pyrazolyl, pyrazinyl, triazolyl, pyridinyl, imidazolyl, indolyl, isoindolyl, benzo[b]furanyl, benzo[b]thiophenyl, thiazolyl, thiadiazolyl, oxazolyl, isoxazolyl, pyridazinyl, pyrazinyl, pyrimidinyl, indazolyl, quinazolinyl, quinolinyl, isoquinolinyl, phenazinyl, phenothiazinyl and oxadiazolyl, wherein the member may be substituted with 1, 2, 3, 4 or 5 substituents, identically or differently, in each case, selected from the group consisting of F, Cl, Br, I, —CN, —CF$_3$, —SF$_5$, —OH, —O—C$_{1-5}$-alkyl, —O—C$_{2-5}$-alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$-alkyl, C$_{1-5}$-alkyl, —C(=O)—OH, —C(=O)—O—C$_{1-5}$-alkyl, —O—C(=O)—C$_{1-5}$-alkyl, —O—C(=O)-phenyl, —(CH$_2$)—O—C(=O)—C$_{1-5}$-alkyl, —(CH$_2$)—O—C(=O)-phenyl, —NH—C$_{1-5}$-alkyl, —N(C$_{1-5}$-alkyl)$_2$, —NH—C(=O)—O—C$_{1-5}$-alkyl, —NH—C(=O)—C$_{1-5}$-alkyl, —C(=O)—H, —C(=O)—C$_{1-5}$-alkyl, —C(=O)—C$_{1-5}$-perfluoroalkyl, —C(=O)—NH$_2$, —C(=O)—NH—C$_{1-5}$-alkyl, —C(=O)—N—(C$_{1-5}$-alkyl)$_2$, —S(=O)$_2$—NH$_2$, —S(=O)$_2$—NH—C$_{1-5}$-alkyl, —S(=O)$_2$—NH-phenyl, —S(=O)$_2$—C$_{1-5}$-alkyl, —S(=O)$_2$-phenyl, —O-phenyl, —S-phenyl, —S-benzyl, —O-benzyl, phenyl and benzyl, and wherein in each case the cyclic moiety of the groups —O—C(=O)-phenyl, —(CH$_2$)—O—C(=O)-phenyl, —S(=O)$_2$—NH-phenyl, —S(=O)$_2$- phenyl, —O-phenyl, —S-phenyl, —S-benzyl, —O-benzyl, phenyl and benzyl may be substituted with 1, 2, 3, 4 or 5 substituents selected, identically or differently, in each case, from the group consisting of F, Cl, Br, —OH, —CF$_3$, —SF$_5$, —CN, —NO$_2$, —O—C$_{1-5}$-alkyl, —C$_{1-5}$ alkyl, —O—CF$_3$, —S—CF$_3$, phenyl and —O-benzyl; or
—(CHR$^{16}$)—R$^{17}$, —(CHR$^{16}$)—(CH$_2$)—R$^{17}$ or —(CHR$^{16}$)—(CH$_2$)—(CH$_2$)—R$^{17}$;

R$^5$ represents a member selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, 2-hexyl, 3-hexyl, —(CH$_2$)—(CH$_2$)—(C(CH$_3$)$_3$), n-heptyl, 3-heptyl, 4-heptyl, n—octyl, —(CH$_2$)—(CH$_2$)—(CH)(CH$_3$)—(CH$_2$)—(CH$_2$)—(CH$_2$)—(CH$_3$), vinyl, 1-propenyl, 2-propenyl, 1-butenyl, 2-butenyl, 3-butenyl, —CH=CH—CH=CH—CH$_3$, —CH$_2$—O—CH$_3$, —CH$_2$—O—CH$_2$—CH$_2$—O—CH$_3$, —CH$_2$—S—CH$_3$, —CH$_2$—S—CH$_2$—CH$_2$—S—CH$_3$, —CH$_2$—NH—CH$_3$ and —CH$_2$—NH—CH$_2$—CH$_3$;

a member selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, (1,2,3,4)-tetrahydronaphthyl, (1,3)-dihydroisoindolyl, (2,3)-dihydroindolyl and 3,4-dihydro-2H-benzo[1,4]oxazinyl, wherein the (hetero)cycloaliphatic residue may be substituted with 1, 2, 3, 4 or 5 substituents selected, identically or differently, in each case, from the group consisting of oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$ alkyl, —C(=O)—H, —C(=O)—C$_{1-5}$-alkyl, —C(=O)—C$_{1-5}$-perfluoroalkyl, —C(=O)—OH, —C(=O)—O—C$_{1-5}$-alkyl, —(CH$_2$)—C(=O)—OH, —(CH$_2$)—C(=O)—O—C$_{1-5}$-alkyl, —NH—C$_{1-5}$-alkyl, —N(C$_{1-5}$-alkyl)$_2$, —O-phenyl, —O-benzyl, phenyl and benzyl, and wherein in each case the cyclic moiety of the groups —O-phenyl, —O-benzyl, phenyl and benzyl may be substituted with 1, 2, 3, 4 or 5 substituents selected from the group consisting of F, Cl, Br, —OH, —CF$_3$, —SF$_5$, —CN, —NO$_2$, —O—C$_{1-5}$-alkyl, —C$_{1-5}$ alkyl, —O—CF$_3$, —S—CF$_3$, phenyl and —O-benzyl;

a member selected from the group consisting of phenyl, naphthyl, thiophenyl, furanyl, pyrrolyl, pyrazolyl, pyrazinyl, triazolyl, pyridinyl, imidazolyl, indolyl, isoindolyl, benzo[b]furanyl, benzo[b]thiophenyl, thiazolyl, thiadiazolyl, oxazolyl, isoxazolyl, pyridazinyl, pyrazinyl, pyrimidinyl, indazolyl, quinazolinyl, quinolinyl, isoquinolinyl, phenazinyl, phenothiazinyl, oxadiazolyl, benzo[1,2,5]oxadiazolyl, (3,4)-dihydro-2H-benzo[1,4]oxazinyl, (2,3)-dihydro-benzo[1,4]dioxinyl, benzo[1,3]dioxinyl, (2,3)-dihydrobenzofuranyl, 2H-chromenyl, chromanyl and (1,2,3,4)-tetrahydroisoquinolinyl, wherein the residue may be substituted with 1, 2, 3, 4 or 5 substituents selected, identically or differently, in each case, from the group consisting of F, Cl, Br, I, —CN, —CF$_3$, —SF$_5$, —OH, —O—C$_{1-5}$-alkyl, —O—C$_{2-5}$-alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$-alkyl, —C$_{1-5}$ alkyl, —C(=O)—OH, —C(=O)—O—C$_{1-5}$-alkyl, —O—C(=O)—C$_{1-5}$-alkyl, —O—C(=O)-phenyl, —(CH$_2$)—O—C(=O)—C$_{1-5}$-alkyl, —(CH$_2$)—O—C(=O)-phenyl, —NH—C$_{1-5}$-alkyl, —N(C$_{1-5}$-alkyl)$_2$, —NH—C(=O)—O—C$_{1-5}$-alkyl, —NH—C(=O)—C$_{1-5}$-alkyl, —C(=O)—H, —C(=O)—C$_{1-5}$-alkyl, —C(=O)—C$_{1-5}$-perfluoroalkyl, —C(=O)—NH$_2$, —C(=O)—NH—C$_{1-5}$-alkyl, —C(=O)—N—(C$_{1-5}$-alkyl)$_2$, —S(=O)$_2$—NH$_2$, —S(=O)$_2$—NH—C$_{1-5}$-alkyl, —S(=O)$_2$—NH-phenyl, —S(=O)$_2$—C$_{1-5}$-alkyl, —S(=O)$_2$-phenyl, —O-phenyl, —S-phenyl, —S-benzyl, —O-benzyl, phenyl, pyrazolyl, thienyl, furanyl, thiadiazolyl and benzyl, and wherein in each case the cyclic moiety of the groups —O—C(=O)-phenyl, —(CH$_2$)—O—C(=O)-phenyl, —S(=O)$_2$—NH-phenyl, —S(=O)$_2$-phenyl, —O-phenyl, —S-phenyl, —S-benzyl, —O-benzyl, phenyl, pyrazolyl, thienyl, furanyl, thiadiazolyl and benzyl may be substituted with 1, 2, 3, 4 or 5 substituents selected, identically or differently, in each case, from the group consisting of F, Cl, Br, —OH, —CF$_3$, —SF$_5$, —CN, —NO$_2$, —O—C$_{1-5}$-alkyl, —C$_{1-5}$ alkyl, —O—CF$_3$, —S—CF$_3$, phenyl and —O-benzyl;

—C(=O)—R$^7$, —(CHR$^{18}$)—C(=O)—R$^7$, —(CHR$^{18}$)—(CH$_2$)—C(=O)—R$^7$ or —(CHR$^{18}$)—(CH$_2$)—(CH$_2$)—C(=O)—R$_7$;

—C(=O)—O—R$^8$, —(CHR$^{19}$)—C(=O)—O—R$^8$, —(CHR$^{19}$)—(CH$_2$)—C(=O)—O—R$^8$ or —(CHR$^{19}$)—(CH$_2$)—(CH$_2$)—C(=O)—O—R$^8$;

—(CHR$^{20}$)—NH—C(=O)—O—R$^9$, —(CHR$^{20}$)—(CH$^2$)—NH—C(=O)—O—R$^9$, —(CHR$^{20}$)—NH—C(=O)—(CH$_2$)—NH—C(=O)—O—R$^9$, —(CHR$^{20}$)—(CH$_2$)—(CH$_2$)—NH—C(=O)—O—R$^9$, —(CHR$^{20}$)—(CH$_2$)—(CH$_2$)—(CH$_2$)—NH—C(=O)—O—R$^9$, —(CHR$^{20}$)—(CH$_2$)—(CH$_2$)—NH—C(=O)—O—R$^9$ or —(CHR$^{20}$)—(CH$_2$)—(CH$_2$)—(CH$_2$)—(CH$_2$)—NH—C(=O)—O—R$^9$ —(CR$^{21}$R$^{22}$)—R$^{23}$, —(CR$^{21}$R$^{22}$)—(CH$_2$)—R$^{23}$, —(CR$^{21}$R$^{22}$)—O—R$^{23}$, —(CR$^{21}$R$^{22}$)—S—R$^{23}$, —(CR$^{21}$R$^{22}$)—NH—R$^{23}$, —(CR$^{21}$R$^{22}$)—(CH$_2$)—(CH$_2$)—R$^{23}$, —(CR$^{21}$R$^{22}$)—O—(CH$_2$)—R$^{23}$, —(CR$^{21}$R$^{22}$)—S—(CH$_2$)—R$^{23}$, —(CR$^{21}$R$^{22}$)—NH—(CH$_2$)—R$^{23}$, —(CR$^{21}$R$^{22}$)—(CH$_2$)—(CH$_2$)—O—R$^{23}$, —(CR$^{21}$R$^{22}$)—(CH$_2$)—(CH$_2$)—NH—R$^{23}$, —(CR$^{21}$R$^{22}$)—(CH$_2$)—(CH$_2$)—S—R$^{23}$ or —(CR$^{21}$R$^{22}$)—(CH$_2$)—(CH$_2$)—(CH$_2$)—R$^{23}$; or

—CH=CH—R$^{24}$;

R$^6$ represents —NR$^{10}$R$^{11}$;

a member selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, 2-hexyl, 3-hexyl, —(CH$_2$)—(CH$_2$)—(C(CH$_3$)$_3$), n-heptyl, 3-heptyl, 4-heptyl, n-octyl, —(CH$_2$)—(CH$_2$)—(CH)(CH$_3$)—(CH$_2$)—(CH$_2$)—(CH$_2$)—(CH$_3$), vinyl, 1-propenyl, 2-propenyl, 1-butenyl, 2-butenyl, 3-butenyl, —CH=CH—CH=CH—CH$_3$, —CH$_2$—O—CH$_3$, —CH$_2$—O—CH$_2$—CH$_2$—O—CH$_3$, —CH$_2$—S—CH$_3$,—CH$_2$—S—CH$_2$—CH$_2$—S—CH$_3$, —CH$_2$—NH—CH$_3$ and —CH$_2$—NH—CH$_2$—CH$_3$;

a member selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, (1,2,3,4)-tetrahydronaphthyl, (1,3)-dihydroisoindolyl, (2,3)-dihydroindolyl, 3,4-dihydro-2H-benzo[1,4]oxazinyl and bicyclo[2.2.1]heptyl, wherein the (hetero)cycloaliphatic group may be substituted with 1, 2, 3, 4 or 5 substituents selected, identically or differently, in each case, from the group consisting of oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, C$_{1-5}$-alkyl, —C(=O)—H, —C(=O)—C$_{1-5}$-alkyl, —C(=O)—C$_{1-5}$-perfluoroalkyl, —C(=O)—OH, —C(=O)—O—C$_{1-5}$-alkyl, —(CH$_2$)—C(=O)—OH, —(CH$_2$)—C(=O)—O—C$_{1-5}$-alkyl, —NH—C$_{1-5}$-alkyl, —N(C$_{1-5}$-alkyl)$_2$, —O-phenyl, —O-benzyl, phenyl and benzyl, and wherein in each case the cyclic moiety of the groups —O-phenyl, —O-benzyl, phenyl and benzyl may be substituted with 1, 2, 3, 4 or 5 substituents selected, identically or differently, in each case, from the group consisting of F, Cl, Br, —OH, —CF$_3$, —SF$_5$, —CN, —NO$_2$, —O—C$_{1-5}$-alkyl, —C$_{1-5}$ alkyl, —O—CF$_3$, —S—CF$_3$, phenyl and —O-benzyl;

a member selected from the group consisting of phenyl, naphthyl, thiophenyl, furanyl, pyrrolyl, pyrazolyl, pyrazinyl, triazolyl, pyridinyl, imidazolyl, indolyl, isoindolyl, benzo[b]furanyl, benzo[b]thiophenyl, thiazolyl, thiadiazolyl, oxazolyl, isoxazolyl, pyridazinyl, pyrazinyl, pyrimidinyl, indazolyl, quinazolinyl, quinolinyl, isoquinolinyl, phenazinyl, phenothiazinyl, oxadiazolyl, benzo[1,2,5]oxadiazolyl, (3,4)-dihydro-2H-benzo[1,4]oxazinyl, (2,3)-dihydro-benzo[1,4]dioxinyl, benzo[1,3]dioxinyl, (2,3)-dihydrobenzofuranyl, 2H-chromenyl, chromanyl and (1,2,3,4)-tetrahydroisoquinolinyl, wherein the member may in each case be substituted with 1, 2, 3, 4 or 5 substituents selected, identically or differently, in each case, from the group consisting of F, Cl, Br, I, —CN, —CF$_3$, —SF$_5$, —OH, —O—C$_{1-5}$-alkyl, —O—C$_{2-5}$-alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$-alkyl, —C$_{1-5}$ alkyl, —C(=O)—OH, —C(=O)—O—C$_{1-5}$-alkyl, —O—C(=O)—C$_{1-5}$-alkyl, —O—C(=O)-phenyl, —(CH$_2$)—O—C(=O)—C$_{1-5}$-alkyl, —(CH$_2$)—O—C(=O)-phenyl, —NH—C$_{1-5}$-alkyl, —N(C$_{1-5}$-alkyl)$_2$, —NH—C(=O)—O—C$_{1-5}$-alkyl, —NH—C(=O)—C$_{1-5}$-alkyl, —C(=O)—H, —C(=O)—C$_{1-5}$-alkyl, —C(=O)—C$_{1-5}$-perfluoroalkyl, —C(=O)—NH$_2$, —C(=O)—NH—C$_{1-5}$-alkyl, —C(=O)—N—(C$_{1-5}$-alkyl)$_2$, —S(=O)$_2$—NH$_2$, —S(=O)$_2$—NH—C$_{1-5}$-alkyl, —S(=O)$_2$—NH-phenyl, —S(=O)$_2$—C$_{1-5}$-alkyl, —S(=O)$_2$-phenyl, —O-phenyl, —S-phenyl, —S-benzyl, —O-benzyl, phenyl and benzyl, and wherein in each case the cyclic moiety of the groups —O—C(=O)-phenyl, —(CH$_2$)—O—C(=O)-phenyl, —S(=O)$_2$—NH-phenyl, —S(=O)$_2$-phenyl, —O-phenyl, —S-phenyl, —S-benzyl, —O-benzyl, phenyl and benzyl may be substituted with 1, 2, 3, 4 or 5 substituents selected, identically or differently, in each case, from the group consisting of F, Cl, Br, —OH, —CF$_3$, —SF$_5$, —CN, —NO$_2$, —O—C$_{1-5}$-alkyl, —C$_{1-5}$ alkyl, —O—CF$_3$, —S—CF$_3$, phenyl and —O-benzyl; —(CHR$^{25}$)—R$^{26}$, —(CHR$^{25}$)—(CH$_2$)—R$^{26}$, —(CHR$^{25}$)—O—R$^{26}$, —(CHR$^{25}$)—S—R$^{26}$, —(CHR$^{25}$)—NH—R$^{26}$, —(CHR$^{25}$)—(CH$_2$)—(CH$_2$)—R$^{26}$, —(CHR$^{25}$)—O—(CH$_2$)—R$^{26}$, —(CHR$^{25}$)—S—(CH$_2$)—R$^{26}$, —(CHR$^{25}$)—NH—(CH$_2$)—R$^{26}$, —(CHR$^{25}$)—(CH$_2$)—O—R$^{26}$, —(CHR$^{25}$)—(CH$_2$)—(CH$_2$)—NH—R$^{26}$ or —(CHR$^{252}$)—(CH$_2$)—(CH$_2$)—S—R$^{26}$;

or —(CHR$^{27}$)—R$^{28}$, —(CHR$^{27}$)—(CH$_2$)—R$^{28}$ or —(CHR$^{27}$)—(CH$_2$)—(CH$_2$)—R$^{28}$;

R$^7$ represents a member selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, 2-hexyl, 3-hexyl, —(CH$_2$)—(CH$_2$)—(C(CH$_3$)$_3$), n-heptyl, 3-heptyl, 4-heptyl, n-octyl and —(CH$_2$)—(CH$_2$)—(CH)(CH$_3$)—(CH$_2$)—(CH$_2$)—(CH$_2$)—(CH$_3$);

a member selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, (1,2,3,4)-tetrahydronaphthyl, (1,3)-dihydroisoindolyl, (2,3)-dihydroindolyl and 3,4-dihydro-2H-benzo[1,4]oxazinyl, wherein the (hetero)cycloaliphatic group may in each case be substituted with 1, 2, 3, 4 or 5 substituents selected, identically or differently, in each case, from the group consisting of oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$ alkyl, —C(=O)—H, —C(=O)—C$_{1-5}$-alkyl, —C(=O)—C$_{1-5}$-perfluoroalkyl, —C(=O)—OH, —C(=O)—O—C$_{1-5}$-alkyl, —(CH$_2$)—C(=O)—OH, —(CH$_2$)—C(=O)—O—C$_{1-5}$-alkyl, —NH—C$_{1-5}$-alkyl, —N(C$_{1-5}$-alkyl)$_2$, —O-phenyl, —O-benzyl, phenyl and benzyl, and wherein in each case the cyclic moiety of the groups —O-phenyl, —O-benzyl, phenyl and benzyl may be substituted with 1, 2, 3, 4 or 5 substituents selected, identically or differently, in each case, from the group consisting of F, Cl, Br, —OH, —CF$_3$, —SF$_5$, —CN, —NO$_2$, —O—C$_{1-5}$-alkyl, —C$_{1-5}$ alkyl, —O—CF$_3$, —S—CF$_3$, phenyl and —O-benzyl;

a member selected from the group consisting of phenyl, naphthyl, thiophenyl, furanyl, pyrrolyl, pyrazolyl, pyrazinyl, triazolyl, pyridinyl, imidazolyl, indolyl, isoindolyl, benzo[b]furanyl, benzo[b]thiophenyl, thiazolyl, thiadiazolyl, oxazolyl, isoxazolyl, pyridazinyl, pyrazinyl, pyrimidinyl, indazolyl, quinazolinyl, quinolinyl, isoquinolinyl, phenazinyl, phenothiazinyl and oxadiazolyl, wherein the member may be substituted with 1, 2, 3, 4 or 5 substituents selected, identically or differently, in each case, from the group consisting of F, Cl, Br, I, —CN, —CF$_3$, —SF$_5$, —OH, —O—C$_{1-5}$-alkyl, —O—C$_{2-5}$-alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$-alkyl, —C$_{1-5}$ alkyl, —C(=O)—OH, —C(=O)—O—C$_{1-5}$-alkyl, —O—C(=O)—C$_{1-5}$-alkyl, —O—C(=O)-phenyl, —(CH$_2$)—O—C(=O)—C$_{1-5}$-alkyl, —(CH$_2$)—O—C(=O)-phenyl, —NH—C$_{1-5}$-alkyl, —N(C$_{1-5}$-alkyl)$_2$, —NH—C(=O)—O—C$_{1-5}$-alkyl, —NH—C(=O)—C$_{1-5}$-alkyl, —C(=O)—H, —C(=O)—C$_{1-5}$-alkyl, —C(=O)—C$_{1-5}$-perfluoroalkyl, —C(=O)—NH$_2$, —C(=O)—NH—C$_{1-5}$-alkyl, —C(=O)—N—(C$_{1-5}$-alkyl)$_2$, —O-phenyl, —S-phenyl, —S-benzyl, —O-benzyl, phenyl and benzyl, and wherein in each case the cyclic moiety of the groups —O—C(=O)-phenyl, —(CH$_2$)—O—C(=O)-phenyl, —O-phenyl, —S-phenyl, —S-benzyl, —O-benzyl, phenyl and benzyl may be substituted with 1, 2, 3, 4 or 5 substituents selected, identically or differently, in each case, from the group consisting of F, Cl, Br, —OH, —CF$_3$, —SF$_5$, —CN, —NO$_2$, —O—C$_{1-5}$-alkyl, —C$_{1-5}$ alkyl, —O—CF$_3$, —S—CF$_3$, phenyl and —O-benzyl; or or an —NR$^{7a}$R$^{7b}$ group, in which R$^{7a}$ and R$^{7b}$, represent a member selected, identically or differently, in each case, from the group consisting of methyl, ethyl, n-propyl, isopropyl, n-butyl, sec-butyl, isobutyl, tert-butyl and n-pentyl;

R$^8$ represents a member selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, 2-hexyl, 3-hexyl, —(CH$_2$)—(CH$_2$)—(C(CH$_3$)$_3$), n-heptyl, 3-heptyl, 4-heptyl, n-octyl and —(CH$_2$)—(CH$_2$)—(CH)(CH$_3$)—(CH$_2$)—(CH$_2$)—(CH$_2$)—(CH$_3$); or a member selected from the group consisting of phenyl, naphthyl, thiophenyl, furanyl, pyrrolyl, pyrazolyl, pyrazinyl, triazolyl, pyridinyl, imidazolyl, indolyl, isoindolyl, benzo[b]furanyl, benzo[b]thiophenyl, thiazolyl, thiadiazolyl, oxazolyl, isoxazolyl, pyridazinyl, pyrazinyl, pyrimidinyl, indazolyl, quinazolinyl, quinolinyl, isoquinolinyl, phenazinyl, phenothiazinyl and oxadiazolyl, wherein the member may be substituted with 1, 2, 3, 4 or 5 substituents selected, identically or differently, in each case, from the group consisting of F, Cl, Br, I, —CN, —CF$_3$, —SF$_5$, —OH, —O—C$_{1-5}$-alkyl, —O—C$_{2-5}$-alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$-alkyl, —C$_{1-5}$ alkyl, —C(=O)—OH, —C(=O)—O—C$_{1-5}$-alkyl, —O—C(=O)—C$_{1-5}$-alkyl, —O—C(=O)-phenyl, —(CH$_2$)—O—C(=O)—C$_{1-5}$-alkyl, —NH—C$_{1-5}$-alkyl, —N(C$_{1-5}$-alkyl)$_2$, —NH—C(=O)—O—C$_{1-5}$-alkyl, —NH—C(=O)—C$_{1-5}$-alkyl, —C(=O)—H, —C(=O)—C$_{1-5}$-alkyl, —C(=O)—C$_{1-5}$-perfluoroalkyl, —C(=O)—NH$_2$, —C(=O)—NH—C$_{1-5}$-alkyl, —C(=O)—N—(C$_{1-5}$-alkyl)$_2$, —S(=O)$_2$—NH$_2$ and —S(=O)$_2$—NH—C$_{1-5}$-alkyl or attached via a —(CH$_2$), —(CH$_2$)$_2$ or —(CH$_2$)$_3$ group;

R$^9$ represents a member selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, 2-hexyl, 3-hexyl, —(CH$_2$)—(CH$_2$)—(C(CH$_3$)$_3$), n-heptyl, 3-heptyl, 4-heptyl, n-octyl and —(CH$_2$)—(CH$_2$)—(CH)(CH$_3$)—(CH$_2$)—(CH$_2$)—(CH$_2$)—(CH$_3$);

a member selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, (1,2,3,4)-tetrahydronaphthyl, (1,3)-dihydroisoindolyl, (2,3)-dihydroindolyl, 3,4-dihydro-2H-benzo[1,4]oxazinyl and 9H-fluorenyl, wherein the (hetero)cycloaliphatic group may be substituted with 1, 2, 3, 4 or 5 substituents selected, identically or differently, in each case, from the group consisting of oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$ alkyl, —C(=O)—H, —C(=O)—C$_{1-5}$-alkyl, —C(=O)—C$_{1-5}$-perfluoroalkyl, —C(=O)—OH, —C(=O)—O—C$_{1-5}$-alkyl, —(CH$_2$)—C(=O)—OH, —(CH$_2$)—C(=O)—O—C$_{1-5}$-alkyl, —NH—C$_{1-5}$-alkyl, —N(C$_{1-5}$-alkyl)$_2$, —O-phenyl, —O-benzyl, phenyl and benzyl, and wherein in each case the cyclic moiety of the groups —O-phenyl, —O-benzyl, phenyl and benzyl may be substituted with 1, 2, 3, 4 or 5 substituents selected, identically or differently, in each case, from the group consisting of F, Cl, Br, —OH, —CF$_3$, —SF$_5$, —CN, —NO$_2$, —O—C$_{1-5}$-alkyl, —C$_{1-5}$ alkyl, —O—CF$_3$, —S—CF$_3$, phenyl and —O-benzyl or is attached via a —(CH$_2$), —(CH$_2$)$_2$ or —(CH$_2$)$_3$ group; or a member selected from the group consisting of phenyl, naphthyl, thiophenyl, furanyl, pyrrolyl, pyrazolyl, pyrazinyl, triazolyl, pyridinyl, imidazolyl, indolyl, isoindolyl, benzo[b]furanyl, benzo[b]thiophenyl, thiazolyl, thiadiazolyl, oxazolyl, isoxazolyl, pyridazinyl, pyrazinyl, pyrimidinyl, indazolyl, quinazolinyl, quinolinyl, isoquinolinyl, phenazinyl, phenothiazinyl and oxadiazolyl, wherein the member may be substituted with 1, 2, 3, 4 or 5 substituents selected, identically or differently, in each case, from the group consisting of F, Cl, Br, I, —CN, —CF$_3$, —SF$_5$, —OH, —O—C$_{1-5}$-alkyl, —O—C$_{2-5}$-alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$-alkyl, —C$_{1-5}$ alkyl, —C(=O)—OH, —C(=O)—O—C$_{1-5}$-alkyl, —O—C(=O)—C$_{1-5}$-alkyl, —O—C(=O)-phenyl, —(CH$_2$)—O—C(=O)—C$_{1-5}$-alkyl, —NH—C$_{1-5}$-alkyl, —N(C$_{1-5}$-alkyl)$_2$, —NH—C(=O)—O—C$_{1-5}$-alkyl, —NH—C(=O)—C$_{1-5}$-alkyl, —C(=O)—H, —C(=O)—C$_{1-5}$-alkyl, —C(=O)—C$_{1-5}$-perfluoroalkyl, —C(=O)—NH$_2$, —C(=O)—NH—C$_{1-5}$-alkyl, —C(=O)—N—(C$_{1-5}$-alkyl)$_2$, —S(=O)$_2$—NH$_2$ and —S(=O)$_2$—NH—C$_{1-5}$-alkyl or is attached via a —(CH$_2$), —(CH$_2$)$_2$ or —(CH$_2$)$_3$ group;

R$^{10}$ and R$^{11}$, identically or differently, in each case, represents a member selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, 2-hexyl, 3-hexyl, —(CH$_2$)—(CH$_2$)—(C(CH$_3$)$_3$), n-heptyl, 3-heptyl, 4-heptyl, n-octyl and —(CH$_2$)—(CH$_2$)—(CH)(CH$_3$)—(CH$_2$)—(CH$_2$)—(CH$_2$)—(CH$_3$);

R$^{12}$, R$^{14}$, R$^{16}$, R$^{18}$, R$^{21}$, R$^{22}$, R$^{25}$ and R$^{27}$, identically or differently, in each case, represents hydrogen; or a member selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, 2-hexyl, 3-hexyl, —(CH$_2$)—(CH$_2$)—(C(CH$_3$)$_3$), n-heptyl, 3-heptyl, 4-heptyl, n-octyl and —(CH$_2$)—(CH$_2$)—(CH)(CH$_3$)—(CH$_2$)—(CH$_2$)—(CH$_2$)—(CH$_3$);

R$^{13}$ represents a (hetero)cycloaliphatic member selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl and dithiolanyl, wherein the (hetero)cycloaliphatic member may be substituted with 1, 2, 3, 4 or 5 substituents selected, identically or differently, in each case, from the group consisting of oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, C$_{1-5}$-alkyl, —C(=O)—H, —C(=O)—C$_{1-5}$-alkyl, —C(=O)—C$_{1-5}$-perfluoroalkyl, —C(=O)—OH, —C(=O)—O—C$_{1-5}$-alkyl, —(CH$_2$)—C(=O)—OH, —(CH$_2$)—C(=O)—O—C$_{1-5}$-alkyl, —NH—C$_{1-5}$-alkyl, —N(C$_{1-5}$-alkyl)$_2$, —O-phenyl, —O-benzyl, phenyl and benzyl, and wherein in each case the cyclic moiety of the groups —O-phenyl, —O-benzyl, phenyl and benzyl may be substituted with 1, 2, 3, 4 or 5 substituents selected, identically or differently, in each case, from the group consisting of F, Cl, Br, —OH, —CF$_3$, —SF$_5$, —CN, —NO$_2$, —O—C$_{1-5}$-alkyl, —C$_{1-5}$ alkyl, —O—CF$_3$, —S—CF$_3$, phenyl and —O-benzyl;

R$^{15}$ and R$^{17}$, identically or differently, in each case, represent a member selected from the group consisting of phenyl, naphthyl, thiophenyl, furanyl, pyrrolyl, pyrazolyl, pyrazinyl, triazolyl, pyridinyl, imidazolyl, indolyl, isoindolyl, benzo[b]furanyl, benzo[b]thiophenyl, thiazolyl, thiadiazolyl, oxazolyl, isoxazolyl, pyridazinyl, pyrazinyl, pyrimidinyl, indazolyl, quinazolinyl, quinolinyl, isoquinolinyl, phenazinyl, phenothiazinyl and oxadiazolyl, wherein the member may be substituted with 1, 2, 3, 4 or 5 substituents selected, identically or differently, in each case, from the group consisting of F, Cl, Br, I, —CN, —CF$_3$, —SF$_5$, —OH, —O—C$_{1-5}$-alkyl, —O—C$_{2-5}$-alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$-alkyl, —C$_{1-5}$ alkyl, —C(=O)—OH, —C(=O)—O—C$_{1-5}$-alkyl, —O—C(=O)—C$_{1-5}$-alkyl, —(CH$_2$)—O—C(=O)—C$_{1-5}$-alkyl, —NH—C$_{1-5}$-alkyl, —N(C$_{1-5}$-alkyl)$_2$, —NH—C(=O)—O—C$_{1-5}$-alkyl, —NH—C(=O)—C$_{1-5}$-alkyl, —C(=O)—H, —C(=O)—C$_{1-5}$-alkyl, —C(=O)—C$_{1-5}$-perfluoroalkyl, —C(=O)—NH$_2$, —C(=O)—NH—C$_{1-5}$-alkyl, —C(=O)—N—(C$_{1-5}$-alkyl)$_2$, —S(=O)$_2$—NH$_2$, —S(=O)$_2$—NH—C$_{1-5}$-alkyl, —S(=O)$_2$—C$_{1-5}$-alkyl, —O-phenyl, —O-benzyl, phenyl and benzyl, and wherein the cyclic moiety of the groups —O-phenyl, —O-benzyl, phenyl and benzyl may be substituted with 1, 2, 3, 4 or 5 substituents selected, identically or differently, in each case, from the group consisting of F, Cl, Br, —OH, —CF$_3$, —SF$_5$, —CN, —NO$_2$, —O—C$_{1-5}$-alkyl, —C$_{1-5}$ alkyl, —O—CF$_3$ and —S—CF$_3$;

R$^{19}$ represents hydrogen;

a member selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, 2-hexyl, 3-hexyl, —(CH$_2$)—(CH$_2$)—(C(CH$_3$)$_3$), n-heptyl, 3-heptyl, 4-heptyl, n-octyl and —(CH$_2$)—(CH$_2$)—(CH)(CH$_3$)—(CH$_2$)—(CH$_2$)—(CH$_2$)—(CH$_3$); or a phenyl group;

R$^{20}$ represents hydrogen;

a member selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, 2-hexyl, 3-hexyl, —(CH$_2$)—(CH$_2$)—(C(CH$_3$)$_3$), n-heptyl, 3-heptyl, 4-heptyl, n-octyl and —(CH$_2$)—(CH$_2$)—(CH)(CH$_3$)—(CH$_2$)—(CH$_2$)—(CH$_2$)—(CH$_3$); or a phenyl group, which may be attached via a —(CH$_2$) or —(CH$_2$)$_2$ group;

R$^{23}$ represents a member selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, (1,2,3,4)-tetrahydronaphthyl, (1,3)-dihydroisoindolyl, (2,3)-dihydroindolyl and 3,4-dihydro-2H-benzo[1,4]oxazinyl, wherein the (hetero)cycloaliphatic group may be substituted with 1, 2, 3, 4 or 5 substituents selected, identically or differently, in each case, from the group consisting of oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$ alkyl, —C(=O)—H, —C(=O)—C$_{1-5}$-alkyl, —C(=O)—C$_{1-5}$-perfluoroalkyl, —C(=O)—OH, —C(=O)—O—C$_{1-5}$-alkyl, —(CH$_2$)—C(=O)—OH, —(CH$_2$)—C(=O)—O—C$_{1-5}$-alkyl, —NH—C$_{1-5}$-alkyl, —N(C$_{1-5}$-alkyl)$_2$, —O-phenyl, —O-benzyl, phenyl and benzyl, and wherein the cyclic moiety of the groups —O-phenyl, —O-benzyl, phenyl and benzyl may be substituted with 1, 2, 3, 4 or 5 substituents selected, identically or differently, in each case, from the group consisting of F, Cl, Br, —OH, —CF$_3$, —SF$_5$, —CN, —NO$_2$, —O—C$_{1-5}$-alkyl, —C$_{1-5}$ alkyl, —O—CF$_3$, —S—CF$_3$, phenyl and —O-benzyl;

a member selected from the group consisting of phenyl, naphthyl, thiophenyl, furanyl, pyrrolyl, pyrazolyl, pyrazinyl, triazolyl, pyridinyl, imidazolyl, indolyl, isoindolyl, benzo[b]furanyl, benzo[b]thiophenyl, thiazolyl, thiadiazolyl, oxazolyl, isoxazolyl, pyridazinyl, pyrazinyl, pyrimidinyl, indazolyl, quinazolinyl, quinolinyl, isoquinolinyl, phenazinyl, phenothiazinyl, oxadiazolyl, benzo[1,2,5]oxadiazolyl, (3,4)-dihydro-2H-benzo[1,4]oxazinyl, (2,3)-dihydro-benzo[1,4]dioxinyl, benzo[1,3]dioxinyl, (2,3)-dihydrobenzofuranyl, 2H-chromenyl, chromanyl and (1,2,3,4)-tetrahydroisoquinolinyl, wherein the member may in each case be substituted with 1, 2, 3, 4 or 5 substituents selected, identically or differently, in each case, from the group consisting of F, Cl, Br, I, —CN, —CF$_3$, —SF$_5$, —OH, —O—C$_{1-5}$-alkyl, —O—C$_{2-5}$-alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$-alkyl, —C$_{1-5}$ alkyl, —C(=O)—OH, —C(=O)—O—C$_{1-5}$-alkyl, —O—C(=O)—C$_{1-5}$-alkyl, —O—C(=O)-phenyl, —(CH$_2$)—O—C(=O)—C$_{1-5}$-alkyl, —(CH$_2$)—O—C(=O)-phenyl, —NH—C$_{1-5}$-alkyl, —N(C$_{1-5}$-alkyl)$_2$, —NH—C(=O)—O—C$_{1-5}$-alkyl, —NH—C(=O)—C$_{1-5}$-alkyl, —C(=O)—H, —C(=O)—C$_{1-5}$-alkyl, —C(=O)—C$_{1-5}$-perfluoroalkyl, —C(=O)—NH$_2$, —C(=O)—NH—C$_{1-5}$-alkyl, —C(=O)—N—(C$_{1-5}$-alkyl)$_2$, —S(=O)$_2$—NH$_2$, —S(=O)$_2$—NH—C$_{1-5}$-alkyl, —S(=O)$_2$—NH-phenyl, —S(=O)$_2$—C$_{1-5}$-alkyl, —S(=O)$_2$-phenyl, —O-phenyl, —S-phenyl, —S-benzyl, —O-benzyl, phenyl and benzyl, and wherein, in each case, the cyclic moiety of the groups —O—C(=O)-phenyl, —(CH$_2$)—O—C(=O)-phenyl, —S(=O)$_2$—NH-phenyl, —S(=O)$_2$-phenyl, —O-phenyl, —S-phenyl, —S-benzyl, —O-benzyl, phenyl and benzyl may be substituted with 1, 2, 3, 4 or 5 substituents selected, identically or differently, in each case, from the group consisting of F, Cl, Br, —OH, —CF$_3$, —SF$_5$, —CN, —NO$_2$, —O—C$_{1-5}$-alkyl, —C$_{1-5}$ alkyl, —O—CF$_3$, —S—CF$_3$, phenyl and —O-benzyl;

R$^{24}$ and R$^{28}$, identically or differently, in each case, represent a member selected from the group consisting of phenyl, naphthyl, thiophenyl, furanyl, pyrrolyl, pyrazolyl, pyrazinyl, triazolyl, pyridinyl, imidazolyl, indolyl, isoindolyl, benzo[b]furanyl, benzo[b]thiophenyl, thiazolyl, thiadiazolyl, oxazolyl, isoxazolyl, pyridazinyl, pyrazinyl, pyrimidinyl, indazolyl, quinazolinyl, quinolinyl, isoquinolinyl, phenazinyl, phenothiazinyl, oxadiazolyl, benzo[1,2,5]oxadiazolyl, (3,4)-dihydro-2H-benzo[1,4]oxazinyl, (2,3)-dihydro-benzo[1,4]dioxinyl, benzo[1,3]dioxinyl, (2,3)-dihydrobenzofuranyl, 2H-chromenyl, chromanyl and (1,2,3,4)-tetrahydroisoquinolinyl, wherein the member may in each case be substituted with 1, 2, 3, 4 or 5 substituents selected, identically or differently, in each case, from the group consisting of F, Cl, Br, I, —CN, —CF$_3$, —SF$_5$, —OH, —O—C$_{1-5}$-alkyl, —O—C$_{2-5}$-alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$-alkyl, C$_{1-5}$-alkyl, —C(=O)—OH, —C(=O)—O—C$_{1-5}$-alkyl, —O—C(=O)—C$_{1-5}$-alkyl, —O—C(=O)-phenyl, —(CH$_2$)—O—C(=O)—C$_{1-5}$-alkyl, —(CH$_2$)—O—C(=O)-phenyl, —NH—C$_{1-5}$-alkyl, —N(C$_{1-5}$-alkyl)$_2$, —NH—C(=O)—O—C$_{1-5}$-alkyl, —NH—C(=O)—C$_{1-5}$-alkyl, —C(=O)—H, —C(=O)—C$_{1-5}$-alkyl, —C(=O)—C$_{1-5}$-perfluoroalkyl, —C(=O)—NH$_2$, —C(=O)—NH—C$_{1-5}$-alkyl, —C(=O)—N—(C$_{1-5}$-alkyl)$_2$, —S(=O)$_2$—NH$_2$, —S(=O)$_2$—NH—C$_{1-5}$-alkyl, —S(=O)$_2$—NH-phenyl, —S(=O)$_2$—C$_{1-5}$-alkyl, —S(=O)$_2$-phenyl, —O-phenyl, —S-phenyl, —S-benzyl, —O-benzyl, phenyl and benzyl, and wherein the cyclic moiety of the groups —O—C(=O)-phenyl, —(CH$_2$)—O—C(=O)-phenyl, —S(=O)$_2$—NH-phenyl, —S(=O)$_2$-phenyl, —O-phenyl, —S-phenyl, —S-benzyl, —O-benzyl, phenyl and benzyl may be substituted with 1, 2, 3, 4 or 5 substituents selected, identically or differently, in each case, from the group consisting of F, Cl, Br, —OH, —CF$_3$, —SF$_5$, —CN, —NO$_2$, —O—C$_{1-5}$-alkyl, —C$_{1-5}$ alkyl, —O—CF$_3$, —S—CF$_3$, phenyl and —O-benzyl; and R$^{26}$ represents a member selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, (1,2,3,4)-tetrahydronaphthyl, (1,3)-dihydroisoindolyl, (2,3)-dihydroindolyl, 3,4-dihydro-2H-benzo[1,4]oxazinyl and bicyclo[2.2.1]heptyl, wherein the (hetero)cycloaliphatic group may in each case be substituted with 1, 2, 3, 4 or 5 substituents selected, identically or differently, in each case, from the group consisting of oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$ alkyl, —C(=O)—H, —C(=O)—C$_{1-5}$-alkyl, —C(=O)—C$_{1-5}$-perfluoroalkyl, —C(=O)—OH, —C(=O)—O—C$_{1-5}$-alkyl, —(CH$_2$)—C(=O)—OH, —(CH$_2$)—C(=O)—O—C$_{1-5}$-alkyl, —NH—C$_{1-5}$-alkyl, —N(C$_{1-5}$-alkyl)$_2$, —O-phenyl, —O-benzyl, phenyl and benzyl, wherein the cyclic moiety of the groups —O-phenyl, —O-benzyl, phenyl and benzyl may be substituted with 1, 2, 3, 4 or 5 substituents selected, identically or differently, in each case, from the group consisting of F, Cl, Br, —OH, —CF$_3$, —SF$_5$, —CN, —NO$_2$, —O—C$_{1-5}$-alkyl, —C$_{1-5}$ alkyl, —O—CF$_3$, —S—CF$_3$, phenyl and —O-benzyl.

24. A compound according to claim 22 wherein

R$^3$ represents a member selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, 2-hexyl, 3-hexyl and n-heptyl;

a (hetero)cycloaliphatic member selected from the group consisting of cyclopentyl, cyclohexyl, cycloheptyl, tetrahydrofuranyl, pyrrolidinyl, piperidinyl, morpholinyl, piperazinyl, azepanyl and diazepanyl;

a member selected from the group consisting of phenyl, naphthyl, thiophenyl, furanyl, pyrrolyl, pyrazolyl, pyrazinyl, triazolyl, pyridinyl, imidazolyl, indolyl, isoindolyl, benzo[b]furanyl, benzo[b]thiophenyl, thiazolyl, thiadiazolyl, oxazolyl, isoxazolyl, pyridazinyl, pyrazinyl, pyrimidinyl, indazolyl, quinazolinyl, quinolinyl, isoquinolinyl, phenazinyl, phenothiazinyl and oxadiazolyl, wherein the member may be substituted with 1, 2, 3, 4 or 5 substituents selected, identically or differently, in each case, from the group consisting of F, Cl, Br, I, —CN, —CF$_3$, methoxy, ethoxy, n-propoxy, isopropoxy, n-butoxy, isobutoxy, tert-butoxy, methyl, ethyl, n-propyl, iso-propyl, n-butyl, isobutyl, sec-butyl, tert-butyl and n-pentyl;

—CHR$^{12}$)—R$^{13}$, —(CHR$^{12}$)—(CH$_2$)—R$^{13}$ or —(CHR$^{12}$)—(CH$_2$)—(CH$_2$)—R$^{13}$; or

—(CHR$^{14}$)—R$^{15}$, —(CHR$^{14}$)—(CH$_2$)—R$^{15}$ or —(CHR$^{14}$)—(CH$_2$)—(CH$_2$)—R$^{15}$;

R$^4$ represents —(CHR$^{16}$)—R$^{17}$ or —(CHR$^{16}$)—(CH$_2$)—R$^{17}$;

R$^5$ represents a member selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, 2-hexyl, 3-hexyl, —(CH$_2$)—(CH$_2$)—(C(CH$_3$)$_3$), n-heptyl, 3-heptyl, 4-heptyl, n-octyl, —(CH$_2$)—(CH$_2$)—(CH)(CH$_3$)—(CH$_2$)—(CH$_2$)—(CH$_2$)—(CH$_3$), vinyl, 1-propenyl, 2-propenyl, 1-butenyl, 2-butenyl, 3-butenyl, —CH=CH—CH=CH—CH$_3$, —CH$_2$—O—CH$_3$ and —CH$_2$—O—CH$_2$—CH$_2$—O—CH$_3$;

a member selected from the group consisting of cyclopropyl, cyclobutyl, cyclopentyl, cyclohexyl, cycloheptyl, tetrahydrofuranyl, piperidinyl, piperazinyl and (1,2,3,4)-tetrahydronaphthyl, wherein the (hetero)cycloaliphatic member may in each case be substituted with 1, 2, 3, 4 or 5 substituents selected, identically or differently, in each case, from the group consisting of —C(=O)—O—CH$_3$, —C(=O)—O—C$_2$H$_5$, —C(=O)—C(CH$_3$)$_3$ and phenyl, wherein in each case the cyclic moiety of the phenyl group may be substituted with 1, 2, 3, 4 or 5 substituents selected, identically or differently, in each case, from the group consisting of F, Cl and Br;

a member selected from the group consisting of phenyl, naphthyl, thiophenyl, furanyl, pyrrolyl, pyrazolyl, pyrazinyl, triazolyl, pyridinyl, indolyl, benzo[b]thiophenyl, thiazolyl, thiadiazolyl, oxazolyl, isoxazolyl, quinolinyl, isoquinolinyl, benzo[1,3]dioxinyl, (2,3)-dihydrobenzofuranyl, benzo[1,2,5]oxadiazolyl, 2H-chromenyl and chromanyl, wherein the member may in each case be substituted with 1, 2, 3, 4 or 5 substituents selected, identically or differently, in each case, from the group consisting of F, Cl, Br, —CN, —CF$_3$, methoxy, ethoxy, n-propoxy, isopropoxy, n-butoxy, isobutoxy, tert-butoxy, —NO$_2$, —O—CF$_3$, —O—CHF$_2$, —O—CH$_2$F, —S—CF$_3$, —S—CHF$_2$, —S—CH$_2$F, —S—CH$_3$, —S—C$_2$H$_5$, —S—N—C$_3$H$_7$, —S—C(CH$_3$)$_3$, methyl, ethyl, n-propyl, iso-propyl, n-butyl, iso-butyl, sec-butyl, tert-butyl, n-pentyl, —O—C(=O)-phenyl, —(CH$_2$)—O—C(=O)-phenyl, —N(CH$_3$)$_2$, —N(C$_2$H$_5$)$_2$, —S(=O)$_2$-phenyl, —O-phenyl, phenyl, furanyl, thienyl, pyrazolyl, thiadiazolyl and benzyl, wherein in each case the cyclic moiety of the groups —O—C(=O)-phenyl, —(CH$_2$)—O—C(=O)-phenyl, furanyl, thienyl, pyrazolyl, thiadiazolyl, —S(=O)$_2$-phenyl, —O-phenyl, phenyl and benzyl may be substituted with 1, 2, 3, 4 or 5 substituents selected, identically or differently, in each case, from the group consisting of F, Cl and Br;
—C(=O)—R$^7$, —(CHR$^{18}$)—C(=O)—R$^7$, —(CHR$^{18}$)—(CH$_2$)—C(=O)—R$^7$ or —(CHR$^{18}$)—(CH$_2$)—(CH$_2$)—C(=O)—R$^7$;
—C(=O)—O—R$^8$, —(CHR$^{19}$)—C(=O)—O—R$^8$, —(CHR$^{19}$)—(CH$_2$)—C(=O)—O—R$^8$ or —(CHR$^{19}$)—(CH$_2$)—(CH$_2$)—C(=O)—O—R$^8$;
—(CHR$^{20}$)—NH—C(=O)—O—R$^9$, —(CHR$^{20}$)—(CH$_2$)—NH—C(=O)—O—R$^9$, —(CHR$^{20}$)—NH—C(=O)—(CH$_2$)—NH—C(=O)—O—R$^9$, —(CHR$^{20}$)—(CH$_2$)—(CH$_2$)—NH—C(=O)—O—R$^9$, —(CHR$^{20}$)—(CH$_2$)—(CH$_2$)—(CH$_2$)—NH—C(=O)—O—R$^9$, —(CHR$^{20}$)—(CH$_2$)—(CH$_2$)—NH—C(=O)—O—R$^9$ or —(CHR$^{20}$)—(CH$_2$)—(CH$_2$)—(CH$_2$)—(CH$_2$)—NH—C(=O)—O—R$^9$;
—(CR$^{21}$R$^{22}$)—R$^{23}$, —(CR$^{21}$R$^{22}$)—(CH$_2$)—R$^{23}$, —(CR$^{21}$R$^{22}$)—O—R$^{23}$, —(CR$^{21}$R$^{22}$)—S—R$^{23}$, —(CR$^{21}$R$^{22}$)—(CH$_2$)—(CH$_2$)—R$^{23}$, —(CR$^{21}$R$^{22}$)—O—(CH$_2$)—R$^{23}$, —(CR$^{21}$R$^{22}$)—S—(CH$_2$)—R$^{23}$, —(CR$^{21}$R$^{22}$)—(CH$_2$)—(CH$_2$)—O—R$^{23}$, —(CR$^{21}$R$^{22}$)—(CH$_2$)—(CH$_2$)—S—R$^{23}$ or —(CR$^{21}$R$^{22}$)—(CH$_2$)—(CH$_2$)—(CH$_2$)—R$^{23}$, or —CH=CH—R$^{24}$;

R$^6$ represents —NR$^{10}$R$^{11}$;
  a member selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, 2-hexyl and 3-hexyl;
  a member selected from the group consisting of phenyl, naphthyl, thiophenyl, furanyl, pyrazolyl, thiazolyl, (3,4)-dihydro-2H-benzo[1,4]oxazinyl, (2,3)-dihydro-benzo[1,4]dioxinyl and (1,2,3,4)-tetrahydroisoquinolinyl, wherein the member may in each case be substituted with 1, 2, 3, 4 or 5 substituents selected, identically or differently, in each case, from the group consisting of F, Cl, Br, —CN, —CF$_3$, methoxy, ethoxy, n-propoxy, isopropoxy, n-butoxy, isobutoxy, tert-butoxy, —NO$_2$, —O—CF$_3$, —O—CHF$_2$, —O—CH$_2$F, methyl, ethyl, n-propyl, iso-propyl, n-butyl, iso-butyl, sec-butyl, tert-butyl, n-pentyl, —C(CH$_3$)$_2$—CH$_2$—CH$_3$, —C(=O)—O—CH$_3$, —C(=O)—O—C$_2$H$_5$, —C(=O)—O—C(CH$_3$)$_3$, —NH—C(=O)—CH$_3$, —NH—C(=O)—C$_2$H$_5$, —NH—C(=O)—C(CH$_3$)$_3$, —C(=O)—CF$_3$, —C(=O)—C$_2$F$_5$, —S(=O)$_2$—CH$_3$, —S(=O)$_2$—C$_2$H$_5$, —S(=O)—C(CH$_3$)$_3$, phenyl and benzyl;
—(CHR$^{25}$)—R$^{26}$ or —(CHR$^{25}$)—(CH$_2$)—R$^{26}$; or
—(CHR$^{27}$)—R$^{28}$ or —(CHR$^{27}$)—(CH$_2$)—R$^{28}$;

R$^7$ represents a member selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, 2-hexyl and 3-hexyl;
  a (2,3)-dihydroindolyl group;
  a member selected from the group consisting of phenyl, naphthyl and indolyl;
  or an —NR$^{7a}$R$^{7b}$ group, in which R$^{7a}$ and R$^{7b}$, identically or differently, in each case, represent a member selected from the group consisting of methyl, ethyl, n-propyl, isopropyl, n-butyl, sec-butyl, isobutyl, tert-butyl and n-pentyl;
R$^8$ represents a member selected from the group consisting of methyl, ethyl, n-propyl, isopropyl, n-butyl, sec-butyl, isobutyl, tert-butyl, n-pentyl, 2-pentyl, 3-pentyl, neopentyl and n-hexyl; or
  a phenyl group, which may be attached via a —(CH$_2$) group;
R$^9$ represents a member selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, 2-hexyl and 3-hexyl;
  a 9H-fluorenyl group, which may be attached via a —(CH$_2$) group; or
  a phenyl group, which may be attached via a —(CH$_2$) group;
R$^{10}$ and R$^{11}$, identically or differently, in each case, represent a member selected from the group consisting of methyl, ethyl, n-propyl, isopropyl, n-butyl, sec-butyl, isobutyl and tert-butyl;
R$^{12}$, R$^{14}$, R$^{16}$, R$^{18}$, R$^{21}$, R$^{22}$ and R$^{25}$ and R$^{27}$, identically or differently, in each case, represent hydrogen; or
  a member selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, 2-hexyl and 3-hexyl;
R$^{13}$ represents a (hetero)cycloaliphatic member selected from the group consisting of cyclopropyl, cyclobutyl, cyclopentyl, cyclohexyl, cycloheptyl, pyrrolidinyl, piperidinyl, morpholinyl and piperazinyl;
R$^{15}$ and R$^{17}$, mutually independently, in each case represent a phenyl group;
R$^{19}$ represents hydrogen;
  a member selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, 2-hexyl and 3-hexyl; or
  a phenyl group;
R$^{20}$ represents hydrogen;
  a member selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, 2-hexyl and 3-hexyl; or
  a phenyl group, which may be attached via a -(CH$_2$) group;
R$^{23}$ represents a group selected from the group consisting of cyclopropyl, cyclobutyl, cyclopentyl, cyclohexyl, cycloheptyl, pyrrolidinyl, piperidinyl, morpholinyl, piperazinyl, dithiolanyl, isoindole-1,3-dionyl, benzoxazolin-2-onyl and 2,5-dioxo-imidazolidinyl, wherein the member may in each case be substituted with 1, 2 or 3 substituents selected, identically or differently, in each case, from the group consisting of methyl, ethyl, n-propyl, iso-propyl, n-butyl, iso-butyl, sec-butyl, tert-butyl and n-pentyl;
  a member selected from the group consisting of phenyl, naphthyl, thiophenyl, furanyl and thiazolyl, wherein the member may in each case be substituted with 1, 2, 3, 4 or 5 substituents selected, identically or differently, in each case, from the group consisting of F, Cl, Br, —CN, —CF$_3$, —OH, methoxy, ethoxy, n-propoxy, isopropoxy, n-butoxy, isobutoxy, tert-butoxy, methyl, ethyl, n-propyl, iso-propyl, n-butyl, iso-butyl, sec-butyl, tert-butyl, n-pentyl, —O—C(=O)-phenyl, phenyl and benzyl, wherein in each case the cyclic moiety of the groups —O—C(=O)-phenyl, phenyl and benzyl may be substituted with 1, 2, 3, 4 or 5 substituents selected, identically or differently, in each case, from the group consisting of F, Cl and Br;

R$^{24}$ and R 28, identically or differently, in each case, represent a phenyl group, wherein the group may in each case be substituted with 1, 2 or 3 substituents selected, identically or differently, in each case, from the group consisting of F, Cl, Br and —CF$_3$; and R$^{26}$ represents a 7,7-dimethyl-2-oxo-bicyclo[2.2.1]hept-1-yl group.

25. A compound according to claim 1, wherein said compound is selected from the group consisting of:

[1] 3 fluoro N [6 (4 fluoro benzoyl)5,6,7,8 tetrahydro pyrido[4,3 d]pyrimidin 2yl]benzamide,

[2] 3,5 dichloro N [6 (3 fluoro 4-methoxy-benzoyl)-5,6,7, 8-tetrahydro-pyrido[4,3 d]pyrimidin-2-yl]-benzamide,

[3] 4-tert-butyl-N-(6-hexanoyl-5,6,7,8-tetrahydro-pyrido [4,3d]pyrimidin-2-yl)-benzamide,

[4] N-(6-acetyl-5,6,7,8-tetrahydro-pyrido[4,3d]pyrimidin-2-yl)-3,4-dichloro-benzamide,

[5] 3,5-dichloro-N-[6-(3-trifluoromethyl-benzoyl)-5,6,7, 8-tetrahydro-pyrido[4,3 d]pyrimidin-2-yl]-benzamide,

[6] 3-chloro-N-[6-(4-methoxy-2,3,6-trimethyl-benzenesulfonyl)-5,6,7,8-tetrahydro-pyrido [4,3 d]pyrimidin-2-yl]-benzamide,

[7] N-[6-(2-ethoxy-benzoyl)-5,6,7,8-tetrahydro-pyrido [4,3 d]pyrimidin-2-yl]-3-fluoro-benzamide,

[8] 3-chloro-N-[6-(3-phenyl-propionyl)-5,6,7,8-tetrahydro-pyrido[4,3 d]pyrimidin-2-yl]-benzamide,

[9] 4-tert-butyl-N-[6-(isoxazole-5-carbonyl)-5,6,7,8-tetrahydro-pyrido[4,3 d]pyrimidin-2-yl]-benzamide,

[10] N-[6-(2-benzylsulfanyl-acetyl)-5,6,7,8-tetrahydro-pyrido[4,3 d]pyrimidin-2-yl]-2-methoxy-benzamide,

[11] thiophene-2-carboxylic acid {6-[2-(4-chloro-phenyl)-2-methyl-propionyl]-5,6,7,8-tetrahydro-pyrido [4,3 d]pyrimidin-2-yl}-amide,

[12] N-(6-benzoyl-5,6,7,8-tetrahydro-pyrido[4,3 d]pyrimidin-2-yl)-3-methyl-benzamide,

[13] N-[6-(2,3-dihydro-benzofuran-5-carbonyl)-5,6,7,8-tetrahydro-pyrido[4,3 d]pyrimidin-2-yl]-2-fluoro-benzamide,

[15] naphthalene-1 -carboxylic acid [6-(3-methyl-5-phenyl-isoxazole-4-carbonyl)-5,6,7,8-tetrahydro-pyrido [4,3 d]pyrimidin-2-yl]-amide,

[16] 3-chloro-N-{6-[2-(5-methyl-2-phenyl-thiazol-4-yl)-acetyl]-5,6,7,8-tetrahydro-pyrido [4,3 d]pyrimidin-2-yl}-benzamide,

[17] N-[6-(4-chloro-2,5-dimethyl-benzenesulfonyl)-5,6, 7,8-tetrahydro-pyrido[4,3 d]pyrimidin-2-yl]-2-trifluoromethyl-benzamide,

[18] N-[6-(1-benzenesulfonyl-1H-indole-2-carbonyl)-5,6, 7,8-tetrahydro-pyrido[4,3 d]pyrimidin-2-yl]-3-methoxy-benzamide,

[20] N-[6-(5-methyl-1-phenyl-1H-pyrazole-4-sulfonyl)-5,6,7,8-tetrahydro-pyrido [4,3 d]pyrimidin-2-yl]-2-trifluoromethyl-benzamide,

[21] N-[6-(3-chloro-2-methyl-benzenesulfonyl)-5,6,7,8-tetrahydro-pyrido[4,3 (d)]pyrimidin-2-yl]-3-fluoro-benzamide,

[22] 3,5-dichloro-N-[6-(3,5-dimethyl-isoxazole-4-carbonyl)-5,6,7,8-tetrahydro-pyrido [4,3 d]pyrimidin-2-yl]-benzamide,

[25] N-[6-(furan-2-carbonyl)-5,6,7,8-tetrahydro-pyrido [4,3 d]pyrimidin-2-yl]-3-methoxy-benzamide,

[26] N-{6-[4-(2,3-dihydro-indol-1-yl)-4-oxo-butyryl]-5, 6,7,8-tetrahydro-pyrido[4,3 d]pyrimidin-2-yl}-3-methyl-benzamide,

[27] N-{6-[2-(4-methyl-cyclohexyl)-acetyl]-5,6,7,8-tetrahydro-pyrido[4,3 d]pyrimidin-2-yl}-2-trifluoromethyl-benzamide,

[28] 3,4-difluoro—N-[6-(6-phenoxy-pyridine-3-carbonyl)-5,6,7,8-tetrahydro-pyrido [4,3 d]pyrimidin-2-yl]-benzamide,

[29] 4-tert-butyl—N-[6-(2-phenyl-thiazole-4-carbonyl)-5,6,7,8-tetrahydro-pyrido[4,3 d]pyrimidin-2-yl]-benzamide,

[30] 3,5-dichloro-N-[6-(2-trifluoromethyl-benzenesulfonyl) -5,6,7,8-tetrahydro-pyrido [4,3 d]pyrimidin-2-yl]-benzamide, 32] N-[6-(2-chloro-pyridine-4-carbonyl)-5,6,7,8-tetrahydro-pyrido[4,3 d]pyrimidin-2-yl]-3-methoxy-benzamide,

[35] N-(6-dimethylsulfamoyl-5,6,7,8-tetrahydro-pyrido [4,3 (d)]pyrimidin-2-yl)-3-fluoro-benzamide,

[36] 3-fluoro-N-{6-[2-(4-trifluoromethyl-phenyl) -acetyl]-5,6,7,8-tetrahydro-pyrido [4,3 (d)]pyrimidin-2-yl}-benzamide,

[37] N-{6-[2-(1,3-dioxo-1,3-dihydro-isoindol-2-yl)-acetyl]-5,6,7,8-tetrahydro-pyrido [4,3 (d)]pyrimidin-2-yl}-2-trifluoromethyl-benzamide,

[39] N-[6-(butane-1-sulfonyl)-5,6,7,8-tetrahydro-pyrido [4,3 (d)]pyrimidin-2-yl]-3-fluoro-benzamide,

[40] 2-methoxy-N-[6-(2-propyl-pentanoyl)-5,6,7,8-tetrahydro-pyrido[4,3 d]pyrimidin-2-yl]-benzamide,

[42] 4-chloro-N-[6-(2-trifluoromethyl-benzenesulfonyl)-5,6,7,8-tetrahydro-pyrido [4,3 d]pyrimidin-2-yl]-benzamide,

[44] 5-[2-(3,4-difluoro-benzoylamino)-7,8-dihydro-5H-pyrido[4,3 (d)]pyrimidin-6-yl ]-5-oxo-valeric acid methyl ester,

[45] N-[6-(benzo[b]thiophene-3-carbonyl)-5,6,7,8-tetrahydro-pyrido[4,3 d]pyrimidin-2-yl]-4-chloro-benzamide,

[48] N-{6-[2-(1H-indol-3-yl)-2-oxo-acetyl]-5,6,7,8-tetrahydro-pyrido[4,3 d]pyrimidin-2-yl}-2-trifluoromethyl-benzamide,

[50] N-[6-(2,5-dimethoxy-benzenesulfonyl)-5,6,7,8-tetrahydro-pyrido[4,3 d]pyrimidin-2-yl]-3-methoxy-benzamide,

[52] 3,4-difluoro-N-(6-hexanoyl-5,6,7,8-tetrahydro-pyrido[4,3 (d)]pyrimidin-2-yl)-benzamide,

[53] 4-ethyl-N-[6-(tetrahydro-furan-2-carbonyl)-5,6,7,8-tetrahydro-pyrido[4,3 d]pyrimidin-2-yl]-benzamide,

[54] N-[6-(2-chloro-benzenesulfonyl)-5,6,7,8-tetrahydro-pyrido[4,3 d]pyrimidin-2-yl ]-3-fluoro-benzamide,

[55] 4-tert-butyl-N-[6-(5-tert-butyl-2-methyl-2H-pyrazole-3-carbonyl)-5,6,7,8-tetrahydro-pyrido [4,3 d]pyrimidin-2-yl]-benzamide,

[56] 3-methoxy-N-[6-(4-methoxy-benzenesulfonyl)-5,6, 7,8-tetrahydro-pyrido[4,3 d]pyrimidin-2-yl]-benzamide,

[57] {2-[2-(3,4-difluoro-benzoylamino)-7,8-dihydro-5H-pyrido[4,3 d]pyrimidin-6-yl ]-2-oxo-1-phenyl-ethyl}-carbamic acid benzyl ester,

[59] 4-chloro-N-(6-dimethylsulfamoyl-5,6,7,8-tetrahydro-pyrido[4,3 d]pyrimidin-2-yl)-benzamide,

[60] 4-tert-butyl-N-[6-(2-fluoro-benzenesulfonyl)-5,6,7,8-tetrahydro-pyrido[4,3 d]pyrimidin-2-yl]-benzamide,

[61] 4-chloro-N-[6-(3-cyclopentyl-propionyl)-5,6,7,8-tetrahydro-pyrido[4,3 d]pyrimidin-2-yl]-benzamide,

[62] 4-chloro-N-[6-(4-phenyl-butyryl)-5,6,7,8-tetrahydro-pyrido[4,3 d]pyrimidin-2-yl]-benzamide,

[63] 4-tert-butyl-N-[6-(5-methyl-2-phenyl-2H-[1,2,3]triazole-4-carbonyl)-5,6,7,8-tetrahydro-pyrido [4,3 d]pyrimidin-2-yl]-benzamide,

[66] N-[6-(5-chloro-thiophene-2-sulfonyl)-5,6,7,8-tetrahydro-pyrido[4,3 d]pyrimidin-2-yl]-3-fluoro-benzamide,

[67] N-[6-(4-diethylamino-benzoyl)-5,6,7,8-tetrahydro-pyrido[4,3 d]pyrimidin-2-yl ]-3-methoxy-benzamide,

[68] N-[6-(2,4-dimethyl-thiazole-5-sulfonyl)-5,6,7,8-tetrahydro-pyrido[4,3 d]pyrimidin-2-yl]-3-methyl-benzamide,

[69] 4-chloro-N-[6-naphthalene-2-carbonyl)-5,6,7,8-tetrahydro-pyrido[4,3 d]pyrimidin-2-yl]-benzamide,

[70] N-[6-(2,4-difluoro-benzenesulfonyl)-5,6,7,8-tetrahydro-pyrido[4,3 d]pyrimidin-2-yl]-2-methoxy-benzamide,

[71] 3,4-dichloro-N-[6-(4-chloro-benzenesulfonyl)-5,6,7,8-tetrahydro-pyrido[4,3 d]pyrimidin-2-yl]-benzamide,

[72] 3,4-difluoro-N-[6-(thiophene-2-sulfonyl)-5,6,7,8-tetrahydro-pyrido[4,3 d]pyrimidin-2-yl]-benzamide,

[74] 4-ethyl-N-[6-(4-pyrazol-1-yl-benzoyl)-5,6,7,8-tetrahydro-pyrido[4,3 d]pyrimidin-2-yl]-benzamide,

[77] 3-[2-(4-chloro-benzoylamino)-7,8-dihydro-5H-pyrido[4,3 d]pyrimidin-6-yl]-3-oxo-propionic acid methyl ester,

[78] N-{6-[5-(4-chloro-phenyl)-2-methyl-furan-3-carbonyl]-5,6,7,8-tetrahydro-pyrido [4,3 d]pyrimidin-2-yl}-2-methoxy-benzamide,

[79] 4-chloro-N-[6-(2,4-dimethyl-thiazole-5-sulfonyl)-5,6,7,8-tetrahydro-pyrido [4,3 d]pyrimidin-2-yl]-benzamide,

[80] N-[6-(2,3-difluoro-benzoyl)-5,6,7,8-tetrahydro-pyrido[4,3 d]pyrimidin-2-yl]-3-methoxy-benzamide,

[81] 4-chloro-N-{6-[2-(2-methoxy-ethoxy)-acetyl]-5,6,7,8-tetrahydro-pyrido[4,3 d]pyrimidin-2-yl}-benzamide,

[82] 2-[2-(2-ethoxy-benzoylamino)-7,8-dihydro-5H-pyrido[4,3 d]pyrimidine-6-sulfonyl ]-benzoic acid methyl ester,

[83] 4-tert-butyl-N-[6-(4-nitro-benzenesulfonyl)-5,6,7,8-tetrahydro-pyrido[4,3 d]pyrimidin-2.yl]-benzamide,

[86] N-[6-(5-chloro-thiophene-2-sulfonyl)-5,6,7,8-tetrahydro-pyrido[4,3 d]pyrimidin-2-yl]-2-methoxy-benzamide,

[87] 4-fluoro-N-[6-(furan-2-carbonyl)-5,6,7,8-tetrahydro-pyrido[4,3 d]pyrimidin-2-yl]-benzamide,

[90] N-(6-ethanesulfonyl-5,6,7,8-tetrahydro-pyrido[4,3 d]pyrimidin-2-yl)-3-methoxy-benzamide,

[92] 4-tert-butyl-N-[6-(4-methyl-3-nitro-benzoyl)-5,6,7,8-tetrahydro-pyrido[4,3 d]pyrimidin-2-yl]-benzamide,

[95] 3,4-dichloro-N-[6-(2,4,6-trimethyl-benzenesulfonyl)-5,6,7,8-tetrahydro-pyrido [4,3 d]pyrimidin-2-yl]-benzamide,

[96] N-[6-(4-methyl-3,4-dihydro-2H-benzo[1,4]oxazine-7-sulfonyl)-5,6,7,8-tetrahydro-pyrido [4,3 d]pyrimidin-2-yl]-nicotinamide,

[99] thiophene-2-carboxylic acid[6-(2,3,5,6-tetramethyl-benzenesulfonyl)-5,6,7,8-tetrahydro-pyrido[4,3 d]pyrimidin-2-yl]-amide,

[101] N-[6-(3,4-dichloro-benzoyl)-5,6,7,8-tetrahydro-pyrido[4,3 d]pyrimidin-2-yl]-4-ethyl-benzamide,

[102] N-[6-(7,7-dimethyl-2-oxo-bicyclo[2.2.1]hept-1-yl-methanesulfonyl)-5,6,7,8-tetrahydro-pyrido [4,3 d]pyrimidin-2-yl]-3-fluoro-benzamide,

[103] N-[6-(6-fluoro-4H-benzo [1,3]dioxin-8-carbonyl)-5,6,7,8-tetrahydro-pyrido[4,3 d]pyrimidin-2-yl]-2-trifluoromethyl-benzamide,

[105] 2-ethoxy—N-[6-(4-oxo-pentanoyl)-5,6,7,8-tetrahydro-pyrido[4,3 d]pyrimidin-2-yl]-benzamide,

[106] naphthalene-1-carboxylic acid[6-(propane-1-sulfonyl)-5,6,7,8-tetrahydro-pyrido [4,3 d]pyrimidin-2-yl]-amide,

[107] N-[6-(5-fluoro-2-methyl-benzenesulfonyl)-5,6,7,8-tetrahydro-pyrido[4,3 d]pyrimidin-2-yl]-4-methyl-benzamide,

[109] 3-chloro-N-[6-(2-methyl-benzoyl)-5,6,7,8-tetrahydro-pyrido[4,3 d]pyrimidin-2-yl]-benzamide,

[110] thiophene-2-carboxylic acid[6-(3-chloro-benzo[b]thiophene-2-carbonyl)-5,6,7,8-tetrahydro-pyrido[4,3 d]pyrimidin-2-yl]-amide,

[113] N-[6-(3,4-dichloro-benzoyl)-5,6,7,8-tetrahydro-pyrido[4,3 d]pyrimidin-2-yl]-2-fluoro-benzamide,

[114] N-[6-(2-chloro-benzenesulfonyl)-5,6,7,8-tetrahydro-pyrido[4,3 d]pyrimidin-2-yl ]-4-ethyl-benzamide,

[116] 3-methyl-N-[6-(toluene-3-sulfonyl)-5,6,7,8-tetrahydro-pyrido[4,3 d]pyrimidin-2-yl]-benzamide,

[117] naphthalene-1-carboxylic acid[6-(5-chloro-thiophene-2-sulfonyl)-5,6,7,8-tetrahydro-pyrido [4,3 d]pyrimidin-2-yl]-amide,

[119] 3-chloro-N-[6-(3,4-dimethoxy-benzoyl)-5,6,7,8-tetrahydro-pyrido[4,3 d]pyrimidin-2-yl]-benzamide,

[120] N-[6-(3-chloro-benzo[b]thiophene-2-carbonyl)-5,6,7,8-tetrahydro-pyrido[4,3 d]pyrimidin-2-yl]-benzamide,

[121] 4-ethyl-N-[6-(thiophene-3-sulfonyl)-5,6,7,8-tetrahydro-pyrido[4,3 d]pyrimidin-2-yl]-benzamide,

[123] 2-ethoxy-N-[6-(2-ethylsulfanyl-pyridine-3-carbonyl)-5,6,7,8-tetrahydro-pyrido [4,3 d]pyrimidin-2-yl]-benzamide,

[124] 3-[2-(3-chloro-benzoylamino)-7,8-dihydro-5H-pyrido[4,3 d]pyrimidin-6-yl]-3-oxo-propionic acid ethyl ester,

[125] N-[6-(3-bromo-benzenesulfonyl)-5,6,7,8-tetrahydro-pyrido[4,3 d]pyrimidin-2-yl]-3-chloro-benzamide,

[126] 3,4-dichloro-N-{6-[2-(4-chloro-phenyl)-acetyl]-5,6,7,8-tetrahydro-pyrido[4,3 d]pyrimidin-2-yl}-benzamide,

[127] 3-chloro-N-[6-(2-chloro-6-fluoro-benzoyl)-5,6,7,8-tetrahydro-pyrido[4,3 d]pyrimidin-2-yl]-benzamide,

[129] N-[6-(5-bromo-2-methoxy-benzenesulfonyl)-5,6,7,8-tetrahydro-pyrido[4,3 d]pyrimidin-2-yl]-3-methoxy-benzamide,

[132] N-[6-(3-cyclopentyl-propionyl)-5,6,7,8-tetrahydro-pyrido[4,3 d]pyrimidin-2-yl ]-isonicotinamide,

[134] 3,4-dichloro-N-[6-(4-trifluoromethoxy-benzenesulfonyl)-5,6,7,8-tetrahydro-pyrido [4,3 d]pyrimidin-2-yl]-benzamide,

[136] N-[6-(3,4-dimethoxy-benzenesulfonyl)-5,6,7,8-tetrahydro-pyrido[4,3 d]pyrimidin-2-yl]-4-fluoro-benzamide,

[137] 2-fluoro-N-[6-(2-methyl-5-phenyl-furan-3-carbonyl)-5,6,7,8-tetrahydro-pyrido [4,3 d]pyrimidin-2-yl]-benzamide,

[141] 3-fluoro-N-[6-(1,2,3,4-tetrahydro-naphthalene-2-carbonyl)-5,6,7,8-tetrahydro-pyrido [4,3 d]pyrimidin-2-yl]-benzamide,
[142] 4-chloro-N-{6-[2-(2,5-dioxo-imidazolidin-4-yl)-acetyl]-5,6,7,8-tetrahydro-pyrido [4,3 d]pyrimidin-2-yl}-benzamide,
[143] 3-fluoro-N-[6-(toluene-4-sulfonyl)-5,6,7,8-tetrahydro-pyrido[4,3 d]pyrimidin-2-yl]-benzamide,
[144] 3,5-dichloro-N-[6-(4-thiophen-2-yl-benzoyl)-5,6,7,8-tetrahydro-pyrido[4,3 d]pyrimidin-2-yl]-benzamide,
[145] N-[6-(3-chloro-thiophene-2-carbonyl)-5,6,7,8-tetrahydro-pyrido[4,3 d]pyrimidin-2-yl]-2-ethoxy-benzamide,
[148] 4-methyl-N-[6-(4-trifluoromethylsulfanyl-benzoyl)-5,6,7,8-tetrahydro-pyrido [4,3 d]pyrimidin-2-yl]-benzamide,
[150] 2-fluoro-N-[6-(2-methyl-5-nitro-benzenesulfonyl)-5,6,7,8-tetrahydro-pyrido [4,3 d]pyrimidin-2-yl]-benzamide,
[152] 4-chloro-N-[6-(2,4-difluoro-benzoyl)-5,6,7,8-tetrahydro-pyrido[4,3 d]pyrimidin-2-yl]-benzamide
[153] 4-methyl-N-(6-pent-4-enoyl-5,6,7,8-tetrahydro-pyrido[4,3 d]pyrimidin-2-yl) -benzamide,
[154] naplithalene-1-carboxylic acid[6-(3-fluoro-4-methyl-benzoyl)-5,6,7,8-tetrahydro-pyrido [4,3 d]pyrimidin-2-yl]-amide,
[155] N-{6-[2-(4-trifluoromethyl-phenyl)-acetyl]-5,6,7,8-tetrahydro-pyrido[4,3 d]pyrimidin-2-yl}-benzamide,
[156] N-[6-(3,4-dichloro-benzoyl)-5,6,7,8-tetrahydro-pyrido[4,3 d]pyrimidin-2-yl]-nicotinamide,
[157] 4-ethyl-N-{6-[2-(2,2,2-trifluoro-acetyl)-1,2,3,4-tetrahydro-isoquinoline-7-sulfonyl ]-5,6,7,8-tetrahydro-pyrido[4,3 d]pyrimidin-2-yl}-benzamide,
[158] 2-methoxy-N-[6-(4-methoxy-2,3,6-trimethyl-benzenesulfonyl)-5,6,7,8-tetrahydro-pyrido [4,3 d]pyrimidin-2-yl]-benzamide,
[159] 4-ethyl-N-[6-(2-methoxy-acetyl)-5,6,7,8-tetrahydro-pyrido[4,3 d]pyrimidin-2-yl]-benzamide,
[170] naphthalene-1-carboxylic acid(6-acetyl-5,6,7,8-tetrahydro-pyrido[4,3 d]pyrimidin-2-yl)-amide,
[171] 3,5-dichloro-N-[6-(3-diethylcarbamoyl-propionyl)-5,6,7,8-tetrahydro-pyrido [4,3 d]pyrimidin-2-yl]-benzamide,
[172] 4-ethyl-N-[6-(4-methoxy-benzenesulfonyl)-5,6,7,8-tetrahydro-pyrido[4,3 d]pyrimidin-2-yl]-benzamide,
[173] 4-ethyl-N-[6-(quinoline-6-carbonyl)-5,6,7,8-tetrahydro-pyrido[4,3 d]pyrimidin-2-yl]-benzamide,
[174] N-[6-(2-cyclopropyl-acetyl)-5,6,7,8-tetrahydro-pyrido[4,3 d]pyrimidin-2-yl]-2-fluoro-benzamide,
[175] N-[6-(2H-chromene-3carbonyl)-5,6,7,8-tetrahydro-pyrido[4,3 d]pyrimidin-2-yl ]-3,4-difluoro-benzamide,
[176] N-{6-[2-(4-chloro-phenyl)-propionyl]-5,6,7,8-tetrahydro-pyrido[4,3 d]pyrimidin-2-yl}-benzamide,
[178] 4-fluoro-N-(6-phenylmethanesulfonyl-5,6,7,8-tetrahydro-pyrido[4,3 d]pyrimidin-2-yl) -benzamide,
[182] N-[6-(2,5-dimethyl-2H-pyrazole-3-carbonyl)-5,6,7,8-tetrahydro-pyrido[4,3 d]pyrimidin-2-yl]-4-ethyl-benzamide,
[183] naphthalene -1-carboxylic acid[6-(3-fluoro-benzoyl)-5,6,7,8-tetrahydro-pyrido [4,3 d]pyrimidin-2-yl]-amide,
[184] N-[6-(benzo[b]thiophene-3-carbonyl)-5,6,7,8-tetrahydro-pyrido[4,3 d]pyrimidin-2-yl]-4-tert-butyl-benzamide,
[185] 4-fluoro-N-[6-(4-methoxy-benzenesulfonyl)-5,6,7,8-tetrahydro-pyrido[4,3 d]pyrimidin-2-yl]-benzamide,
[186] 4-tert-butyl-N-[6-(2,3-dihydro-benzo[1,4]dioxin-6-sulfonyl)-5,6,7,8-tetrahydro-pyrido [4,3 d]pyrimidin-2-yl]-benzamide,
[187] 3-chloro-N-{6-[2-(2,6-dichloro-phenyl)-acetyl]-5,6,7,8-tetrahydro-pyrido[4,3 d]pyrimidin-2-yl}-benzamide,
[189] N-{6-[2-(3-chloro-phenoxy)-acetyl]-5,6,7,8-tetrahydro-pyrido[4,3 d]pyrimidin-2-yl}-4-methyl-benzamide,
[190] N-[6-(5-phenyl-pentanoyl) -5,6,7,8-tetrahydro-pyrido[4,3 d]pyrimidin-2-yl]-benzamide,
[191] 4-ethyl-N-[6-(2-ethyl-butyryl)-5,6,7,8-tetrahydro-pyrido[4,3 d]pyrimidin-2-yl ]-benzamide,
[192] 3,5-dichloro-N-[6-(4-trifluoromethoxy-benzoyl)-5,6,7,8-tetrahydro-pyrido[4,3 d]pyrimidin-2-yl]-benzamide,
[193] naphthalene-1-carboxylic acid[6-(4-methyl-octanoyl)-5,6,7,8-tetrahydro-pyrido [4,3 d]pyrimidin-2-yl]-amide,
[195] N-[6-(2-benzyloxy-acetyl)-5,6,7,8-tetrahydro-pyrido[4,3 d]pyrimidin-2-yl]-2-methoxy-benzamide,
[198] N-[6-(3-cyano-benzoyl)-5,6,7,8-tetrahydro-pyrido[4,3 d]pyrimidin-2-yl]-2-trifluoromethyl-benzamide,
[199] 3-methoxy-N-[6-(3-trifluoromethoxy-benzoyl)-5,6,7,8-tetrahydro-pyrido[4,3 d]pyrimidin-2-yl]-benzamide,
[200] N-(6-butyryl-5,6,7,8-tetrahydro-pyrido[4,3 d]pyrimidin-2-yl) -2-fluoro-benzamide,
[203] naphthalene-1-carboxylic acid (6-hexanoyl-5,6,7,8-tetrahydro-pyrido[4,3 d]pyrimidin-2-yl)-amide,
[204] N-(6-propionyl-5,6,7,8-tetrahydro-pyrido[4,3 d]pyrimidin-2-yl)-2-trifluoromethyl-benzamide,
[205] N-[6-(2-ethyl-butyryl)-5,6,7,8-tetrahydro-pyrido [4,3 d]pyrimidin-2-yl]-4-methyl-benzamide,
[206] 2-fluoro-N-[6-(3-trifluoromethyl-benzenesulfonyl)-5,6,7,8-tetrahydro-pyrido [4,3 d]pyrimidin-2-yl]-benzamide,
[210] 4-fluoro-N-[6-(propane-1-sulfonyl)-5,6,7,8-tetrahydro-pyrido[4,3 d]pyrimidin-2-yl]-benzamide,
[211] 2-[2-(3-fluoro-beuzoylamino)-7,8-dihydro-5H-pyrido[4,3 d]pyrimidine-6-sulfonyl ]-benzoic acid methyl ester,
[212] 3,5-dichloro-N-[6-(5-[1,2]dithiolan-3-yl-pentanoyl)-5,6,7,8-tetrahydro-pyrido [4,3 d]pyrimidin-2-yl]-benzamide,
[215] N-(6-cyclohexanecarboxylic-5,6,7,8-tetrahydro-pyrido[4,3 d]pyrimidin-2-yl)-2-trifluoromethyl-benzamide,
[216] N-[6-(2,4-dimethyl-thiazole-5-sulfonyl)-5,6,7,8-tetrahydro-pyrido[4,3 d]pyrimidin-2-yl]-2-trifluoromethyl-benzamide,
[223] 4-fluoro-N-[6-(4-methyl-octanoyl)-5,6,7,8-tetrahydro-pyrido[4,3 d]pyrimidin-2-yl]-benzamide,
[226] 3-chloro-N-(6-pentanoyl-5,6,7,8-tetrahydro-pyrido[4,3 d]pyrimidin-2-yl)-benzamide,
[232] 4-chloro-N-[6-(2-phenoxy-acetyl)-5,6,7,8-tetrahydro-pyrido[4,3 d]pyrimidin-2-yl]-benzamide,
[234] N-[6-(5-bromo-thiophene-2-carbonyl)-5,6,7,8-tetrahydro-pyrido[4,3 d]pyrimidin-2-yl]-2-fluoro-benzamide,
[238] 3,4-difluoro-N-[6-(quinoline-6-carbonyl)-5,6,7,8-tetrahydro-pyrido[4,3 d]pyrimidin-2-yl]-benzamide,
[241] 3-chloro-N-{6-[3-(2-oxo-benzooxazol-3-yl)-propionyl]-5,6,7,8-tetrahydro-pyrido [4,3 d]pyrimidin-2-yl}-benzamide,

[242] 3-chloro-N-[6-(5-chloro-thiophene-2-sulfonyl)-5,6,7,8-tetrahydro-pyrido[4,3 d]pyrimidin-2-yl]-benzamide,

[243] 3,5-dichloro-N-[6-(4-methoxy-benzenesulfonyl)-5,6,7,8-tetrahydro-pyrido[4,3 d]pyrimidin-2-yl]-benzamide,

[244] 4-tert-butyl—N-[6- (5-methyl-isoxazole-3-carbonyl)-5,6,7,8-tetrahydro-pyrido [4,3 d]pyrimidin-2-yl]-benzamide, [245] N-[6-(5-bromo-2-methoxy-benzenesulfonyl)-5,6,7,8-tetrahydro-pyrido[4,3 d]pyrimidin-2-yl]-4-methyl-benzamide,

[246] 4-tert-butyl-N-{6-[3-(2-hydroxyphenyl)-propionyl]-5,6,7,8-tetrahydro-pyrido [4,3 d]pyrimidin-2-yl}-benzamide,

[248]0 4-tert-butyl-N-[6-(4-propyl-benzoyl)-5,6,7,8-tetrahydro-pyrido[4,3 d]pyrimidin-2-yl]-benzamide,

[250] 2-methoxy-N-[6-(6-phenoxy-pyridine-3-carbonyl)-5,6,7,8-tetrahydro-pyrido [4,3 d]pyrimidin-2-yl]-benzamide,

[251] N-[6-(4-acetylamino-benzenesulfonyl)-5,6,7,8-tetrahydro-pyrido[4,3 d]pyrimidin-2-yl]-4-ethyl-benzamide, [252]3,5-dichloro—N-[6-(4-fluoro-benzenesulfonyl)-5,6,7,8-tetrahydro-pyrido[4,3 d]pyrimidin-2-yl]-benzamide, and

[253] N-[6-(1-benzenesulfonyl-1H-indole-2-carbonyl)-5,6,7,8-tetrahydro-pyrido[4,3 d]pyrimidin-2-yl]-4-fluoro-benzamide in each case optionally in the form of one of the stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts.

26. A pharmaceutical formulation comprising a compound according to claim 1 and at least one physiologically acceptable auxiliary substance.

\* \* \* \* \*